US012807945B2

(12) United States Patent
Ticau et al.

(10) Patent No.: US 12,807,945 B2
(45) Date of Patent: Nov. 24, 2026

(54) NEUROFILAMENT LIGHT CHAIN (NFL) AS A BIOMARKER FOR TRANSTHYRETIN AMYLOIDOSIS POLYNEUROPATHY

(71) Applicant: Alnylam Pharmaceuticals, Inc., Cambridge, MA (US)

(72) Inventors: Simina Ticau, Braintree, MA (US); Paul Nioi, Cambridge, MA (US); Gautham Vivek Sridharan, Cambridge, MA (US); Shira Tsour, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1050 days.

(21) Appl. No.: 17/672,771

(22) Filed: Feb. 16, 2022

(65) Prior Publication Data

US 2023/0024849 A1 Jan. 26, 2023

Related U.S. Application Data

(63) Continuation of application No. PCT/US2020/048509, filed on Aug. 28, 2020.

(60) Provisional application No. 63/044,163, filed on Jun. 25, 2020, provisional application No. 62/925,623, filed on Oct. 24, 2019, provisional application No. 62/894,237, filed on Aug. 30, 2019.

(51) Int. Cl.

*C12N 15/113* (2010.01)
*A61P 9/00* (2006.01)
*G01N 33/68* (2006.01)

(52) U.S. Cl.

CPC .............. *C12N 15/113* (2013.01); *A61P 9/00* (2018.01); *G01N 33/68* (2013.01); *C12N 2310/14* (2013.01); *G01N 2800/52* (2013.01)

(58) Field of Classification Search

CPC ................................ C12N 15/113; A61P 9/00
See application file for complete search history.

(56) References Cited

U.S. PATENT DOCUMENTS

| | | | |
|---|---|---|---|
| 7,250,496 | B2 | 7/2007 | Bentwich |
| 7,427,605 | B2 | 9/2008 | Davis et al. |
| 7,718,629 | B2 | 5/2010 | Bumcrot et al. |
| 8,168,775 | B2 | 5/2012 | Sah et al. |
| 8,741,866 | B2 | 6/2014 | Sah et al. |
| 9,101,643 | B2 | 8/2015 | Sah |
| 9,228,186 | B2 | 1/2016 | Khvorova et al. |
| 9,234,196 | B2 | 1/2016 | Sah et al. |
| 9,339,513 | B2 | 5/2016 | Gollob et al. |
| 9,399,775 | B2 | 7/2016 | Rajeev et al. |
| 9,708,607 | B2 | 7/2017 | Rajeev et al. |
| 9,777,270 | B2 | 10/2017 | Khvorova et al. |
| 9,796,974 | B2 | 10/2017 | Rajeev et al. |
| 10,060,921 | B2 | 8/2018 | Bettencourt |
| 10,208,307 | B2 | 2/2019 | Zimmermann et al. |
| 10,240,152 | B2 | 3/2019 | Sah et al. |
| 10,570,391 | B2 | 2/2020 | Rajeev et al. |
| 10,683,501 | B2 | 6/2020 | Zimmermann et al. |
| 11,079,379 | B2 | 8/2021 | Bettencourt |
| 11,286,486 | B2 | 3/2022 | Zimmermann et al. |
| 11,806,360 | B2 | 11/2023 | Gollob |
| 11,959,081 | B2 | 4/2024 | Schlegel et al. |
| 12,049,628 | B2 | 7/2024 | Zimmermann et al. |
| 2002/0160394 | A1 | 10/2002 | Wu |
| 2003/0072794 | A1 | 4/2003 | Boulikas |
| 2003/0124616 | A1 | 7/2003 | Jacobsen et al. |
| 2003/0143732 | A1 | 7/2003 | Fosnaugh et al. |
| 2003/0170891 | A1 | 9/2003 | McSwiggen |
| 2003/0191056 | A1 | 10/2003 | Walker et al. |
| 2003/0229037 | A1 | 12/2003 | Massing et al. |
| 2004/0119010 | A1 | 6/2004 | Perryman et al. |
| 2004/0259247 | A1 | 12/2004 | Tuschl et al. |
| 2005/0244869 | A1 | 11/2005 | Brown-Driver et al. |
| 2005/0276804 | A1 | 12/2005 | Smith et al. |
| 2006/0008910 | A1 | 1/2006 | MacLachlan et al. |
| 2006/0083780 | A1 | 4/2006 | Heyes et al. |
| 2006/0135460 | A1 | 6/2006 | Widder et al. |
| 2006/0240093 | A1 | 10/2006 | Maclachlan et al. |
| 2006/0263435 | A1 | 11/2006 | Davis et al. |
| 2007/0004664 | A1 | 1/2007 | McSwiggen et al. |
| 2007/0031844 | A1 | 2/2007 | Khvorova et al. |
| 2007/0135372 | A1 | 6/2007 | Maclachlan et al. |

(Continued)

FOREIGN PATENT DOCUMENTS

| | | | |
|---|---|---|---|
| EP | 2305805 | A1 | 4/2011 |
| WO | WO-2004015107 | A2 | 2/2004 |

(Continued)

OTHER PUBLICATIONS

Romano, Angela, et al. "Serum neurofilament light chain: a promising early diagnostic biomarker for hereditary transthyretin amyloidosis?." European Journal of Neurology 31.1 (2024): e16070. (Year: 2024).*

Carroll, A., Dyck, P. J., de Carvalho, M., Kennerson, M., Reilly, M. M., Kiernan, M. C., & Vucic, S. (2022). Novel approaches to diagnosis and management of hereditary transthyretin amyloidosis. Journal of Neurology, Neurosurgery & Psychiatry, 93(6), 668-678. (Year: 2022).*

U.S. Appl. No. 14/358,972 U.S. Pat. No. 9,399,775, filed May 16, 2014 Jul. 26, 2016, US 20140315835.

U.S. Appl. No. 15/188,317 U.S. Pat. No. 10,570,391, filed Jun. 21, 2016 Feb. 25, 2020, US 20160355817.

U.S. Appl. No. 16/738,014, filed Jan. 9, 2020, US 20200318111.

U.S. Appl. No. 17/371,182, filed Jul. 9, 2021, US 20230010288.

U.S. Appl. No. 18/509,440, filed Nov. 15, 2023, US 20240279652.

U.S. Appl. No. 19/390,806, filed Nov. 17, 2025.

(Continued)

*Primary Examiner* — Jennifer Dunston
*Assistant Examiner* — Christina Tran
(74) *Attorney, Agent, or Firm* — McCarter & English, LLP; Maria Laccotripe Zacharakis; Miao Yu

(57) ABSTRACT

The present invention provides biomarkers for diagnosis and monitoring of transthyretin (TTR) amyloidosis. The present invention further provides methods for selection of agents for treatment of TTR amyloidosis using the biomarkers. The present invention further provides kits for practicing the methods provided herein.

16 Claims, 13 Drawing Sheets

Specification includes a Sequence Listing.

(56) References Cited

U.S. PATENT DOCUMENTS

| | | | |
|---|---|---|---|
| 2007/0207974 | A1 | 9/2007 | Khvorova et al. |
| 2007/0281899 | A1 | 12/2007 | Bumcrot et al. |
| 2008/0188675 | A1 | 8/2008 | Chen et al. |
| 2009/0023215 | A1 | 1/2009 | Jessee et al. |
| 2009/0023673 | A1 | 1/2009 | Manoharan et al. |
| 2009/0082300 | A1 | 3/2009 | Brown-Driver et al. |
| 2009/0149403 | A1 | 6/2009 | MacLachlan et al. |
| 2009/0239814 | A1 | 9/2009 | Manoharan et al. |
| 2009/0247608 | A1 | 10/2009 | Manoharan et al. |
| 2009/0291131 | A1 | 11/2009 | MacLachlan et al. |
| 2010/0120893 | A1 | 5/2010 | Sah et al. |
| 2010/0130588 | A1 | 5/2010 | Yaworski et al. |
| 2010/0167267 | A1 | 7/2010 | Schulzknappe et al. |
| 2010/0267069 | A1 | 10/2010 | Kiernan et al. |
| 2010/0323381 | A1 | 12/2010 | Bergen et al. |
| 2010/0324120 | A1 | 12/2010 | Chen et al. |
| 2011/0015250 | A1 | 1/2011 | Bumcrot et al. |
| 2011/0237646 | A1 | 9/2011 | Smith et al. |
| 2011/0256175 | A1 | 10/2011 | Hope et al. |
| 2011/0294868 | A1 | 12/2011 | Monia et al. |
| 2012/0149109 | A1 | 6/2012 | Brown-Driver et al. |
| 2012/0225927 | A1 | 9/2012 | Sah et al. |
| 2012/0244207 | A1 | 9/2012 | Fitzgerald et al. |
| 2012/0294905 | A1 | 11/2012 | Sah |
| 2013/0197055 | A1 | 8/2013 | Kamens et al. |
| 2013/0217756 | A1 | 8/2013 | Cancilla et al. |
| 2013/0281510 | A1 | 10/2013 | Ando et al. |
| 2014/0194493 | A1 | 7/2014 | Sah et al. |
| 2014/0315835 | A1 | 10/2014 | Rajeev et al. |
| 2015/0057320 | A1 | 2/2015 | Petrukhin |
| 2016/0076029 | A1 | 3/2016 | Ando et al. |
| 2016/0264963 | A1 | 9/2016 | Sah et al. |
| 2016/0304870 | A1 | 10/2016 | Brown et al. |
| 2016/0355817 | A1 | 12/2016 | Rajeev et al. |
| 2017/0029817 | A1 | 2/2017 | Zimmermann et al. |
| 2017/0096663 | A1 | 4/2017 | Ando et al. |
| 2018/0119144 | A1 | 5/2018 | Khvorova et al. |
| 2018/0171332 | A1 | 6/2018 | Ando et al. |
| 2018/0320182 | A1 | 11/2018 | Khvorova et al. |
| 2019/0309293 | A1 | 10/2019 | Sah et al. |
| 2019/0345492 | A1 | 11/2019 | Zimmermann et al. |
| 2019/0350962 | A1 | 11/2019 | Chan et al. |
| 2020/0199592 | A1 | 6/2020 | Ando et al. |
| 2020/0283766 | A1 | 9/2020 | Sah et al. |
| 2020/0318111 | A1 | 10/2020 | Rajeev et al. |
| 2021/0361692 | A1 | 11/2021 | Gollob |
| 2022/0252593 | A1 | 8/2022 | Bettencourt |
| 2022/0333104 | A1 | 10/2022 | Nair et al. |
| 2023/0010288 | A1 | 1/2023 | Rajeev et al. |
| 2023/0022185 | A1 | 1/2023 | Zimmermann et al. |
| 2023/0024849 | A1 | 1/2023 | Ticau et al. |
| 2023/0111813 | A1 | 4/2023 | Schlegel et al. |
| 2023/0257740 | A1 | 8/2023 | Sah et al. |
| 2023/0304002 | A1 | 9/2023 | Nair et al. |
| 2023/0340473 | A1 | 10/2023 | Ando et al. |
| 2024/0075052 | A1 | 3/2024 | Gollob |
| 2024/0100080 | A1 | 3/2024 | Chan et al. |
| 2024/0200061 | A1 | 6/2024 | Nair et al. |
| 2024/0218369 | A1 | 7/2024 | Vest |
| 2024/0230644 | A1 | 7/2024 | Bettencourt |
| 2024/0279652 | A1 | 8/2024 | Rajeev et al. |
| 2024/0309375 | A1 | 9/2024 | Gollob et al. |
| 2024/0409929 | A1 | 12/2024 | Schlegel et al. |
| 2025/0075211 | A1 | 3/2025 | Zimmermann et al. |
| 2025/0376682 | A1 | 12/2025 | Sah et al. |

FOREIGN PATENT DOCUMENTS

| | | | |
|---|---|---|---|
| WO | WO-2004045543 | A2 | 6/2004 |
| WO | WO-2004/080406 | A2 | 9/2004 |
| WO | WO-2004/090108 | A2 | 10/2004 |
| WO | WO-2005/120152 | A2 | 12/2005 |
| WO | WO-2005/121348 | A1 | 12/2005 |
| WO | WO-2005/121370 | A2 | 12/2005 |
| WO | WO-2007/012191 | A1 | 2/2007 |
| WO | WO-2008/042973 | A2 | 4/2008 |
| WO | WO-2009/002944 | A1 | 12/2008 |
| WO | WO-2009/073809 | A2 | 6/2009 |
| WO | WO-2009/086558 | A1 | 7/2009 |
| WO | WO-2009/127060 | A1 | 10/2009 |
| WO | WO-2009/134487 | A2 | 11/2009 |
| WO | WO-2010/042877 | A1 | 4/2010 |
| WO | WO-2010/048228 | A2 | 4/2010 |
| WO | WO-2010/053572 | A2 | 5/2010 |
| WO | WO-2010/054406 | A1 | 5/2010 |
| WO | WO-2010/078536 | A1 | 7/2010 |
| WO | WO-2010/088537 | A2 | 8/2010 |
| WO | WO-2010/129709 | A1 | 11/2010 |
| WO | WO-2010/144740 | A1 | 12/2010 |
| WO | WO-2010/147992 | A1 | 12/2010 |
| WO | WO-2010/148013 | A2 | 12/2010 |
| WO | WO-2011/056883 | A1 | 5/2011 |
| WO | WO-2011/123468 | A1 | 10/2011 |
| WO | WO-2011/139917 | A1 | 11/2011 |
| WO | WO-2012/037254 | A1 | 3/2012 |
| WO | WO-2012/064824 | A1 | 5/2012 |
| WO | WO-2012/177906 | A1 | 12/2012 |
| WO | WO-2013/074974 | A2 | 5/2013 |
| WO | WO-2013/075035 | A1 | 5/2013 |
| WO | WO-2014/005596 | A1 | 1/2014 |
| WO | WO-2015/042564 | A1 | 3/2015 |
| WO | WO-2015/085158 | A1 | 6/2015 |
| WO | WO-2016028649 | A1 | 2/2016 |
| WO | WO-2016033326 | A2 | 3/2016 |
| WO | WO-2016/080853 | A1 | 5/2016 |
| WO | WO-2017/023660 | A1 | 2/2017 |
| WO | WO-2018/005967 | A1 | 1/2018 |
| WO | WO-2018/112320 | A1 | 6/2018 |
| WO | WO-2019/060442 | A1 | 3/2019 |
| WO | WO-2020/069055 | A1 | 4/2020 |
| WO | WO-2021/041884 | A1 | 3/2021 |
| WO | WO-2021/092145 | A1 | 5/2021 |
| WO | WO-2021/178778 | A1 | 9/2021 |
| WO | WO-2022/235537 | A1 | 11/2022 |
| WO | WO-2022/260939 | A2 | 12/2022 |
| WO | WO-2023/014677 | A1 | 2/2023 |

OTHER PUBLICATIONS

PCT/US2012/065691, Nov. 16, 2012, WO 2013/075035.
U.S. Appl. No. 15/221,651 U.S. Pat. No. 10,208,307, filed Jul. 28, 2016 Feb. 19, 2019, US 20170029817.
U.S. Appl. No. 16/223,362 U.S. Pat. No. 10,683,501, filed Dec. 18, 2018 Jun. 16, 2020, US 20190345492.
U.S. Appl. No. 16/864,226 U.S. Pat. No. 11,286,486, filed May 1, 2020 Mar. 29, 2022, US 20200377889.
U.S. Appl. No. 17/584,463 U.S. Pat. No. 12,049,628, filed Jan. 26, 2022 Jul. 30, 2024, US 20230022185.
U.S. Appl. No. 18/744,959, filed Jun. 17, 2024, US 20250075211.
PCT/US2016/044359, Jul. 28, 2016, WO 2017/023660.
U.S. Appl. No. 16/468,953, filed Jun. 12, 2019, US 20190350962.
U.S. Appl. No. 18/299,220, filed Apr. 12, 2023, US 20240100080.
PCT/US2017/066631, Dec. 15, 2017, WO 2018112320.
U.S. Appl. No. 17/213,294, filed Mar. 26, 2021, US 20220333104.
U.S. Appl. No. 18/225,919, filed Jul. 25, 2023, US 20240200061.
U.S. Appl. No. 19/247,022, filed Jun. 24, 2025.
PCT/US2019/053050, Sep. 26, 2019, WO 2020/069055.
U.S. Appl. No. 17/736,251, filed May 4, 2022, US 20230304002.
PCT/US2020/059070, Nov. 5, 2020, WO 2021/092145.
U.S. Appl. No. 17/899,957, filed Aug. 31, 2022.
PCT/US2021/021049, Mar. 5, 2021, WO 2021/178778.
U.S. Appl. No. 18/531,914, filed Dec. 7, 2023, US 20240309375.
PCT/US2022/032082, Jun. 3, 2022, WO 2022/260939.
U.S. Appl. No. 17/935,997 U.S. Pat. No. 11,959,081, filed Sep. 28, 2022 Apr. 16, 2024, US 20230111813.
U.S. Appl. No. 18/600,902, filed Mar. 11, 2024, US 20240409929.
PCT/US2022/076464, Aug. 2, 2022, WO 2023/014677.
PCT/US2020/048509, Aug. 28, 2020, WO 2021/041884.
U.S. Appl. No. 12/582,669 U.S. Pat. No. 8,168,775, filed Oct. 20, 2009 May 1, 2012, US 20100120893.

(56) References Cited

OTHER PUBLICATIONS

U.S. Appl. No. 13/410,262 U.S. Pat. No. 8,741,866, filed Mar. 1, 2012 Jun. 3, 2014, US 20120225927.
U.S. Appl. No. 14/220,829 U.S. Pat. No. 9,234,196, filed Mar. 20, 2014 Jan. 12, 2016, US 20140194493.
U.S. Appl. No. 14/965,825, filed Dec. 10, 2015, US 20160264963.
U.S. Appl. No. 15/380,571 U.S. Pat. No. 10,240,152, filed Dec. 15, 2016 Mar. 26, 2019, US 20170321213.
U.S. Appl. No. 16/276,541, filed Feb. 14, 2019, US 20190309293.
U.S. Appl. No. 16/751,026, filed Jan. 23, 2020, US 20200283766.
U.S. Appl. No. 17/102,351, filed Nov. 23, 2020.
U.S. Appl. No. 17/234,657, filed Apr. 19, 2021.
U.S. Appl. No. 17/360,849, filed Jun. 28, 2021.
U.S. Appl. No. 17/475,142, filed Sep. 14, 2021.
U.S. Appl. No. 17/721,704 U.S. Pat. No. 12,227,744, filed Apr. 15, 2022 Feb. 18, 2025, US 20230257740.
U.S. Appl. No. 19/013,039, filed Jan. 8, 2025, US 20250376682.
PCT/US2009/061381, Oct. 20, 2009, WO 2010/048228.
U.S. Appl. No. 13/636,594, filed May 2, 2013, US 20130281510.
U.S. Appl. No. 14/807,852, filed Jul. 23, 2015, US 20160076029.
U.S. Appl. No. 15/203,379, filed Jul. 6, 2016, US 20170096663.
U.S. Appl. No. 15/660,697, filed Jul. 26, 2017, US 20180171332.
U.S. Appl. No. 16/565,318, filed Sep. 9, 2019, US 20200199592.
U.S. Appl. No. 17/978,295, filed Nov. 1, 2022, US 20230340473.
U.S. Appl. No. 19/053,953, filed Feb. 14, 2025.
PCT/US2011/030392, Mar. 29, 2011, WO 2011/123468.
U.S. Appl. No. 13/884,601 U.S. Pat. No. 9,339,513, filed Sep. 11, 2013 May 17, 2016, US 20130345286.
PCT/US2011/059937, Nov. 9, 2011, WO 2012/064824.
U.S. Appl. No. 15/507,691 U.S. Pat. No. 10,00,921, filed Feb. 28, 2017 Aug. 28, 2018, US 20170307608.
U.S. Appl. No. 16/054,854 U.S. Pat. No. 11,079,379, filed Aug. 3, 2018 Aug. 3, 2021, US 20190162724.
U.S. Appl. No. 17/362,631, filed Jun. 29, 2021.
U.S. Appl. No. 17/475,098, filed Sep. 14, 2021, US 20220252593.
U.S. Appl. No. 18/382,562, filed Oct. 23, 2023, US 20240230644.
PCT/US2015/047185, Aug. 27, 2015, WO 2016/033326.
U.S. Appl. No. 16/648,558 U.S. Pat. No. 11,806,360, filed Mar. 18, 2020 Nov. 7, 2023, US 20210361692.
U.S. Appl. No. 18/476,506, filed Sep. 28, 2023, US 20240075052.
U.S. Appl. No. 19/181,733, filed Apr. 17, 2025.
PCT/US2018/051796, Sep. 19, 2018, WO 2019/060442.
U.S. Appl. No. 18/385,005, filed Oct. 30, 2023, US 20240218369.
PCT/US2022/027210, May 2, 2022, WO 2022/235537.
Ando Y., et al., "Pathogenesis and Therapy for Transthyretin Related Amyloidosis," Rinsho byori (the Japanese journal of clinical pathology), Feb. 2008, pp. 114-120, vol. 56 (With English Abstract).
Hornung V, et al., "Sequence-specific potent induction of IFN-a by short interfering RNA in plasmacytoid dendritic cells through TLR7". Nature Medicine, Mar. 2005, pp. 263-270, vol. 11, No. 3.
Judge A., et al., Confirming the RNAi-mediated mechanism of action of siRNA-based cancer therapeutics in mice. The Journal of Clinical Investigation, 2009 119(3): 661-673.
Elbashir, S., et al., "Analysis of gene function in somatic mammalian cells using small interfering RNAs," Methods, 2002, pp. 199-213, vol. 26.
Elbashir S, et al., Duplexes of 21-nucleotide RNAs mediate RNA interference in mammalian cell culture. Nature, May 24, 2001, pp. 494-498, vol. 411.
Akinc A., et al., A combinatorial library of lipid-like materials for delivery of RNAi therapeutics. Nature Biotechnology, 2008, vol. 26, pp. 561-569.
Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir et al., Functional anatomy of siRNAs for mediating efficient RNAi in *Drosophila melanogaster* embryo lysate. EMBO J. Dec. 3, 2001;20(23):6877-88.
Elbashir S, et al., RNA Interference id Mediated by 21- and 22 Nucleotide RNAs. Genes & Development, 2001, pp. 188-200, vol. 15.
Fire, A., "RNA-triggered Gene Silencing," Trends in Genetics, Sep. 1999, pp. 358-363, vol. 15, No. 9.
Fire A., at al., Potent and Specific Genetic Interference By Double Stranded RNA in Caenorhabditis elegans. Nature, Feb. 19, 1998, pp. 806-811, vol. 391.
Heyes J., et al., Cationic lipid saturation influences intracellular delivery of encapsulated nucleic acids. Journal of Controlled Release, 2005, pp. 276-287, vol. 107.
Kurosawa T., et al., Selective silencing of a mutant transthyretin allele by small interfering RNAs. Biochem. Biophys. Res. Commun., Nov. 25, 2005, vol. 337, No. 3, pp. 1012-1018.
Love K., et al., Lipid-like materials for low-dose, in vivo gene silencing. PNAS, Feb. 2, 2010, pp. 1864-1869, vol. 107, No. 5.
Maeda S., Use of genetically altered mice to study the role of serum amyloid P component in amyloid deposition. Amyloid, 2003, vol. 10, Suppl 1, pp. 17-20.
Morrissey D., et al., Potent and persistent in vivo anti-HBV activity of chemically modified siRNAs. Nature Biotechnology, Aug. 1, 2005, vol. 23, pp. 1002-1007.
Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Stein T., et al., Neutralization of transthyretin reverses the neuroprotective effects of secreted amyloid precursor protein (APP) in APP sw mice resulting in Tau phosphorylation and loss of Hippocampal neurons: support for the amyloid hypothesis. The Journal of Neuroscience, Sep. 1, 2004, vol. 24, No. 35, pp. 7707-7717.
Tuschl T., RNA Interference and Small Interfering RNAs. Chembiochem, 2001 pp. 39-245, vol. 2.
Tuschl T., et al., Small Interfering RNAs: A Revolutionary Tool for the Analysis of Gene Function and Gene Therapy. Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed.), 2003, pp. 265-295.
Tuschl, T., et al., "Targeted mRNA Degradation By Double-Stranded RNA In Vitro," Genes & Development, 1999, pp. 3191-3197, vol. 13.
Vickers T., et al., Efficient Reduction of Target RNAs by Small Interfering RNA and RNase H-dependent Antisense Agents. The Journal of Biological Chemistry, Feb. 28, 2003, pp. 7108-7118, vol. 278, No. 9.
Weil et al., Targeting the Kinesin Eg5 to Monitor siRNA Transfection in Mammalian Cells. Biotechniques, 2002, vol. 33, No. 6, pp. 1244-1248.
Prakash TP, et al., Positional Effect of Chemical Modifications on Short INterference RNA Activity in Mammalian Cells. J. Med. Chem. 48:4247-4253 (2005).
Collingwood MA., et al., Chemical Modification Patterns Compatible with High Potency Dicer-Substrate Small Interfering RNAs. Oliginucleotides, 18:187-200 (2008).
Bramsen JB, et al., A Large-Scale Chemical Modification Screen Identifies Design Rules to Generate siRNAs with High Activity, High Stability and Low Toxicity, Nucleic Acids Res. 37(9):2867-2881 (2009).
DeLeavey GF, et al., Synergistic Effects Between Analogs of DNA and RNA Improve the Potency of siRNA-Mediated Gene Silencing, Nucleic Acids Res. 38(13):4547-4557 (2010).
Ueda M, et al., SELDI-TOF mass spectrometry evaluation of variant transthyretins for diagnosis and pathogenesis of familial amyloidotic polyneuropathy. Clin. Chem 2009; 55(6):1223-1227; abstract, Table 1.
Schweigert FJ, et al., Characterization of the microheterogeneity of traansthyretin in plasma and urine using SELDI-TOF-MS immunoassay. Proteome Sci. 2004, 2(1) article 5, pp. 1-6.
Berquist J, et al., Rapid Method to Characterize Mutations in Transthyretin in Cerebrospinal Fluid from Familial Amyloidotic

(56) References Cited

OTHER PUBLICATIONS

Polyneuropathy Patients by Use of Matrix-assisted Laser Desorption/Ionization Time-of-Flight Mass Spectrometry. Clinical Chem. 2000, 46(9):1293-1300.
Hara R, et al., Impact of Liver Transplantation on Transthyretin-Related Ocular Amyloidosis in Japanese Patients. Arch Ophthalmol, Feb. 2010, pp. 206-210, vol. 128, No. 2.
Ueda M, et al., A transgenic rat with the human ATTR V30M: A novel tool for analysis of ATTY metabolisms. Biochemical and Biophysical Research Communications, 2006, pp. 299-304, vol. 352.
PCT International Search Report and Written Opinion, PCT/US2011/030392, Jun. 27, 2011, 10 pages.
Cendron L, et al., Amyloidogenic potential of transthyretin variants: insights from structural and computational analyses. J Biol Chem. Sep. 18, 2009;284(38):25832-41.
Trenchevska, et al., Mass spectrometric immunoassay for quantitative determination of transthyretin and its variants. Proteomics Aug. 9, 2011, 11(18):3633-3641; abstract p. 3633, para 1; p. 3634, para 5-6; p. 3635, para 1-4; p. 3636, para 2-3; p. 3637, para 2; p. 3639, para 3; Table 4; Figs 2-3.
Supplementary European Search Report for European Patent Application No. 10829034, Aug. 30, 2013, 9 pages.
Sekijima Y., et al., Pathogensis of and Therapeutic Strategies to Ameliorate the Transthyretin Amyloidoses. Current Pharmaceutical Design, Jan. 1, 2008, pp. 3219-3230, vol. 14, No. 30.
Benson M., et al., Targeted suppression of an amyloidogenic transthyretin with antisense oligonucleotides. Muscle & Nerve, Jan. 18, 2006, pp. 609-618, vol. 33, No. 5.
European Patent Office Communication pursuant to Article 94(3) EPC for European Patent Application No. 09 810 834.3, Feb. 15, 2012.
Examination Report for New Zealand Patent Application No. 592867, Jun. 14, 2011, 2 pages.
GenBank Accession No. NM_000371.3, *Homo sapiens* transthyretin (TTR), mRNA, Sep. 23, 2012.
GenBank Accession No. NM_000371.2, *Homo sapiens* transthyretin (TTR), mRNA, Dec. 21, 2008.
GenBank Accession No. NM_012681.1, Rattus norvegicus transthyretin (Ttr), mRNA, Feb. 14, 2010.
GenBank Accession No. NM_013697.2, Mus musculus transthyretin (Ttr), mRNA, Apr. 5, 2007.
PCT International Search Report and Written Opinion for International Patent Application No. PCT/US2010/055311, Mar. 2, 2011, 12 pages.
PCT International Search Report and Written Opinion for International Patent Application No. PCT/US2009/061381, Jul. 26, 2010.
Tuschl T., Functional genomics: RNA sets the standard. Nature, Jan. 16, 2003, vol. 421, No. 6920, pp. 220-221.
The State Intellectual Property Office of The People's Republic of China, Notification of the First Office Action, Chinese Patent Application No. 200980141740.4, Jun. 5, 2012.
Tuschl, T., "Expanding small RNA interference," Nature Biotechnology, May 2002, pp. 446-448, vol. 20.
Zimmerman TS., et al., RNAi-mediated gene silencing in non-human primates. Nature, May 4, 2006, vol. 441, pp. 111-114.
PCT Invitation to Pay Additional Fees and, Where Applicable, Protest Fee, PCT/US2009/061381, Apr. 27, 2010, 7 Pages.
International Search Report for International Application No. PCT/US2012/065407 dated Apr. 22, 2013.
Smith et al., "Knockdown of cortical transthyretin expression around implanted neural prosthetic devices using intraventricular siRNA injection in the brain", Journal of Neuroscience Methods, vol. 203(2), pp. 398-406 (2011).
WY Sah Dinah et al., "802: ALN-TTR, An RNAI Therapeutic For the Treatment Of Transthyretin Amyloidosis", Nucleic Acid Therapeutics, vol. 21(5), pp. A55-A56 ( Oct. 2011).
European Search Report from European Patent Application No. 12850255.6, dated May 11, 2015.
Kawasaki et al. "Synthesis, hybridization, and nuclease resistance properties of 2 '-O-aminooxyethyl (2 '-O-AOE) modified oligonucleotides", Tetrahedron Letters, 1999, 40, 661-664.
Czauderna et al.,"Structural variations and stabilising modifcations of synthetic siRNAs in mammalian cells", Nucleic Acids Research, 31(11)2705-2716, 2003.
Behlke, "Chemical Modification of siRNAs for In Vivo Use", Oligonucleotides, 18(4) 305-320 2008.
Extended European Search Report from EO 17184486.3 mailed Jan. 29, 2018.
Chen et al. "Lipophilic siRNAs mediate efficient gene silencing in oligodendrocytes with direct CNS delivery", Journal of Controlled Release (2010).
Nakamura et al., "Targeted Conversion of the Transthyretin Gene in Vitro and in Vivo", Gene Therapy (2004) 11, 838-846.
Manoharan, "RNA interference and chemically modified small interfering RNAs", Current Opinion in Chemical Biology 2004, 8:570-579.
Gambari et a;. "Targeting microRNAs involved in human diseases: A novel approach for modification of gene expression and drug development", Biochemical Pharmacology 82 (2011) 1416-1429.
Alnylam Pharmaceuticals Discontinues Revusiran Development, Press Release, Oct. 5, 2016.
International Search Report and Written Opinion from PCT/US2016/044359 mailed Nov. 7, 2016.
Reynolds et al., Rational siRNA design for RNA interference. Nat Biotechnol. Mar. 2004;22(3):326-30.
Conceição et al. "Early diagnosis of ATTR amyloidosis through targeted follow-up of identified carries of TTR gene mutations*," Amyloid, vol. 26, No. 1, pp. 3-9 (2019).
Coelho et al., "Safety and Efficacy of RNAi Therapy for Transthyretin Amyloidosis", N Engl J Med 2013; 369:819-829.
Butler et al., "Preclinical evaluation of RNAi as a treatment for transthyretin-mediated amyloidosis", Amyloid, 2016; 23(2): 109-118.
Salim et al., "Effective carrier-free gene-silencing activity of cholesterol-modified siRNAs", RSC Adv., 2018, 8, 22963.
International Preliminary Report on Patentability from PCT/US2019/053050, mailed Apr. 8, 2021.
Farnoodian et al., "Cell-autonomous lipid-handling defects in Stargardt iPSC-derived retinal pigment epithelium cells", Stem Cell Reports, vol. 17, 2438-2450, Nov. 8, 2022.
International Search Report and Written Opinion from PCT/US2022/039111, mailed Nov. 22, 2022.
Brown et al., "Investigating the pharmacodynamic durability of GalNAc-siRNA conjugates", Nucleic Acids Research, 2020, vol. 48, No. 21 11827-11844.
Internation Search Report and Written Opinion PCT/US2018/051796, mailed Mar. 1, 2019.
Adams et al., "Trial design and rationale for APOLLO, a Phase 3, placebo-controlled study of patisiran in patients with hereditary ATTR amyloidosis with polyneuropathy," BMC Neurol 17, 181 (2017).
Raghu et a;., "Interactions amongst plasma retinol-binding protein, transthyretin and their ligands: implications in vitamin A homeostasis and transthyretin amyloidosis", Biochim Biophys Acta. Dec. 1, 2004;1703(1):1-9.
Adams et al., "Patisiran, an RNAi Therapeutic, for Hereditary Transthyretin Amyloidosis", N Engl J Med 2018; 379:11-21.
Ole Suhr "Cinical Update on Patisiran 1-21, Phase 2 Trials in Familial Amyloidotic 26-32 Polyneuropathy" Apr. 30, 2014.
International Search Report for International Application No. PCT/US2017/066631 dated Mar. 22, 2018.
International Search Report for International Application No. PCT/US2020/059070 dated Apr. 12, 2021.
International Search Report for International Application No. PCT/US2022/032082, dated Dec. 15, 2022.
Hayashi et al. "Recent Advances in Oligonucleotide-Based Therapy for Transthyretin Amyloidosis: Clinical Impact and Future Prospects", Biol Pharm Bull. 2018;41(12):1737-1744.
Garber, "Alnylam launches era of RNAi drugs", Nat Biotechnol. Sep. 6, 2018;36(9):777-778.

(56) References Cited

OTHER PUBLICATIONS

Roberts et al., "Advances in oligonucleotide drug delivery", Nat Rev Drug Discov. Oct. 2020;19(10):673-694.
Weng et al., " RNAi therapeutic and its innovative biotechnological evolution", vol. 37, Issue 5, Sep.-Oct. 2019, pp. 801-825.
Cioffi et al., "Identification of Transthyretin Tetramer Kinetic Stabi lizers That Are Capab1e of Inhibiting the Retino1-Dependent Retino1 Binding Protein 4-Transthyretin Interaction", Feb. 25, 2021 (Feb. 25, 2021), Retrieved from the Internet: URL:https://chemrxiv.org/engage/api-gateway/chemrxiv/assets/orp/resource/item/60c75572bdbb89260da3a80e/origina1/identification-of-transthyretin-tetramer-kinetic-stabilizers-that-are-capable-of-inhibiting-the-retino1-dependent-retino1-binding-protein-4-transthyretin-interaction.pdf.
International Search Report from International Application No. PCT/US2021/021049, dated May 20, 2021.
International Search Report for International Application No. PCT/US2015/047185, dated Feb. 9, 2016.
Sekijima, Y., "Recent Progress In The Understanding And Treatment Of Transthyretin Amyloidosis," Journal of Clinical Pharmacy and Therapeutics, Jun. 2014. vol. 39, No. 3, pp. 225-233.
Extended European Search Report for EP 22175295.9, dated Jan. 12, 2023.
Anon, "Clinical Updates on ALN-TTR Programs Patisiran (ALN-TTR02) and ALN-TTRsc for the Treatment of Transthyretin Amyloidosis", International Symposium on Familial Amyloidotic Polyneuropathy, Nov. 10, 2013.
Anonymous: "The Study of an Investigational Drug, ALN-TTR02, for the Treatment of Transthyretin (TTR)-Mediated Amyloidosis—Tabular View—ClinicalTrials.gov", Apr. 15, 2014.
Coelho, "Phase 2 open-label extension study of patisiran, an investigational RNAi therapeutic for the treatment of familial amyloid polyneuropathy (S9.003)", Neurology, Apr. 21, 2015.
Coelho et al.,"Safety and Efficacy of RNAi Therapy for Transthyretin Amyloidosis: Protocol", New England Journal of Medicine, Aug. 29, 2013 (Aug. 29, 2013), pp. 819-829.
Anon: "Safety and Efficacy of RNAi Therapy for Transthyretin Amyloidosis: Protocol", clinicaltrials.gov, Jan. 16, 2013.
Gillmore et al: "A Phase 2 Multi-Center, Open-Label Trial to Evaluate the Safety, Pharmacokinetics, Pharmacodynamics and Exploratory Clinical Activity of Revusiran (ALN-TTRsc), an RNAi Therapeutic for the Treatment of Patients with Transthyretin Cardiac Amyloidosis", Mar. 15, 2015.
Anonymous: "Alnylam Pharmaceuticals Press Release I Nov. 14, 2014 I Alnylam Announces Positive Initial Phase 2 Data with Revusiran (ALNTTRsc), an Investigational RNAi Therapeuti", Nov. 14, 2014.
International Search Report for International Application No. PCT/US2020/048509, dated Nov. 4, 2020.
Sandelius et al., "Plasma neurofilament light chain concentration in the inherited peripheral neuropathies", Neurology. Feb. 6, 2018; 90(6): e518-e524.
Benson et al., "Inotersen Treatment for Patients with Hereditary Transthyretin Amyloidosis", N Engl J Med 2018; 379:22-31.
Alnylam Pharmaceuticals, "Phase 2 Open-Label Extension Study of Patisiran—An RNAi Therapeutic for the Treatment of Familial Amyloidotic Polyneuropathy," Apr. 22, 2015, 29 pages.
Gertz et al., "Diagnosis, Prognosis, and Therapy of Transthyretin Amyloidosis", JACC vol. 66, No. 21, 2015.
Suhr et al, "Efficacy and safety of patisiran for familial amyloidotic polyneuropathy: a phase II multi-dose study", Orphanet Journal of Rare Diseases (2015) 10:109.
Notice of Preliminary Rejection for Korean Patent Application No. 10-2020-7011266, issued Dec. 14, 2023.
Springer et al., "GalNAc-siRNA Conjugates: Leading the Way for Delivery of RNAi Therapeutics", Nucleic Acids Therapeutics, vol. 28, No. 3: 109-118. 2018.
Huang et al., "Preclinical and Clinical Advances of GalNAc-Decorated Nucleic Acid Therapeutics", Molecular Therapy-Nucleic Acids, vol. 6: 116-132. 2017.
Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Res. Apr. 2008;36(7):2136-51.
Shukla et al., "Exploring chemical modifications for siRNA therapeutics: a structural and functional outlook", ChemMedChem. Mar. 1, 2010;5(3):328-49.
Nair et al., "Impact of enhanced metabolic stability on pharmacokinetics and pharmacodynamics of GalNAc-siRNA conjugates". Nucleic Acids Res. Nov. 2, 2017;45(19):10969-10977.
Nair et al. "Multivalent N-Acetylgalactosamine-Conjugated siRNA Localizes in Hepatocytes and Elicits Robust RNAi-Mediated Gene Silencing" J. Am. Chem. Soc. 2014, 136, 16958-16961.
Foster et al., "Advanced siRNA Designs Further Improve In Vivo Performance of GalNAc-siRNA Conjugates", Mol Ther. Mar. 7, 2018;26(3):708-717.
Chernikov et al., "Current Development of siRNA Bioconjugates: From Research to the Clinic", Front Pharmacol. Apr. 26, 2019:10:444.
Hu et al., "Therapeutic siRNA: state of the art", Signal Transduction and Targeted Therapy (2020) 5:101.
Tai, "Current Aspects of siRNA Bioconjugate for In Vitro and In Vivo Delivery", Molecules, vol. 24, No. 12, Jun. 13, 2019.
Biscans et al., "Diverse lipid conjugates for functional extra-hepatic siRNA delivery in vivo", Nucleic Acids Research, vol. 47, No. 3, Dec. 14, 2018, pp. 1082-1096.
Ueno et al., "Synthesis and silencing properties of siRNAs possessing lipophilic groups at their 3'-termini", Bioorganic & Medicalchemistry, vol. 16, No. 16, Aug. 15, 2008, pp. 7698-7704.
Wolfrum et al., "Mechanisms and optimization of in vivo delivery of lipophilic siRNAs" Nature Biotechnology, vol. 25, No. 10,Oct. 1, 2007, pp. 1149-1157.
Kubo et al., "Palmitic Acid-Conjugated 21-Nucleotide siRNA Enhances Gene-Silencing Activity", Molecular Pharmaceutics, vol. 8, No. 6, Dec. 5, 2011, pp. 2193-2203.
Kubo, "In Vivo RNAi Efficacy of Palmitic Acid-Conjugated Dicer-Substrate siRNA in a Subcutaneous Tumor Mouse Model", Chemical Biology & Drug Design, vol. 87, No. 6, Jun. 1, 2016,pp. 811-823.
PCT International Preliminary Report on Patentability No. PCT/US2020/059070, mailed May 19, 2022.
Adams, D et al., "FAP Neuropathy and Emerging Treatments," Current Neurology and Neuroscience Reports, Feb. 1, 2014. vol. 14, No. 3, pp. 1-12.
Almeida, M.-R., et al., "Small Transthyretin (TTR) Ligands as Possible Therapeutic Agents in TTR Amyloidoses," Current Drug Targets—CNS & Neurological Disorders, Oct. 2005, pp. 587-596, vol. 4, No. 5.
Berk, J. et al., "Repurposing Diflunisal for Familial Amyloid Polyneuropathy: A Randomized Clinical Trial," The Journal of the American Medical Association 310(24), Dec. 25, 2013, pp. 2658-2667.
Coelho, T. et al., "Long-Term Effects ofTafamidis for the Treatment of Transthyretin Familial Amyloid Polyneuropathy," Journal of Neurology 260, Aug. 22, 2013, pp. 2802-2814.
Dyck, P. et al., "Detection, Characterization, and Staging of Polyneuropathy: Assessed in Diabetics," Muscle Nerve 11(1), Jan. 1988, pp. 21-32.
Dyck, P. et al., "Longitudinal Assessment of Diabetic Polyneuropathy Using a Composite Score in the Rochester Diabetic Neuropathy Study Cohort," Neurology, Jul. 1997, 49, pp. 229-239.
Lozeron, P. et al., "Effect on Disability and Safety of Tafamidis in Late Onset ofMet30 Transthyretin Familial Amyloid Polyneuropathy," European Journal Neurology 20(12), Dec. 2013, pp. 1539-1545.
Morsles, "Collagen gel contraction by ARPE-19 cells is mediated by a FAK-Src dependent pathway," Experimental Eye Research, 2007, pp. 790-798 , vol. 85.
Santos, et al ., "Intraocular Delivery of Oligonucleotides ," Current Pharmaceutical Biotechnology , 2005 , pp. 7-15, vol. 6.
Suanprasert et al ., "Retrospective Study of a TTR FAP Cohort to Modify NIS + 7 for Therapeutic Trials ," Journal of the Neuro logical Sciences 344 , Jun. 27 , 2014 , pp. 121-128.

(56) References Cited

OTHER PUBLICATIONS

Tasaki et al . , “siRNA therapy for TTR—related ocular amyloidosis ,” Amyloid , 12th International Symposium on Amyloidosis from Molecular Mechanisms Toward the Cure of Systemic AM , 2010 , pp. 52-53vol. 17 , No. Suppl 1.
Androsavich, “Frameworks for transformational breakthroughs in RNA-based medicines”, Nature Reviews Drug Discovery, vol. 23, Jun. 2024, 421-444.
Coelho et al., “Mechanism of Action and Clinical Application of Tafamidis in Hereditary Transthyretin Amyloidosis”, Neurol Ther. Feb. 19, 2016;5(1):1-25.
Van Lieverloo et al., “Serum neurofilament light chain in chronic inflammatory demyelinating polyneuropathy”, Journal of the Peripheral Nervous System, vol. 23, No. 4, Poster66, Dec. 1, 2018, p. 277.

* cited by examiner

SEQUENCE LISTING

<160> NUMBER OF SEQ ID NOS: 26

<210> SEQ ID NO 1
<211> LENGTH: 543
<212> TYPE: PRT
<213> ORGANISM: Homo sapiens

<400> SEQUENCE: 1

```
Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
        115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
            180                 185                 190
```

-continued

```
Met Glu Ala Arg Lys Gly Ala Asp Glu Ala Ala Leu Ala Arg Ala Glu
        195                 200                 205

Leu Glu Lys Arg Ile Asp Ser Leu Met Asp Glu Ile Ser Phe Leu Lys
    210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255

Ala Leu Lys Asp Ile Arg Ala Gln Tyr Glu Lys Leu Ala Ala Lys Asn
            260                 265                 270

Met Gln Asn Ala Glu Glu Trp Phe Lys Ser Arg Phe Thr Val Leu Thr
        275                 280                 285

Glu Ser Ala Ala Lys Asn Thr Asp Ala Val Arg Ala Ala Lys Asp Glu
    290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                325                 330                 335

Glu Asp Lys Gln Asn Ala Asp Ile Ser Ala Met Gln Asp Thr Ile Asn
            340                 345                 350

Lys Leu Glu Asn Glu Leu Arg Thr Thr Lys Ser Glu Met Ala Arg Tyr
        355                 360                 365

Leu Lys Glu Tyr Gln Asp Leu Leu Asn Val Lys Met Ala Leu Asp Ile
    370                 375                 380

Glu Ile Ala Ala Tyr Arg Lys Leu Leu Glu Gly Glu Glu Thr Arg Leu
385                 390                 395                 400

Ser Phe Thr Ser Val Gly Ser Ile Thr Ser Gly Tyr Ser Gln Ser Ser
                405                 410                 415

Gln Val Phe Gly Arg Ser Ala Tyr Gly Gly Leu Gln Thr Ser Ser Tyr
            420                 425                 430

Leu Met Ser Thr Arg Ser Phe Pro Ser Tyr Tyr Thr Ser His Val Gln
        435                 440                 445

Glu Glu Gln Ile Glu Val Glu Glu Thr Ile Glu Ala Ala Lys Ala Glu
    450                 455                 460

Glu Ala Lys Asp Glu Pro Pro Ser Glu Gly Glu Ala Glu Glu Glu Glu
465                 470                 475                 480

Lys Asp Lys Glu Glu Ala Glu Glu Glu Glu Ala Ala Glu Glu Glu Glu
                485                 490                 495

Ala Ala Lys Glu Glu Ser Glu Glu Ala Lys Glu Glu Glu Glu Gly Gly
            500                 505                 510

Glu Gly Glu Glu Gly Glu Glu Thr Lys Glu Ala Glu Glu Glu Glu Lys
        515                 520                 525

Lys Val Glu Gly Ala Gly Glu Glu Gln Ala Ala Lys Lys Lys Asp
    530                 535                 540
```

<210> SEQ ID NO 2
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
ugggauuuca uguaaccaag a 21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 3
auggaauacu cuugguuact t 21

<210> SEQ ID NO 4
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
ucuugguuac augaaauccc auc 23

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
tcttggttac atgaaatccc 20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
tcttggttac atgaaatccc 20

<210> SEQ ID NO 7
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7
auggaauacu cuugguuac 19

<210> SEQ ID NO 8
<211> LENGTH: 19

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
guaaccaaga guauuccau 19

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 9
guaaccaaga guauuccaut t 21

<210> SEQ ID NO 10
<211> LENGTH: 284
<212> TYPE: PRT
<213> ORGANISM: Homo sapiens

<400> SEQUENCE: 10

```
Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
        115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
            180                 185                 190

Met Glu Ala Arg Lys Gly Ala Lys Asn Thr Asp Ala Val Arg Ala Ala
        195                 200                 205

Lys Asp Glu Val Ser Glu Ser Arg Arg Leu Leu Lys Ala Lys Thr Leu
    210                 215                 220
```

```
Glu Ile Glu Ala Cys Arg Gly Met Asn Glu Ala Leu Glu Lys Gln Leu
225                 230                 235                 240

Gln Glu Leu Glu Asp Lys Gln Asn Ala Asp Ile Ser Val Met Gln Asp
                245                 250                 255

Thr Ile Asn Lys Leu Glu Asn Glu Leu Arg Thr Thr Lys Ser Glu Met
            260                 265                 270

Ala Arg Tyr Leu Lys Glu Tyr Gln Asp Leu Leu Thr
        275                 280


<210> SEQ ID NO 11
<211> LENGTH: 272
<212> TYPE: PRT
<213> ORGANISM: Homo sapiens

<400> SEQUENCE: 11

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270


<210> SEQ ID NO 12
<211> LENGTH: 203
<212> TYPE: PRT
<213> ORGANISM: Homo sapiens

<400> SEQUENCE: 12
```

```
Met Lys Gln Ile Gly Val Cys Leu Ser Ser Cys Pro Ser Gly Tyr Tyr
1               5                   10                  15

Gly Thr Arg Tyr Pro Asp Ile Asn Lys Cys Thr Lys Cys Lys Ala Asp
            20                  25                  30

Cys Asp Thr Cys Phe Asn Lys Asn Phe Cys Thr Lys Cys Lys Ser Gly
        35                  40                  45

Phe Tyr Leu His Leu Gly Lys Cys Leu Asp Asn Cys Pro Glu Gly Leu
    50                  55                  60

Glu Ala Asn Asn His Thr Met Glu Cys Val Ser Ile Val His Cys Glu
65                  70                  75                  80

Val Ser Glu Trp Asn Pro Trp Ser Pro Cys Thr Lys Lys Gly Lys Thr
                85                  90                  95

Cys Gly Phe Lys Arg Gly Thr Glu Thr Arg Val Arg Glu Ile Ile Gln
            100                 105                 110

His Pro Ser Ala Lys Gly Asn Leu Cys Pro Pro Thr Asn Glu Thr Arg
        115                 120                 125

Lys Cys Thr Val Gln Arg Lys Lys Cys Gln Lys Gly Glu Arg Gly Lys
    130                 135                 140

Lys Gly Arg Glu Arg Lys Arg Lys Lys Pro Asn Lys Gly Glu Ser Lys
145                 150                 155                 160

Glu Ala Ile Pro Asp Ser Lys Ser Leu Glu Ser Ser Lys Glu Ile Pro
                165                 170                 175

Glu Gln Arg Glu Asn Lys Gln Gln Gln Lys Lys Arg Lys Val Gln Asp
            180                 185                 190

Lys Gln Lys Ser Val Ser Val Ser Thr Val His
        195                 200


<210> SEQ ID NO 13
<211> LENGTH: 224
<212> TYPE: PRT
<213> ORGANISM: Homo sapiens

<400> SEQUENCE: 13

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175
```

Arg Glu Ile Ile Gln His Pro Ser Ala Lys Gly Asn Leu Cys Pro Pro
        180                 185                 190

Thr Asn Glu Thr Arg Lys Cys Thr Val Gln Arg Lys Lys Cys Gln Lys
    195                 200                 205

Gly Glu Arg Gly Arg Thr Ser Arg Gly Asp Glu Arg Cys Phe Asn His
    210                 215                 220

<210> SEQ ID NO 14
<211> LENGTH: 553
<212> TYPE: PRT
<213> ORGANISM: Homo sapiens

<400> SEQUENCE: 14

Met Thr Trp Arg Met Gly Pro Arg Phe Thr Met Leu Leu Ala Met Trp
1               5                   10                  15

Leu Val Cys Gly Ser Glu Pro His Pro His Ala Thr Ile Arg Gly Ser
            20                  25                  30

His Gly Gly Arg Lys Val Pro Leu Val Ser Pro Asp Ser Ser Arg Pro
        35                  40                  45

Ala Arg Phe Leu Arg His Thr Gly Arg Ser Arg Gly Ile Glu Arg Ser
    50                  55                  60

Thr Leu Glu Glu Pro Asn Leu Gln Pro Leu Gln Arg Arg Arg Ser Val
65                  70                  75                  80

Pro Val Leu Arg Leu Ala Arg Pro Thr Glu Pro Pro Ala Arg Ser Asp
                85                  90                  95

Ile Asn Gly Ala Ala Val Arg Pro Glu Gln Arg Pro Ala Ala Arg Gly
            100                 105                 110

Ser Pro Arg Glu Met Ile Arg Asp Glu Gly Ser Ser Ala Arg Ser Arg
        115                 120                 125

Met Leu Arg Phe Pro Ser Gly Ser Ser Ser Pro Asn Ile Leu Ala Ser
    130                 135                 140

Phe Ala Gly Lys Asn Arg Val Trp Val Ile Ser Ala Pro His Ala Ser
145                 150                 155                 160

Glu Gly Tyr Tyr Arg Leu Met Met Ser Leu Leu Lys Asp Asp Val Tyr
                165                 170                 175

Cys Glu Leu Ala Glu Arg His Ile Gln Gln Ile Val Leu Phe His Gln
            180                 185                 190

Ala Gly Glu Glu Gly Gly Lys Val Arg Arg Ile Thr Ser Glu Gly Gln
        195                 200                 205

Ile Leu Glu Gln Pro Leu Asp Pro Ser Leu Ile Pro Lys Leu Met Ser
    210                 215                 220

Phe Leu Lys Leu Glu Lys Gly Lys Phe Gly Met Val Leu Leu Lys Lys
225                 230                 235                 240

Thr Leu Gln Val Glu Glu Arg Tyr Pro Tyr Pro Val Arg Leu Glu Ala
                245                 250                 255

Met Tyr Glu Val Ile Asp Gln Gly Pro Ile Arg Arg Ile Glu Lys Ile
            260                 265                 270

Arg Gln Lys Gly Phe Val Gln Lys Cys Lys Ala Ser Gly Val Glu Gly
        275                 280                 285

Gln Val Val Ala Glu Gly Asn Asp Gly Gly Gly Gly Ala Gly Arg Pro
    290                 295                 300

Ser Leu Gly Ser Glu Lys Lys Lys Glu Asp Pro Arg Arg Ala Gln Val
305                 310                 315                 320

Pro Pro Thr Arg Glu Ser Arg Val Lys Val Leu Arg Lys Leu Ala Ala

```
                325                 330                 335

Thr Ala Pro Ala Leu Pro Gln Pro Pro Ser Thr Pro Arg Ala Thr Thr
            340                 345                 350

Leu Pro Pro Ala Pro Ala Thr Thr Val Thr Arg Ser Thr Ser Arg Ala
        355                 360                 365

Val Thr Val Ala Ala Arg Pro Met Thr Thr Thr Ala Phe Pro Thr Thr
    370                 375                 380

Gln Arg Pro Trp Thr Pro Ser Pro Ser His Arg Pro Pro Thr Thr Thr
385                 390                 395                 400

Glu Val Ile Thr Ala Arg Arg Pro Ser Val Ser Glu Asn Leu Tyr Pro
                405                 410                 415

Pro Ser Arg Lys Asp Gln His Arg Glu Arg Pro Gln Thr Thr Arg Arg
            420                 425                 430

Pro Ser Lys Ala Thr Ser Leu Glu Ser Phe Thr Asn Ala Pro Pro Thr
        435                 440                 445

Thr Ile Ser Glu Pro Ser Thr Arg Ala Ala Gly Pro Gly Arg Phe Arg
    450                 455                 460

Asp Asn Arg Met Asp Arg Arg Glu His Gly His Arg Asp Pro Asn Val
465                 470                 475                 480

Val Pro Gly Pro Pro Lys Pro Ala Lys Glu Lys Pro Pro Lys Lys Lys
                485                 490                 495

Ala Gln Asp Lys Ile Leu Ser Asn Glu Tyr Glu Glu Lys Tyr Asp Leu
            500                 505                 510

Ser Arg Pro Thr Ala Ser Gln Leu Glu Asp Glu Leu Gln Val Gly Asn
        515                 520                 525

Val Pro Leu Lys Lys Ala Lys Glu Ser Lys Lys His Glu Lys Leu Glu
    530                 535                 540

Lys Pro Glu Lys Lys Lys Glu Lys Lys
545                 550


<210> SEQ ID NO 15
<211> LENGTH: 331
<212> TYPE: PRT
<213> ORGANISM: Homo sapiens

<400> SEQUENCE: 15

Glu Gly Lys Arg Arg Leu Leu Leu Ile Thr Ala Pro Lys Ala Glu Asn
1               5                   10                  15

Asn Met Tyr Val Gln Gln Arg Asp Glu Tyr Leu Glu Ser Phe Cys Lys
            20                  25                  30

Met Ala Thr Arg Lys Ile Ser Val Ile Thr Ile Phe Gly Pro Val Asn
        35                  40                  45

Asn Ser Thr Met Lys Ile Asp His Phe Gln Leu Asp Asn Glu Lys Pro
    50                  55                  60

Met Arg Val Val Asp Asp Glu Asp Leu Val Asp Gln Arg Leu Ile Ser
65                  70                  75                  80

Glu Leu Arg Lys Glu Tyr Gly Met Thr Tyr Asn Asp Phe Phe Met Val
                85                  90                  95

Leu Thr Asp Val Asp Leu Arg Val Lys Gln Tyr Tyr Glu Val Pro Ile
            100                 105                 110

Thr Met Lys Ser Val Phe Asp Leu Ile Asp Thr Phe Gln Ser Arg Ile
        115                 120                 125

Lys Asp Met Glu Lys Gln Lys Lys Glu Gly Ile Val Cys Lys Glu Asp
    130                 135                 140
```

```
Lys Lys Gln Ser Leu Glu Asn Phe Leu Ser Arg Phe Arg Trp Arg Arg
145                 150                 155                 160

Arg Leu Leu Val Ile Ser Ala Pro Asn Asp Glu Asp Trp Ala Tyr Ser
                165                 170                 175

Gln Gln Leu Ser Ala Leu Ser Gly Gln Ala Cys Asn Phe Gly Leu Arg
            180                 185                 190

His Ile Thr Ile Leu Lys Leu Leu Gly Val Gly Glu Glu Val Gly Gly
        195                 200                 205

Val Leu Glu Leu Phe Pro Ile Asn Gly Gly Ser Val Val Glu Arg Glu
    210                 215                 220

Asp Val Pro Ala His Leu Val Lys Asp Ile Arg Asn Tyr Phe Gln Val
225                 230                 235                 240

Ser Pro Glu Tyr Phe Ser Met Leu Leu Val Gly Lys Asp Gly Asn Val
                245                 250                 255

Lys Ser Trp Tyr Pro Ser Pro Met Trp Ser Met Val Ile Val Tyr Asp
            260                 265                 270

Leu Ile Asp Ser Met Gln Leu Arg Arg Gln Glu Met Ala Ile Gln Gln
        275                 280                 285

Ser Leu Gly Met Arg Cys Pro Glu Asp Glu Tyr Ala Gly Tyr Gly Tyr
    290                 295                 300

His Ser Tyr His Gln Gly Tyr Gln Asp Gly Tyr Gln Asp Asp Tyr Arg
305                 310                 315                 320

His His Glu Ser Tyr His His Gly Tyr Pro Tyr
                325                 330


<210> SEQ ID NO 16
<211> LENGTH: 85
<212> TYPE: PRT
<213> ORGANISM: Homo sapiens

<400> SEQUENCE: 16

Met Leu Leu Val Gly Lys Asp Gly Asn Val Lys Ser Trp Tyr Pro Ser
1               5                   10                  15

Pro Met Trp Ser Met Val Ile Val Tyr Asp Leu Ile Asp Ser Met Gln
            20                  25                  30

Leu Arg Arg Gln Glu Met Ala Ile Gln Gln Ser Leu Gly Met Arg Cys
        35                  40                  45

Pro Glu Asp Glu Tyr Ala Gly Tyr Gly Tyr His Ser Tyr His Gln Gly
    50                  55                  60

Tyr Gln Asp Gly Tyr Gln Asp Asp Tyr Arg His His Glu Ser Tyr His
65                  70                  75                  80

His Gly Tyr Pro Tyr
                85


<210> SEQ ID NO 17
<211> LENGTH: 297
<212> TYPE: PRT
<213> ORGANISM: Homo sapiens

<400> SEQUENCE: 17

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45
```

```
Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Ala Pro Thr Val Pro Pro Gln Glu Ala Thr Leu Val Ala Leu Val Ser
    130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
        195                 200                 205

Phe Gln Thr Gln Pro Leu Asn Pro Ile Leu Glu Asp Asp Cys Ser Ser
    210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

Leu Asp Leu Gln Lys Phe Ser Ser Ser Ala Ser Tyr Thr Gly Ala Glu
            260                 265                 270

Thr Leu Gly Gly Asn Thr Val Glu Ser Thr Gly Asp Arg Leu Glu Leu
        275                 280                 285

Asn Val Pro Phe Glu Val Pro Ser Pro
    290                 295


<210> SEQ ID NO 18
<211> LENGTH: 318
<212> TYPE: PRT
<213> ORGANISM: Homo sapiens

<400> SEQUENCE: 18

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125
```

```
Ala Pro Thr Val Pro Pro Gln Glu Ala Thr Leu Val Ala Leu Val Ser
    130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Glu Lys Leu Ile
                165                 170                 175

Ile Phe Ser Asp Pro Val Pro Ala Ser Leu Asn Leu Ile Pro Glu Phe
            180                 185                 190

Ala Gly Gly Leu Leu Gln Phe Glu Ala Asp Lys Thr Ala Lys Glu Glu
        195                 200                 205

Ser Leu Phe Pro Val Pro Pro Ser Lys Glu Thr Ser Ala Glu Ser Gln
    210                 215                 220

Val Ser Glu Asn Ile Phe Gln Thr Gln Pro Leu Asn Pro Ile Leu Glu
225                 230                 235                 240

Asp Asp Cys Ser Ser Thr Ser Gly Phe Pro Thr Gln Glu Ser Phe Thr
                245                 250                 255

Met Ala Ser Cys Thr Ser Glu Ser His Ser His Trp Val His Ser Pro
            260                 265                 270

Ile Glu Cys Thr Glu Leu Asp Leu Gln Lys Phe Ser Ser Ser Ala Ser
        275                 280                 285

Tyr Thr Gly Ala Glu Thr Leu Gly Gly Asn Thr Val Glu Ser Thr Gly
    290                 295                 300

Asp Arg Leu Glu Leu Asn Val Pro Phe Glu Val Pro Ser Pro
305                 310                 315


<210> SEQ ID NO 19
<211> LENGTH: 173
<212> TYPE: PRT
<213> ORGANISM: Homo sapiens

<400> SEQUENCE: 19

Met Ser Thr Gly Thr Asn Gly Asp Gly Val Ser Pro Ala Asn Gly Val
1               5                   10                  15

Val Leu Asp Arg Ser Tyr Pro Arg Cys Leu Pro Val Glu Leu Ser Gly
            20                  25                  30

Gly Arg Tyr Thr His Ser Ala Pro Ser Gly Gly His Thr Cys Cys Thr
        35                  40                  45

Gly Gly Leu Leu Gln Phe Glu Ala Asp Lys Thr Ala Lys Glu Glu Ser
    50                  55                  60

Leu Phe Pro Val Pro Pro Ser Lys Glu Thr Ser Ala Glu Ser Gln Val
65                  70                  75                  80

Ser Glu Asn Ile Phe Gln Thr Gln Pro Leu Asn Pro Ile Leu Glu Asp
                85                  90                  95

Asp Cys Ser Ser Thr Ser Gly Phe Pro Thr Gln Glu Ser Phe Thr Met
            100                 105                 110

Ala Ser Cys Thr Ser Glu Ser His Ser His Trp Val His Ser Pro Ile
        115                 120                 125

Glu Cys Thr Glu Leu Asp Leu Gln Lys Phe Ser Ser Ser Ala Ser Tyr
    130                 135                 140

Thr Gly Ala Glu Thr Leu Gly Gly Asn Thr Val Glu Ser Thr Gly Asp
145                 150                 155                 160

Arg Leu Glu Leu Asn Val Pro Phe Glu Val Pro Ser Pro
                165                 170
```

<210> SEQ ID NO 20
<211> LENGTH: 265
<212> TYPE: PRT
<213> ORGANISM: Homo sapiens

<400> SEQUENCE: 20

```
Met Ser Thr Gly Thr Asn Gly Asp Gly Val Ser Pro Ala Asn Gly Val
1               5                   10                  15

Val Leu Asp Arg Ser Tyr Pro Arg Ile Val Val Met Glu Arg Val Glu
            20                  25                  30

Met Pro Thr Ala Gln Pro Ala Leu Leu Ala Gly Thr Lys Ala Ala Gly
        35                  40                  45

Ala Thr Thr Asp Val Arg Val Ala Ser Pro Val Leu Ser Ser Ile Val
    50                  55                  60

Phe Arg Arg Ser Thr Ala Gln Leu Pro Leu Met Leu Ser Val Gly Thr
65                  70                  75                  80

Val Cys Pro Gly Ala Phe Gln Leu Ser Leu Val Glu Ala Asp Thr Pro
                85                  90                  95

Thr Val Pro Pro Gln Glu Ala Thr Leu Val Ala Leu Val Ser Ser Leu
            100                 105                 110

Leu Val Val Phe Thr Leu Ala Phe Leu Gly Leu Phe Phe Leu Tyr Cys
        115                 120                 125

Lys Gln Phe Phe Asn Arg His Cys Gln Arg Val Ala Gly Gly Leu Leu
    130                 135                 140

Gln Phe Glu Ala Asp Lys Thr Ala Lys Glu Glu Ser Leu Phe Pro Val
145                 150                 155                 160

Pro Pro Ser Lys Glu Thr Ser Ala Glu Ser Gln Val Ser Glu Asn Ile
                165                 170                 175

Phe Gln Thr Gln Pro Leu Asn Pro Ile Leu Glu Asp Asp Cys Ser Ser
            180                 185                 190

Thr Ser Gly Phe Pro Thr Gln Glu Ser Phe Thr Met Ala Ser Cys Thr
        195                 200                 205

Ser Glu Ser His Ser His Trp Val His Ser Pro Ile Glu Cys Thr Glu
    210                 215                 220

Leu Asp Leu Gln Lys Phe Ser Ser Ser Ala Ser Tyr Thr Gly Ala Glu
225                 230                 235                 240

Thr Leu Gly Gly Asn Thr Val Glu Ser Thr Gly Asp Arg Leu Glu Leu
                245                 250                 255

Asn Val Pro Phe Glu Val Pro Ser Pro
            260                 265
```

<210> SEQ ID NO 21
<211> LENGTH: 107
<212> TYPE: PRT
<213> ORGANISM: Homo sapiens

<400> SEQUENCE: 21

```
Met Ser Thr Gly Thr Asn Gly Asp Gly Val Ser Pro Ala Asn Gly Val
1               5                   10                  15

Val Leu Asp Arg Ser Tyr Pro Arg Cys Leu Pro Val Glu Leu Ser Gly
            20                  25                  30

Gly Arg Tyr Thr His Ser Ala Pro Ser Gly Gly His Thr Cys Cys Thr
        35                  40                  45

Gly Gly Leu Leu Gln Phe Glu Ala Asp Lys Thr Ala Lys Glu Glu Ser
    50                  55                  60

Leu Phe Pro Val Pro Pro Ser Lys Glu Thr Ser Ala Glu Ser Gln Val
```

```
65                  70                  75                  80

Ser Trp Ala Pro Gly Ser Leu Ala Gln Leu Phe Ser Leu Asp Ser Val
                85                  90                  95

Pro Ile Pro Gln Gln Gln Gln Gly Pro Glu Met
            100                 105


<210> SEQ ID NO 22
<211> LENGTH: 134
<212> TYPE: PRT
<213> ORGANISM: Homo sapiens

<400> SEQUENCE: 22

Met Gly Thr Val Cys His Leu Pro Thr Val Trp Ser Trp Thr Gly Ala
1               5                   10                  15

Ile Gln Gly Ala Phe Gln Leu Ser Leu Val Glu Ala Asp Thr Pro Thr
            20                  25                  30

Val Pro Pro Gln Glu Ala Thr Leu Val Ala Leu Val Ser Ser Leu Leu
        35                  40                  45

Val Val Phe Thr Leu Ala Phe Leu Gly Leu Phe Phe Leu Tyr Cys Lys
    50                  55                  60

Gln Phe Phe Asn Arg His Cys Gln Arg Val Ala Gly Gly Leu Leu Gln
65                  70                  75                  80

Phe Glu Ala Asp Lys Thr Ala Lys Glu Glu Ser Leu Phe Pro Val Pro
                85                  90                  95

Pro Ser Lys Glu Thr Ser Ala Glu Ser Gln Val Ser Trp Ala Pro Gly
            100                 105                 110

Ser Leu Ala Gln Leu Phe Ser Leu Asp Ser Val Pro Ile Pro Gln Gln
        115                 120                 125

Gln Gln Gly Pro Glu Met
    130


<210> SEQ ID NO 23
<211> LENGTH: 132
<212> TYPE: PRT
<213> ORGANISM: Homo sapiens

<400> SEQUENCE: 23

Met Gly Thr Val Cys His Leu Pro Thr Val Trp Ser Trp Thr Gly Ala
1               5                   10                  15

Ile Gln Gly Ala Phe Gln Leu Ser Leu Val Glu Ala Asp Thr Pro Thr
            20                  25                  30

Val Pro Pro Gln Glu Ala Thr Leu Val Ala Leu Val Ser Ser Leu Leu
        35                  40                  45

Val Val Phe Thr Leu Ala Phe Leu Gly Leu Phe Phe Leu Tyr Cys Lys
    50                  55                  60

Gln Phe Phe Asn Arg His Cys Gln Arg Gly Gly Leu Leu Gln Phe Glu
65                  70                  75                  80

Ala Asp Lys Thr Ala Lys Glu Glu Ser Leu Phe Pro Val Pro Pro Ser
                85                  90                  95

Lys Glu Thr Ser Ala Glu Ser Gln Val Ser Trp Ala Pro Gly Ser Leu
            100                 105                 110

Ala Gln Leu Phe Ser Leu Asp Ser Val Pro Ile Pro Gln Gln Gln Gln
        115                 120                 125

Gly Pro Glu Met
    130
```

```
<210> SEQ ID NO 24
<211> LENGTH: 299
<212> TYPE: PRT
<213> ORGANISM: Homo sapiens

<400> SEQUENCE: 24

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Thr Pro Thr Val Pro Pro Gln Glu Ala Thr Leu Val Ala Leu Val Ser
    130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Val Ala Gly Gly
                165                 170                 175

Leu Leu Gln Phe Glu Ala Asp Lys Thr Ala Lys Glu Glu Ser Leu Phe
            180                 185                 190

Pro Val Pro Pro Ser Lys Glu Thr Ser Ala Glu Ser Gln Val Ser Glu
        195                 200                 205

Asn Ile Phe Gln Thr Gln Pro Leu Asn Pro Ile Leu Glu Asp Asp Cys
    210                 215                 220

Ser Ser Thr Ser Gly Phe Pro Thr Gln Glu Ser Phe Thr Met Ala Ser
225                 230                 235                 240

Cys Thr Ser Glu Ser His Ser His Trp Val His Ser Pro Ile Glu Cys
                245                 250                 255

Thr Glu Leu Asp Leu Gln Lys Phe Ser Ser Ser Ala Ser Tyr Thr Gly
            260                 265                 270

Ala Glu Thr Leu Gly Gly Asn Thr Val Glu Ser Thr Gly Asp Arg Leu
        275                 280                 285

Glu Leu Asn Val Pro Phe Glu Val Pro Ser Pro
    290                 295


<210> SEQ ID NO 25
<211> LENGTH: 297
<212> TYPE: PRT
<213> ORGANISM: Homo sapiens

<400> SEQUENCE: 25

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
```

```
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Thr Pro Thr Val Pro Pro Gln Glu Ala Thr Leu Val Ala Leu Val Ser
    130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
        195                 200                 205

Phe Gln Thr Gln Pro Leu Asn Pro Ile Leu Glu Asp Asp Cys Ser Ser
    210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

Leu Asp Leu Gln Lys Phe Ser Ser Ser Ala Ser Tyr Thr Gly Ala Glu
            260                 265                 270

Thr Leu Gly Gly Asn Thr Val Glu Ser Thr Gly Asp Arg Leu Glu Leu
        275                 280                 285

Asn Val Pro Phe Glu Val Pro Ser Pro
    290                 295


<210> SEQ ID NO 26
<211> LENGTH: 134
<212> TYPE: PRT
<213> ORGANISM: Homo sapiens

<400> SEQUENCE: 26

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110
```

-continued

```
Phe Gly Arg Lys Met Asp Arg Ile Ser Ser Ser Ser Gly Leu Gly Cys
        115                 120                 125

Lys Val Leu Arg Arg His
    130
```

NEUROFILAMENT LIGHT CHAIN (NFL) AS A BIOMARKER FOR TRANSTHYRETIN AMYLOIDOSIS POLYNEUROPATHY

RELATED APPLICATIONS

This application is a 35 § U.S.C. 111 (a) continuation application which claims the benefit of priority to PCT/US2020/048509, filed on Aug. 28, 2000, which claims the benefit of priority to U.S. Provisional Application No. 63/044,163, filed on Jun. 25, 2020, U.S. Provisional Patent Application No. 62/925,623, filed on Oct. 24, 2019, and U.S. Provisional Patent Application No. 62/894,237, filed on Aug. 30, 2019. The entire contents of each of the foregoing applications is incorporated herein by reference.

SEQUENCE LISTING

The instant application contains a Sequence Listing which has been submitted electronically in ASCII format and is hereby incorporated by reference in its entirety. Said ASCII copy, created on Feb. 3, 2022, is named 121301_18604_SL.txt and is 43,442 bytes in size.

BACKGROUND

Hereditary transthyretin amyloidosis is an autosomal dominant, multisystemic, progressive, life-threatening disease caused by mutations in the gene encoding transthyretin (TTR). The liver is the primary source of circulating tetrameric transthyretin protein. In hereditary transthyretin amyloidosis, both mutant and wild-type transthyretin deposit as amyloid in peripheral nerves and the heart, kidney, and gastrointestinal tract, resulting in polyneuropathy and cardiomyopathy. Neuropathic changes result in profound sensorimotor disturbances, with deterioration in activities of daily living and ambulation. Autonomic nerve involvement causes hypotension, diarrhea, impotence, and bladder disturbances. Cardiac manifestations include heart failure, arrhythmias, orthostatic hypotension, or sudden death due to severe conduction disorders. Hereditary transthyretin amyloidosis is inexorably progressive, with survival of 2 to 15 years after the onset of neuropathy, but only 2 to 5 years among patients presenting with cardiomyopathy (Adams et al., N Engl J Med 2018; 379:11-21). Cardiac dysfunction is also observed in the context of wild type TTR amyloidosis. Although the main pathologic manifestation of hereditary TTR amyloidosis is a progressive ascending polyneuropathy or cardiomyopathy, mixed phenotypes, extreme phenotypic variability, and incomplete penetrance often obscure a proper diagnosis for physicians not considering TTR amyloidosis. As a consequence, hereditary TTR amyloidosis is under-recognized and often misdiagnosed (Coelho et al., Neurol Ther. 2016, 5:1-25).

Mechanisms of action for therapeutic agents for the treatment of TTR amyloidosis can be generally divided into two categories, agents that stabilize TTR thereby preventing the formation of TTR amyloid plaques; and agents that inhibit the expression of TTR. Therapeutic agents that work by each of the different mechanisms have been approved by various regulatory agencies and are discussed below.

Tafamidis (PFIZER®), a TTR stabilizer, was demonstrated to reduce cardiomyopathy in individuals with TTR amyloidosis in a pivotal Phase 3 Transthyretin Amyloidosis Cardiomyopathy Clinical Trial (ATTR-ACT), a double-blind, randomized, placebo-controlled clinical study to investigate a pharmacological therapy for the treatment of this disease (Maurer et al., NEJM. 2018; 379:1007-1016). In ATTR-ACT, tafamidis significantly reduced the hierarchical combination of all-cause mortality and frequency of cardiovascular-related hospitalizations compared to placebo over a 30-month period (p=0.0006). Additionally, individual components of the primary analysis demonstrated a relative reduction in the risk of all-cause mortality and frequency of cardiovascular-related hospitalization of 30% (p=0.026) and 32% (p<0.0001), respectively, with tafamidis versus placebo. Approximately 80% of total deaths were cardiovascular-related in both treatment groups. Data were pooled for hereditary TTR amyloidosis and wild type amyloidosis. Tafamidis is approved by the US FDA for the treatment of the cardiomyopathy of wild-type or hereditary transthyretin-mediated amyloidosis (ATTR-CM) to reduce death and hospitalization related to heart problems.

In the pivotal Fx-005 clinical trial, the efficacy and safety of tafamidis was evaluated in an 18-month, randomized, double-blind, placebo-controlled trial involving 128 patients with transthyretin familial amyloid polyneuropathy (TTR-FAP) with the V30M mutation and primarily stage 1 disease, the earliest stage of the three stages of TTR-FAP. The primary outcome measures were the Neuropathy Impairment Score of the Lower Limb (NIS-LL; a physician assessment of the neurological exam of the lower limbs) and the Norfolk Quality of Life Diabetic Neuropathy score (a patient-reported outcome that uses a total quality of life (TQOL) score). Secondary outcome measures included composite scores of large nerve fiber and small nerve fiber function, and nutritional assessments using the modified body mass index (mBMI; BMI multiplied by serum albumin in g per 1) (Said et al., Nature Drug Disc. 2012. 11:185-186). No differences were observed between the tafamidis and placebo groups for the coprimary endpoints, NIS-LL responder analysis (45.3% vs 29.5% responders; p=0.068) and change in TQOL (2.0 vs 7.2; p=0.116) in the intent to treat (ITT) population. In the efficacy-evaluable (EE) population, significantly more tafamidis patients than placebo patients were NIS-LL responders (60.0% vs 38.1%; p=0.041), and tafamidis patients had better-preserved TQOL (0.1 vs 8.9; p=0.045). Significant differences in most secondary endpoints favored tafamidis. TTR was stabilized in 98% of tafamidis and 0% of placebo patients (p<0.0001) (Coelho et al., Neurology. 2012; 79:785-792). Coelho et al. (2012) characterized the study as providing class II evidence that 20 mg tafamidis QD was associated with no difference in clinical progression in patients with TTR-FAP, as measured by the NIS-LL and the Norfolk QOL-DN score. Secondary outcomes demonstrated a significant delay in peripheral neurologic impairment with tafamidis, which was well tolerated over 18 months.

Tafamidis was approved by the European Commission in 2011 for the treatment of TTR amyloidosis in adult patients with stage 1 symptomatic polyneuropathy to delay peripheral neurological impairment (www.ema.europa.eu/en/documents/product-information/vyndaqel-epar-product-information_en.pdf). However, the FDA Peripheral and Central Nervous System Drugs Advisory Committee voted 13-4 that the data did not show substantial evidence of efficacy on a clinical endpoint. The panel also voted 13-4 that the data provide substantial evidence of efficacy for a surrogate endpoint that is reasonably likely to predict a clinical benefit. (www.pharmatimes.com/news/fda_rejects_pfizer_rare_disease_drug_tafamidis_977149). Tafamidis was not approved for treatment of TTR-FAP by the FDA.

Diflunisal, a non-steroidal anti-inflammatory drug (NSAID), which is indicated for acute or long-term use for symptomatic treatment of mild to moderate pain, osteoarthritis, and rheumatoid arthritis (DOLOBID® (diflusinal) package insert, Merck & Co., Inc.), has been shown to act as a TTR stabilizer and studies have suggested that the agent has potential for clinical stabilization of disease progression in TTR-CA (see, e.g., Rosenblum et al., Circ Heart Fail. 2018; 11: e004769). Off-label use of diflusinal for the treatment of TTR-FAP has been reported (Azorín Contesse et al., Orphanet J Rare Dis. 2015; 10(Suppl 1): P2).

Patisiran is a transthyretin-directed small interfering RNA and is indicated for the treatment of the polyneuropathy of hereditary transthyretin-mediated amyloidosis in adults (ONPATTRO® (patisiran) package insert, Alnylam Pharmaceuticals, Inc.). In the APOLLO phase 3, double blind, placebo-controlled clinical trial, a total of 225 patients underwent randomization (148 to the patisiran group and 77 to the placebo group). Overall, 126 patients (56%) were included in the predefined cardiac subpopulation, with a higher percentage in the patisiran group (61%, as compared with 47% in the placebo group). The mean (±SD) mNIS±7 at baseline was 80.9±41.5 in the patisiran group and 74.6±37.0 in the placebo group; the least-squares mean (±SE) change from baseline was-6.0±1.7 versus 28.0±2.6 (difference, −34.0 points; P<0.001) at 18 months. The mean (±SD) baseline Norfolk QOL-DN score was 59.6±28.2 in the patisiran group and 55.5±24.3 in the placebo group; the least-squares mean (±SE) change from baseline was −6.7±1.8 versus 14.4±2.7 (difference, −21.1 points; P<0.001) at 18 months. Patisiran also showed an effect on gait speed and modified BMI. At 18 months, the least-squares mean change from baseline in gait speed was 0.08±0.02 m per second with patisiran versus −0.24±0.04 m per second with placebo (difference, 0.31 m per second; P<0.001), and the least-squares mean change from baseline in the modified BMI was −3.7±9.6 versus −119.4±14.5 (difference, 115.7; P<0.001). Exploratory endpoints included measures of cardiac structure and function. In the cardiac subpopulation, the geometric mean baseline level of NT-proBNP, a measure of cardiac stress that is an independent predictor of death in patients with transthyretin cardiac amyloidosis, was 726.9 µg per milliliter (coefficient of variation, 220.3%) in the patisiran group and 711.1 µg per milliliter (coefficient of variation, 190.8%) in the placebo group. At 18 months, the adjusted geometric mean ratio to baseline was 0.89 with patisiran and 1.97 with placebo (ratio, 0.45; P<0.001), representing a 55% difference in favor of patisiran. Patisiran treatment was also associated with better cardiac structure and function than placebo, including significant differences in mean left ventricular wall thickness (P=0.02) and longitudinal strain (P=0.02) at 18 months. Approximately 20% of the patients who received patisiran and 10% of those who received placebo had mild or moderate infusion-related reactions; the overall incidence and types of adverse events were similar in the two groups. In the trial, patisiran improved multiple clinical manifestations of hereditary transthyretin amyloidosis (Adams et al., N Engl J Med 2018; 379:11-21).

In an analysis performed on the cardiac subpopulation of the APOLLO study (n=126; 56% of total population), patisiran reduced mean LV wall thickness (least-squares mean difference±SEM: −0.9±0.4 mm, P=0.017), interventricular septal wall thickness, posterior wall thickness, and relative wall thickness at Month 18, compared with placebo. Patisiran also led to increased end-diastolic volume (8.3±3.9 mL, P=0.036), decreased global longitudinal strain (−1.4±0.6%, P=0.015), and increased cardiac output (0.38±0.19 L/min, P=0.044) compared with placebo at Month 18. Patisiran lowered NTproBNP at 9 and 18 months (at 18 months, ratio of fold-change patisiran/placebo 0.45, P<0.001). A consistent effect on NT-proBNP at 18 months was observed in the overall APOLLO patient population (n=225). Median follow-up duration was 18.7 months. The exposure-adjusted rates of cardiac hospitalizations or all-cause death were 18.7 and 10.1 per 100 patient-years in the placebo and patisiran groups, respectively (Andersen-Gill hazard ratio 0.54, 95% confidence interval: 0.28-1.01) (Solomon et al., Circulation. 2019 Jan. 22; 139 (4): 431-443). Solomon et al. concluded that patisiran decreased mean LV wall thickness, global longitudinal strain, NTproBNP, and adverse cardiac outcomes compared with placebo at Month 18, suggesting that patisiran may halt or reverse the progression of the cardiac manifestations of hATTR amyloidosis and may provide benefit to patients with the cardiac manifestations of hATTR amyloidosis.

Inotersen is a transthyretin-directed antisense oligonucleotide approved for treatment of the polyneuropathy of hereditary transthyretin-mediated amyloidosis in adults (TEGSEDI™ (inotersen) package insert, IONIS PHARMACEUTICALS®). The efficacy of inotersen was demonstrated in a randomized, double-blind, placebo-controlled, multicenter clinical trial in adult patients with polyneuropathy caused by hATTR amyloidosis (Study 1; NCT 01737398). Patients were randomized in a 2:1 ratio to receive either 284 mg inotersen (N=113) or placebo (N=60), respectively, as a subcutaneous injection administered once per week for 65 weeks (3 doses were administered during the first week of treatment). Seventy seven percent of inotersen-treated patients and 87% of patients on placebo completed 66 weeks of the assigned treatment. The co-primary efficacy endpoints were the change from baseline to Week 66 in the modified Neuropathy Impairment Scale+7 (mNIS+7) composite score and the Norfolk Quality of Life Diabetic Neuropathy (QoL-DN) total score. Both primary efficacy assessments favored inotersen: the difference in the least-squares mean change from baseline to week 66 between the two groups (inotersen minus placebo) was −19.7 points (95% confidence interval [CI], −26.4 to −13.0; P<0.001) for the mNIS+7 and −11.7 points (95% CI, −18.3 to −5.1; P<0.001) for the Norfolk QOL-DN score. These improvements were independent of disease stage, mutation type, or the presence of cardiomyopathy. There were five deaths in the inotersen group and none in the placebo group. The most frequent serious adverse events in the inotersen group were glomerulonephritis (in 3 patients [3%]) and thrombocytopenia (in 3 patients [3%]), with one death associated with one of the cases of grade 4 thrombocytopenia. Thereafter, all patients received enhanced monitoring (Benson et al., N Engl J Med 2018; 379:22-31).

SUMMARY OF THE INVENTION

In some aspects, the present disclosure provides a method of treating a human subject having transthyretin (TTR) amyloidosis (e.g., cardiovascular TTR amyloidosis or TTR amyloidosis polyneuropathy) comprising, responsive to a determination of an elevated neurofilament light chain (NfL) level in a subject relative to a reference level, administering to the subject a TTR amyloidosis therapeutic agent (e.g., a therapeutic agent that reduces expression of TTR or a therapeutic agent that stabilizes TTR), thereby treating the subject.

In some aspects, the present disclosure provides a method of treating a human subject having, or at risk of having TTR amyloidosis (e.g., cardiovascular TTR amyloidosis or TTR amyloidosis polyneuropathy) comprising:

obtaining or having obtained a biological sample from the subject, performing or having performed an assay to determine the level of NfL in the biological sample, and, if the subject has an elevated level of NfL relative to a reference value, administering to the subject a TTR amyloidosis therapeutic agent (e.g., a therapeutic agent that reduces expression of TTR or a therapeutic agent that stabilizes TTR).

In some aspects, the present disclosure provides a method of treating a human subject having, or at risk of having, TTR amyloidosis (e.g., cardiovascular TTR amyloidosis or TTR amyloidosis polyneuropathy), comprising: (a) providing a TTR amyloidosis therapeutic agent (e.g., a therapeutic agent that reduces expression of TTR or a therapeutic agent that stabilizes TTR), (b) detecting an elevated level of NfL in the subject relative to a reference level, and (c) administering the therapeutic agent to the subject if the level of neurofilament is greater than the reference level.

In some aspects, the present disclosure provides a method of treating a subject having, or at risk of having, TTR amyloidosis, comprising: responsive to a determination of an elevated level of NfL relative to a reference value (e.g., a healthy control value) in the subject, performing one, two, or all of: (a) administering a TTR amyloidosis therapeutic agent, e.g., an agent that reduces expression of TTR; (b) discontinuing treatment of a subject with a therapeutic agent that stabilizes TTR; or (c) administering an agent that reduces expression of TTR; thereby treating TTR amyloidosis in the subject.

In some aspects, the disclosure provides a method of determining whether treatment with a therapeutic agent that inhibits expression of TTR should be initiated in a subject having a TTR mutation associated with TTR amyloidosis, comprising (a) determining the level of NfL in a sample from the subject; (b) comparing the level of NfL determined in step (a) to a reference level of NfL; and (c) if the level of NfL determined in step (a) is greater than the reference level, determining that treatment with the therapeutic agent should be initiated in the subject.

In some aspects, the disclosure provides a therapeutic agent that reduces expression of TTR for use in treating a human subject with cardiovascular TTR amyloidosis wherein the subject has an elevated NfL level as compared to a reference level.

In some aspects, the disclosure provides a therapeutic agent that reduces expression of TTR for use in a method of treatment of a human subject with cardiovascular TTR amyloidosis wherein the method comprises the step of determining if a patient has an elevated NfL level as compared to a reference level of NfL.

In some aspects, the disclosure provides a method of treating a subject having asymptomatic TTR amyloidosis (e.g., wherein the subject is an asymptomatic carrier of a mutation associated with TTR amyloidosis, or is presymptomatic), comprising administering to the subject a therapeutic agent that reduces expression of expression of TTR (e.g., a nucleic acid therapeutic agent), wherein the subject has, or is identified as having, an elevated level of NfL relative to a reference value.

In some aspects, the disclosure provides a method of treating a subject having or at risk of having TTR amyloidosis, wherein the subject does not have a neuropathy, e.g., polyneuropathy, comprising administering to the subject a therapeutic agent that reduces expression of expression of TTR (e.g., a nucleic acid therapeutic agent), wherein the subject has, or is identified as having, an elevated level of NfL relative to a reference value.

In some aspects, the disclosure provides a method of treating a subject having or at risk of having TTR amyloidosis, wherein the subject is FAP Stage 0, comprising administering to the subject a therapeutic agent that reduces expression of expression of TTR (e.g., a nucleic acid therapeutic agent), wherein the subject has, or is identified as having, an elevated level of NfL relative to a reference value.

In some aspects, the disclosure provides a method of treating a subject having or at risk of having TTR amyloidosis, wherein the subject does not have a mutation associated with TTR amyloidosis, comprising administering to the subject a therapeutic agent that reduces expression of expression of TTR (e.g., a nucleic acid therapeutic agent), wherein the subject has, or is identified as having, an elevated level of NfL relative to a reference value.

In some aspects, the disclosure provides a reaction mixture comprising (a) a biological sample from a subject having, or at risk of having, TTR amyloidosis; and (b) a reagent (e.g., an antibody or antigen-binding fragment thereof) for NfL detection.

In some aspects, the disclosure provides a method of detecting NfL level in a biological sample, comprising (a) providing a biological sample from a subject having TTR amyloidosis or who is an asymptomatic or presymptomatic carrier of TTR amyloidosis; and (b) contacting the biological sample with a detectable reagent (e.g., an antibody or antigen-binding fragment thereof) under conditions that allow NfL detection.

In some aspects, the disclosure provides an in vitro method of diagnosing TTR amyloidosis polyneuropathy in a subject, the method comprising: (a) determining the level of NfL in a sample from the subject; (b) comparing the level of NfL determined in step (a) to a reference level of NfL; and (c) assessing whether the subject suffers from TTR amyloidosis polyneuropathy, wherein an increase in the level of NfL determined in step (a) as compared to the reference level of NfL is indicative of the subject suffering from TTR amyloidosis polyneuropathy.

In some aspects, the disclosure provides a therapeutic agent that reduces expression of TTR for use in the treatment of TTR amyloidosis polyneuropathy in a subject that has been identified as suffering from TTR amyloidosis polyneuropathy using a method described herein.

In some aspects, the disclosure provides a therapeutic agent that reduces expression of TTR for use in a method of treating TTR amyloidosis polyneuropathy, the method comprising: (a) determining the level of NfL in a sample from the subject; (b) comparing the level of NfL determined in step (a) to a reference level of NfL; (c) assessing whether the subject suffers from TTR amyloidosis polyneuropathy, wherein an increase in the level of NfL determined in step (a) as compared to the reference level of NfL is indicative of the subject suffering from TTR amyloidosis polyneuropathy; and (d) administering the therapeutic agent that reduces expression of TTR to a subject that has been identified in step (c) as suffering from TTR amyloidosis polyneuropathy.

In some aspects, the present disclosure provides a method of treating a human subject having transthyretin (TTR) amyloidosis comprising, responsive to a determination of an altered level of one or more (e.g., at least 2, 3, 4, 5, 6, 7, 8, 9, or 10) biomarkers described herein (e.g., in Table 2 herein) in a subject relative to a reference level, administering to the subject a TTR amyloidosis therapeutic agent, thereby treating the subject. In some embodiments, the subject has an increase in the level of one or more proteins having a positive beta coefficient relative to a reference level indicative of progression of TTR amyloidosis, or the subject has a decrease in the level of one or more proteins having a negative beta coefficient relative to a reference level.

Each of the aspects above may be combined, e.g., with any of the embodiments below.

In some embodiments, the therapeutic agent that reduces the expression of TTR is a nucleic acid therapeutic. In some embodiments, the nucleic acid therapeutic is an RNAi agent or an antisense oligonucleotide. In some embodiments, the nucleic acid therapeutic is selected from patisiran, vutrisiran, inotersen and ION-TTR-LRx.

In some embodiments, the subject has not been diagnosed with hTTR amyloidosis polyneuropathy. In some embodiments, the subject has not been diagnosed as having a neuropathy. In some embodiments, the subject does not meet the diagnostic criteria for Stage 1 familial amyloid polyneuropathy (FAP). In some embodiments, the subject is FAP Stage 0. In some embodiments, the subject does not have polyneuropathy. In some embodiments, the subject has a TTR mutation associated with TTR amyloidosis. In some embodiments, the subject does not have a mutation associated with TTR amyloidosis.

In some embodiments, the subject has an altered level of one or more of (e.g., at least 2, 3, 4, 5, 6, 7, 8, 9, or 10 of) the proteins listed in Table 2 as compared to a reference level wherein the subject has an increase in the level of a protein having a positive beta coefficient relative to a reference level indicative of progression of TTR amyloidosis, or wherein a subject has a decrease in the level of a protein having a negative beta coefficient relative to a reference level indicative of progression of TTR amyloidosis. In some embodiments, the protein listed in Table 2 is selected from RSPO3, CCDC80, EDA2R, NT-proBNP, and N-CDase as compared to a reference level. In some embodiments, the subject also has an elevated level of one or more of the proteins listed in Table 2 as compared to a reference level. In some embodiments, the subject has an elevated level of one or more of RSPO3, CCDC80, EDA2R, and NT-proBNP as compared to a reference level. In some embodiments, the subject has a decreased level of N-CDase as compared to a reference level. In some embodiments, the reference level is a healthy control level or to an earlier level in the same subject. In some embodiments, the reference level of NfL is from 30-50 μg/ml in plasma, e.g., 35-40 μg/ml in plasma, e.g., about 37 μg/ml in plasma.

In some embodiments, the subject is being treated with a therapeutic agent that stabilizes TTR. In some embodiments, the agent that stabilizes a TTR is tafamidis or diflunisal. In some embodiments, the method further comprising discontinuation of treatment with the therapeutic agent go stabilize TTR when the subject has an elevated level of NfL.

In some embodiments, the level is determined in a subject sample selected from blood, plasma, or serum. In some embodiments, the level (e.g., level in plasma) is measured 9, 18 or 30 months after the start of treatment.

In some embodiments, the subject is further suffering from one or more of orthostatic hypotension, diarrhea, constipation, erectile dysfunction, glaucoma, intravitreal deposition, scalloped pupils; carpal tunnel syndrome, lumbar spinal stenosis, and bicep tendon rupture, indicative of TTR amyloidosis polyneuropathy.

In some embodiments, the method further comprises monitoring NfL levels after initiation of treatment with a TTR amyloidosis therapeutic agent (e.g., a therapeutic agent that reduces expression of TTR or a therapeutic agent that stabilizes TTR). In some embodiments, a decrease in NfL levels indicates that the TTR amyloidosis therapeutic agent was effective, e.g., that the therapeutic agent that reduces expression of TTR reduced TTR levels. In some embodiments, the method further comprising monitoring the subject for development of one or more symptoms of TTR amyloidosis, e.g., one or more symptoms of neurological manifestations of TTR amyloidosis. In some embodiments, the subject has a mutation in TTR, e.g., a mutation at V122 of TTR, e.g., a V122I mutation.

In some embodiments, the subject has, or has been diagnosed with, cardiovascular TTR amyloidosis.

In some embodiments, the method further comprises assessing if the subject also has an altered level of one or more of the proteins listed in Table 2 as compared to a reference level, wherein the subject has an increase in the level of a protein having a positive beta coefficient relative to a reference level, or wherein a subject has a decrease in the level of a protein having a negative beta coefficient relative to a reference level.

BRIEF DESCRIPTION OF THE FIGURES

(FIG. 2A) A subset of the measured proteins was used to project the differences between disease patients and healthy controls at baseline onto two principal components (PC1 and PC2) that most explained the difference in the data sets. Graph legend of (FIG. 2A), from top: Normal Healthy; Baseline Apollo (indicating all Apollo patients at baseline). Analysis of placebo treated patients at month 18 (FIG. 2B) and patisiran treated patients at month 18 (FIG. 2C) is shown in the same PC1 and PC2 space. Graph legend of (FIG. 2B), from top: Normal Healthy; Baseline Apollo; Month 18 Placebo. Graph legend of (FIG. 2C), from top: Normal Healthy; Month 18 Placebo; Month 18 Patisiran. (FIG. 2D) Illustrative diagram depicting v1 and v2 as well as ϕ and ⊖. For each patient, a vector (v1) from the mean healthy patient to baseline and a second vector (v2) from baseline to Month 18 were used to compute two metrics, one for the ratio of the magnitude of v2 compared to v1 denoted as ϕ, and ⊖ as the angle between the two vectors. Here ϕ measures the rate of disease progression or regression and ⊖ measures the directionality of the proteome (defined by whether the proteome moves away or towards the healthy controls). Graph legend of (FIG. 2D), from top: Placebo; Patisiran. (FIG. 2E) Individual patient trajectories are shown, separated by whether they were on placebo or patisiran treatment. Graph legend of (FIG. 2E), from top: Placebo; Patisiran.

(FIG. 3A) Levels of NfL in healthy controls and placebo or patisiran treated patients at baseline (no significant difference), 9 months ($p<0.001$) or 18 months ($p<0.001$). Trajectories of individual patients on placebo (FIG. 3B) or patisiran (FIG. 3C) over time, coded by their corresponding change in mNIS+7 (from baseline to month 18). The graphs in the top row show all changes in mNIS for the placebo (FIG. 3B) or patisiran (FIG. 3C) groups; the graphs in the middle row show only the mNIS+7 change >25 for the placebo (FIG. 3B) or patisiran (FIG. 3C) groups; and the bottom row of graphs shows the mNIS+7 change <=−25 for the placebo group (FIG. 3B) or the mNIS+7 change <=−25, −25<mNIS+7 change <=−10, or −10<mNIS+7 change <=0 for the patisiran group (FIG. 3C). (FIG. 3D) Correlation between change in NfL levels from baseline to 18 months and the corresponding change in mNIS+7 coded by treatment.

(FIG. 4A) Correlation between Olink and Quanterix Simoa platform is 0.96. (FIG. 4B) Levels of NfL in healthy controls and placebo- or patisiran-treated patients at baseline, or 18 months. (FIG. 4C) Correlation between change in NfL levels from baseline to 18 months and the corresponding change in mNIS+7 coded by treatment. (FIG. 4D) Receiver operator curve for the ability of NfL plasma levels to distinguish between healthy patients and patients with hATTR amyloidosis with polyneuropathy. The area under the curve is 0.956. (FIG. 4E) Histograms showing the distributions of NfL concentrations in healthy controls and patients with hATTR amyloidosis at baseline.

(FIG. 5A) mNIS+7 scores in patients over time in the APOLLO clinical trial followed by the 12-month OLE. The number of subjects per groups is indicated at the assessment time points. (FIG. 5B) Levels of NfL in plasma in patients over time in the APOLLO clinical trial, followed by the 12-month OLE. The number of subjects per groups is indicated at the assessment time points. (FIG. 5C) Levels of NfL in healthy controls and placebo or patisiran treated patients at baseline (no significant difference), at 18 months ($p<0.001$), or at 30 months after the 12-month OLE.

(FIG. 6A) Plasma NfL levels at baseline for healthy controls (16.3 μg/ml), ENDEAVOR study subjects (54.1 μg/ml), ENDEAVOR study subjects at baseline having a polyneuropathy disability (PND) score of 0 (46.2) and a PND score >0 (61.4 μg/ml), and at baseline for APOLLO. (mean age for APOLLO was 61 vs. 68 for ENDEAVOR) (FIG. 6B) Plasma NfL level in healthy controls and in ENDEAVOR subjects with V122I mutations (44.9 μg/ml) or other TTR mutations (66.4 μg/ml) at baseline.

DETAILED DESCRIPTION

Figure 1:
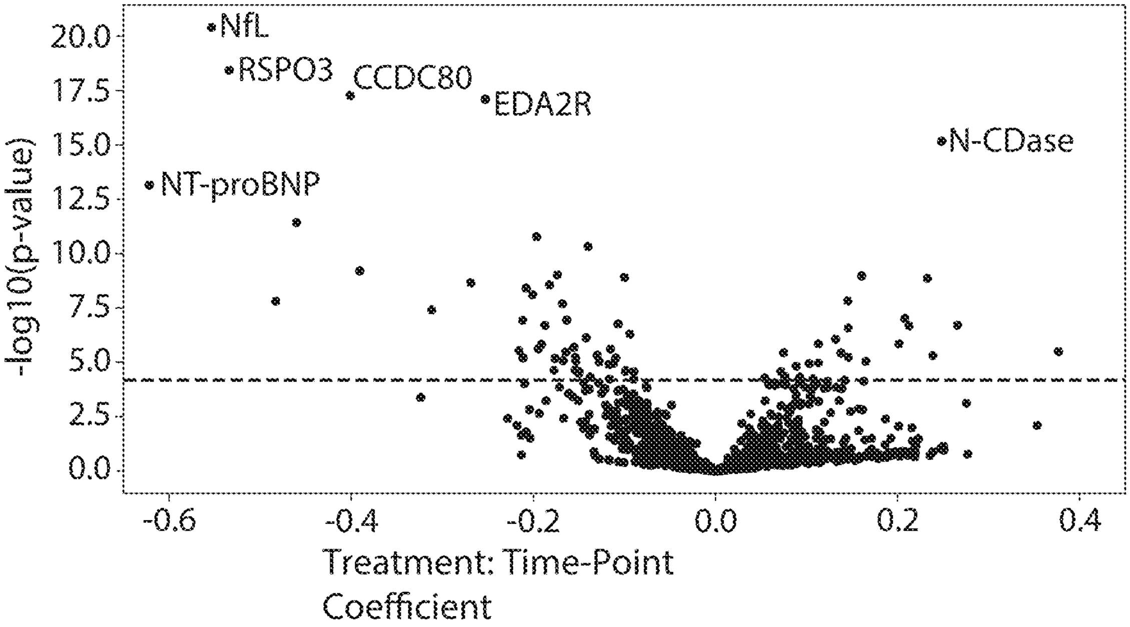
FIG. 1 depicts the change in protein expression after patisiran treatment. A linear mixed model was used to determine the proteins that changed most with patisiran treatment over the course of 18 months. Proteins are shown here as a volcano plot, with the strength of the association on the y-axis (−log 10 (p-value)) and the effect size on the x-axis (shown as the treatmentxtime coefficient from the model).

Hereditary transthyretin-mediated amyloidosis (hATTR) is a rare, rapidly progressing, life-threatening disease caused by pathogenic mutations in the transthyretin (TTR) gene, resulting in misfolded TTR that aggregates into amyloid deposits throughout the body including in the heart, peripheral nerves, and gastrointestinal tract. In turn, this typically results in a multisystem disease that can include peripheral sensorimotor neuropathy, autonomic neuropathy, and cardiomyopathy, and displays variability in regard to the initially affected tissues, age of onset, and penetrance. This inherent variability makes it hard to predict hATTR disease onset and progression in individual patients and requires improved understanding of the disease as a whole, including the ability to identify, track, and effectively treat patients.

Currently, diagnosis of the disease is challenging, both in terms of identifying patients with manifest disease as well as determining when latent carriers of risk TTR alleles become symptomatic. Penetrance of the disease in carriers of TTR variants varies widely by region and TTR variant. Additionally, since TTR aggregates deposit in tissue over time, nerve damage is likely to occur prior to overt symptomatology as fibrils accumulate progressively. One measure used to assess disease severity and progression in patients with hATTR amyloidosis with polyneuropathy is the modified neuropathy impairment score+7 (mNIS+7), which is a composite score derived from a lengthy questionnaire and numerous medical tests to assess sensorimotor and autonomic function. The mNIS+7 scoring system is a helpful way to assess the severity and progression of many of the disease signs and symptoms.

The low prevalence of TTR amyloidosis and the relatively recent availability of disease modifying therapeutics, has limited the clinical understanding of the pathology of the disease and resulted in relatively low urgency in clinical diagnosis due to treatment limitations. Both natural history studies and clinical trials have demonstrated that hereditary TTR amyloidosis manifests in a continuum of signs and symptoms from patients having a predominantly cardiac phenotype to a predominantly polyneuropathy phenotype, with most patients exhibiting both cardiac and neuropathy phenotypes. Wild type TTR can be associated with a cardiac phenotype.

Different therapeutic agents have been approved for patients with different manifestations of TTR amyloidosis. Patisiran and inotersen, which reduce the expression of TTR, have been approved by the US FDA for treatment of polyneuropathy of hereditary transthyretin-mediated amyloidosis. Tafamidis, which stabilizes the TTR tetramer, is approved by the US FDA for the treatment of the cardiomyopathy of wild-type or hereditary transthyretin-mediated amyloidosis to reduce death and hospitalization related to heart problems. Therefore, depending on the initial presentation of the disease, a particular agent may be selected by a health care professional for treatment of a patient with TTR amyloidosis. However, as TTR amyloidosis is known to occur across a spectrum, patients with demonstrated TTR cardiomyopathy should be monitored for development of symptoms indicative of polyneuropathy. By the time that symptoms of polyneuropathy and compromised nerve function are detected though, substantial nerve damage has already taken place. As inhibition of TTR expression has been demonstrated to be effective in the treatment of TTR polyneuropathy, there is an urgency to detect nerve damage as early as possible, preferably before clinical manifestations demonstrating significant loss of nerve function, so that a treatment to inhibit the expression of TTR can be initiated.

To gain additional insights into hATTR disease and the biological processes involved with progression, a plasma proteomics analysis in hATTR patients and a system-wide proteomics interrogation of response to patisiran in humans were performed to understand the biological pathways that enabled disease reversal in more detail. The study identified plasma biomarkers associated with disease progression that can be used to provide a minimally invasive measure that can facilitate earlier patient diagnosis and improved therapeutic intervention.

In the analysis, 1164 unique proteins were measured across samples from the APOLLO study. It was found that the plasma levels of 66 proteins were significantly changed over time in patisiran treated patients compared to placebo.

The most significant protein, neurofilament light chain (NfL), has been described as a biomarker for neuro-axonal damage in some contexts, but has not been associated with hATTR in other published reports to date. At baseline, the APOLLO patients have significantly higher levels of NfL compared to healthy controls and treatment with patisiran significantly decreases NfL levels at both 9 and 18 months. Interestingly, it was observed that, prior to patisiran treatment, patients show global perturbation of their plasma proteomes compared to healthy control subjects. In patients subsequently treated with patisiran a remarkable overall shift in the plasma proteome was observed bringing them more in-line with healthy subjects.

One of the challenges in treating TTR amyloid polyneuropathy is the delay in obtaining a proper diagnosis. Now, as there are effective treatments for TTR amyloidosis, there is a greater urgency to promptly identify and treat subjects with TTR amyloidosis. Although cardiac function is routinely monitored by health care professionals, the time and skill required to perform an assessment for neuropathy is not within the scope of the general practitioner in routine care. The disclosure provides protein biomarkers, including NfL, to detect the presence of neuropathy in a subject predisposed to the development of TTR amyloid polyneuropathy, e.g., a subject with a mutation in a TTR gene associated with TTR amyloidosis or in a subject with cardiovascular TTR amyloidosis prior to the subject meeting the diagnostic criteria for TTR amyloid polyneuropathy. Early detection of an elevated NfL level can be used to prompt initiation of treatment of a subject with an agent that reduces the expression of TTR to treat neuropathy before the development of overt symptoms.

The invention further provides for a method to select a therapeutic agent for treatment of a subject with TTR amyloidosis based on the level of biomarkers, including NfL. Agents that reduce the expression of TTR have been demonstrated in in pivotal trials to be effective in the treatment of TTR amyloid polyneuropathy, including in subjects with a mixed phenotype, i.e., both cardiomyopathy and neuropathy manifestations. Agents that stabilize TTR have not been demonstrated in a clinical trial with statistical significance to be effective in the treatment of TTR amyloid polyneuropathy.

The invention further provides diagnostic kits for detection of biomarkers including NfL for use in the methods of the invention.

Definitions

In order that the present disclosure may be more readily understood, certain terms are first defined. In addition, it should be noted that whenever a value or range of values of a parameter are recited, it is intended that values and ranges intermediate to the recited values are also intended to be part of this disclosure.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "about" is used herein to mean within the typical ranges of tolerances in the art. For example, "about" can be understood as about 2 standard deviations from the mean. In certain embodiments, about mean±10%. In certain embodiments, about mean±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

As used herein, "or" is understood as "and/or" unless context dictates otherwise.

As used herein, methods of detection can include determination that the amount of analyte present is below the level of detection of the method.

As used herein, a "TTR amyloidosis therapeutic agent" is understood as a therapeutic agent that reduces one or more symptom of transthyretin amyloidosis. The TTR therapeutic agent may be, for example, a therapeutic agent that reduces expression of TTR, or a therapeutic agent that stabilizes TTR. In some embodiments, the TTR amyloidosis therapeutic agent prevents the degradation of TTR protein monomers to fragments that are prone to form amyloid plaques.

As used herein, a "therapeutic agent that reduces expression of TTR" and the like as used herein is understood as a therapeutic agent that reduces levels of TTR RNA, TTR protein, or both of TTR RNA and TTR protein. In some embodiments, the therapeutic agent that reduces expression of TTR is a therapeutic agent that promotes the degradation of an mRNA encoding TTR or inhibits the translation of an mRNA encoding TTR. Such agents include, but are not limited to, nucleic acid therapeutics, e.g., RNAi interference agents and antisense oligonucleotide agents. Such agents can typically inhibit expression of both wild type and mutant TTR. The amount of TTR in the subject is reduced, thereby reducing the formation of TTR amyloid plaques. In some embodiments, the agent is an iRNA.

As used herein, a "therapeutic agent that stabilizes TTR" or "that stabilizes a TTR tetramer" is an agent that reduces or prevents the dissociation of the subunits of a TTR tetramer, e.g., into monomers. In some embodiments, the agent reduces the formation of TTR amyloid plaques, e.g., by reducing the level of TTR monomers or proteolytic fragments of TTR monomers that form TTR amyloid plaques. Such agents include, but are not limited to, tafamidis and diflunisal.

As used herein, "neurofilament light chain" or "NfL" is understood as at least a fragment of the sequence of human neurofilament light chain polypeptide, Accession No. NP_006149.2 (SEQ ID NO: 1). In some embodiments, NfL can be specifically identified by any clinically acceptable diagnostic method, e.g., antibody based identification method, e.g., ELISA assay or immunoblotting; chromatography method; or single-molecule array (SIMOA).

As used herein, a "reference level" is understood as a predetermined level to which a level obtained from an assay, e.g., a biomarker level, e.g., a protein biomarker level, is compared. In certain embodiments, a reference level can be a control level determined for a healthy population, e.g., a population that does not have a disease or condition associated with a changed level of the biomarker and does not have a predisposition, e.g., genetic predisposition, to a disease or condition associated with a changed level of the biomarker. In certain embodiments, the population should be matched for certain criteria, e.g., age, gender. In certain embodiments, the reference level of the biomarker is a level from the same subject at an earlier time, e.g., before the development of symptomatic disease or before the start of treatment. Typically, samples are obtained from the subject at clinically relevant intervals, e.g., at intervals sufficiently separated in time that a change in the biomarker could be observed, e.g., at least three month interval, at least a six month interval, or at least a nine month interval. When more than two samples are obtained from a subject over time, it is understood that any of the prior samples can act as a reference level.

As used herein, a "change as compared to a reference level" and the like is understood as a statistically or clinically significant change in the biomarker level, e.g., the change in the protein biomarker level, as compared to the reference level, is greater than the typical standard deviation of the assay method. Moreover, the change should be clinically relevant. The change as compared to a reference level can be determined as a percent change. For example, if a reference level is 100 μg/ml for biomarker X, and the level of biomarker X in the subject is 150 μg/ml, the level is increased by 50% calculated by ((150 μg/ml-100 μg/ml)/100 μg/ml)×100%=50%. If the level of biomarker X in the subject is 300 μg/ml, the level is increased by 300%. If the level of biomarker X in the subject is 50 μg/ml, the level is decreased by 50%. In certain embodiments, the change as compared to a reference level is increased by at least 50%. In certain embodiments, the change as compared to a reference level is increased by at least 100%, at least 200%, or at least 300%. In certain embodiments, the change as compared to a reference sample is decreased by at least 25%. In certain embodiments, the change as compared to a reference sample is decreased by at least 50%.

A "biological sample from a subject" or a "sample from a subject" as used herein, includes one or more fluids, cells, or tissues isolated from a subject. Examples of biological fluids include blood, serum, serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be liver tissue or be derived from the liver. In some embodiments, a "biological sample from a subject" can refer to blood or blood derived serum or plasma from the subject. In some embodiments, the fluid is substantially free of cells, e.g., is free of cells.

As used herein, the term "administering a therapeutic agent" is understood as providing a therapeutic agent to a subject. In embodiments, the therapeutic agent is provided at an appropriate dosage and by a route of administration for the agent as provided, for example, by the label of the therapeutic agent.

As used herein, a "nucleic acid therapeutic agent" is understood as a therapeutic agent comprising a sufficient length of nucleotides to specifically hybridize to a target sequence in a target nucleic acid in a cell such that the hybridization reduces levels of a protein encoded by the target nucleic acid, e.g., by inhibiting translation or promoting sequence specific degradation of the target nucleic acid. Exemplary nucleic acid therapeutic agents include RNAi agents and antisense oligonucleotide agents.

The terms "iRNA", "RNAi agent," "iRNA agent,", "RNA interference agent", "siRNA", "siRNA agent" as used interchangeably herein, refer to an agent that contains RNA as that term is defined herein, and which mediates the targeted cleavage of an RNA transcript, e.g., via an RNA-induced silencing complex (RISC) pathway. iRNA directs the sequence-specific degradation of mRNA through a process known as RNA interference (RNAi). In general, an "iRNA" includes ribonucleotides with chemical modifications. Such modifications may include all types of modifications disclosed herein or known in the art. Any such modifications, as used in a dsRNA molecule, are encompassed by "iRNA" for the purposes of this specification and claims. The RNAi agent may or may not be processed by Dicer prior to entering the RISC pathway. That is, an RNAi agent is a nucleic acid therapeutic that acts by reducing the expression of a target gene, thereby reducing the expression of the polypeptide encoded by the target gene. Exemplary RNAi agents that reduce the expression of TTR include patisiran and vutrisiran.

| RNAi agent | Sense strand (5' to 3') | Antisense strand (5' to 3') |
|---|---|---|
| Patisiran | GuAAccAAGAGuAuuccAudTdT (SEQ ID NO: 9) | AUGGAAuACUCUUGGUuACdTdT (SEQ ID NO: 3) |
| Vutrisiran | usgsggauUfuCfAfUfguaacc aagaL96 (SEQ ID NO: 2) | usCfsuugGfuuAfcaugAfaAf ucccasusc (SEQ ID NO: 4) |

A, C, G, and U are adenosine-3'-phosphate, cytidine-3'-phosphate, guanosine-3'-phosphate, and uridine-3'-phosphate, respectively; a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively; Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively; dT is 2'-deoxythymidine-3'-phosphate; s is a phosphorothioate linkage, and L96 is N-[tris(GalNAc-alkyl)-amidodecanoyl)]-4-hydroxyprolinol.

Further RNAi agents that reduce the expression of TTR are provided, for example, in WO2010048228, WO2013075035, and WO2017023660, each of which is incorporated by reference in its entirety. Still further RNAi agents that reduce the expression of TTR are provided in WO2015085158, which is incorporated by reference in its entirety.

The terms "antisense polynucleotide agent", "antisense oligonucleotide", "antisense compound", and "antisense agent" as used interchangeably herein, refer to an agent comprising a single-stranded oligonucleotide that specifically binds to the target nucleic acid molecules via hydrogen bonding (e.g., Watson-Crick, Hoogsteen, or reversed Hoogsteen hydrogen bonding) and inhibits the expression of the targeted nucleic acid by an antisense mechanism of action, e.g., by RNase H. In some embodiments, an antisense agent is a nucleic acid therapeutic that acts by reducing the expression of a target gene, thereby reducing the expression of the polypeptide encoded by the target gene. Exemplary antisense agents that reduce the expression of TTR include inotersen and IONIS® 682884/ION-TTR-LRx (see, e.g., WO2014179627 which is incorporated by reference in its entirety). Further antisense agents that reduce the expression of TTR are provided, for example in WO2011139917 and WO2014179627, each of which is incorporated by reference in its entirety.

Diagnosis of TTR Amyloidosis Polyneuropathy and Assessment of Disease Burden

TTR amyloidosis is a complex, multifactorial disease. An expanding list of criteria have been used to monitor the progression of TTR-FAP: neuropathy impairment score (NIS), NIS+7, and modified NIS (mNIS)+7 and mNIS+$7_{Ionis}$. These diagnostic criteria are well known in the art and highlights of the criteria are provided below. As used herein, meeting the diagnostic criteria of TTR-FAP is understood as meeting FAP stage 1 criteria, with or without the presence of a mutation associated with hereditary TTR-FAP. Progression of indicators of neuropathy is considered an increase of at least two points in modified neuropathy impairment score (mNIS)+7.

Familial Amyloid Polyneuropathy (FAP) Stage

Coutinho et al developed a clinical staging system for the neuropathy symptoms of hATTR (formerly termed familial amyloid neuropathy). The scale ranges from 1 to 3, as follows (Ando et al. Orphanet J Rare Dis. 2013; 8:31):

| Antisense oligonucleotide | Sequence (5' to 3') |
|---|---|
| inotersen | TCTTGGTTACATGAAATCCC (SEQ ID NO: 5); wherein A, C, G, and T are deoxy nucleotides; A, C, G, and T are 2'-O-methoxyethyl sugar modified nucleotides; and all C are 5-methylcytosine with a full phosphorothioate backbone. |
| IONIS® 682884/ ION-TTR-LRx | GalNac$_3$-7$_{a-0'}$ $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ (SEQ ID NO: 6); wherein A, C, G, and T are adenine, cytosine, guanine, and thymine, respectively; e is a 2'-O-methoxyethyl modified nucleoside; d is a 2'-deoxynucleoside; s is a phosphorothioate intemucleoside linkage; mC is a 5'-methylcytosine; and GalNac$_3$-7$_a$, is a trientanary GalNAc shown in Example 48 of WO2014179627. |

As used herein, a "subject diagnosed with hTTR amyloidosis polyneuropathy" is a subject who has been determined by a health care professional to both meet at least the FAP stage 1 criteria and to have a TTR mutation associated with TTR amyloidosis.

As used herein, a "TTR mutation associated with TTR amyloidosis" includes one of more than 100 mutations of transthyretin known in the art to be associated with TTR amyloidosis, see, e.g., Benson et al. (Am J Cardiol 2011; 108:285-9), Ando et al. (Arch Neurol 2005; 62:1057-62), and the OMIM database 105210 Amyloidosis, Hereditary, Transthyretin-related (omim.org/entry/105210 in the version available on the date of the filing of this priority application).

As used herein, "treatment", treating ", and the like is understood as administration of a therapeutic agent to reduce the rate of progression of a disease or condition or to reduce at least one sign or symptom in a subject suffering from a disease. In certain embodiments, a sign of a disease can be a change in a biomarker from a healthy reference level prior to the development of overt symptoms of the disease. Natural history studies and clinical trials of TTR amyloidosis have demonstrated disease progression in the absence of treatment.

As used herein, "detection of a protein", "detection of a biomarker", and the like are understood as detection of a protein, or a sufficiently large fragment of the protein, to determine the identity of the protein by the method used, e.g., immunological method, chromatography method. In certain embodiments, detection of a protein can include detection of a one or more isoforms of a protein present in a subject when no distinction is made among the various isoforms. In certain embodiments, the detection method is a clinically accepted or validated method.

FAP Stage 1: Walking without assistance, mild neuropathy (sensory, autonomic, and motor) in lower limbs.

FAP Stage 2: Walking with assistance, moderate impairment in lower limbs, trunk, and upper limbs.

FAP Stage 3: wheelchair or bed-ridden, severe neuropathy.

A subject with no neuropathy is considered to be FAP Stage 0.

Polyneuropathy disability (PND) score provides another rating system similarly based on gross motor skills. The scale ranges from 0 to IV as follows (Kerschen and Pleante-Bordeneuve. Curr, Treat, Options Neurol. 2016. 18:53):

PND score 0: No impairment.

PND score I: Sensory disturbances, but preserved walking capability.

PND score II: Impaired walking capability, but ability to walk without a stick or crutches.

PND score IIIA: Walking only with the help of one stick or crutch.

PND score IIIB: Walking with the help of two sticks or crutches.

PND score IV: Confined to a wheelchair or bedridden.

Neuropathy Impairment Scoring Methods

Methods to assess neuropathies are known in the art. For example, in the Mayo Clinic Neurologic Examination Sheet and also in the weakness subscores of Neuropathy Impairment Score (NIS), weakness (NIS-W) are scored in 25% decrements from 1 to 4 points and separately for major muscle groups of each side of the body (Dyck et al., Quantitating overall neuropathic symptoms, impairments, and outcomes. In: Dyck P J, Thomas P K, editors. Peripheral neuropathy. 4th ed. Philadelphia: Elsevier; 2005. p. 1031-52). A broad group, especially of cranial, proximal, and distal limb muscles, is evaluated in NIS-W with a maximum score of 192 points. A decrease of the major 5 muscle stretch reflexes is usually assessed by neurologists and touch pressure, vibration, joint motion, and pin-prick sensations of feet and hands are scored in 25% decrements and from 1 to 4 in the Mayo Clinic Neurology Examination Sheet. To complete NIS of reflexes (NIS-R) and of sensation (NIS-S) Mayo Clinic record scores are transformed to NIS point scores (i.e., Mayo Clinic scores of 1 or 2 are given an NIS point score of 1 and Mayo Clinic scores of 3 or 4 are given an NIS score of 2). Therefore, the maximal NIS scores of the usual reflexes evaluated by neurologists (NIS-R) are 5×2×2=20 points and of the 4 modalities of sensation often evaluated by neurologists (NIS-S) are 8×2×2=32 points. Therefore, the maximum NIS score is: 192+20+32=244 points. The NIS has been described in previous publications (Dyck et al. 2005 and Dyck et al., Neurol. 1997; 49:229-39).

NIS+7 has been used as the primary or co-primary outcome measure in the trials of diabetic sensorimotor polyneuropathy, TTR FAP, and other generalized sensorimotor polyneuropathies (N. Suanprasert et al. J Neurol Sci 344 (2014) 121-128). NIS+7 adequately assesses graded severities of muscle weakness and muscle stretch reflex abnormality with only minimal ceiling effects for reflexes. In NIS+7, 5 of the 7 tests are attributes of nerve conduction-expressed either as normal deviates (Z scores) or points. The attributes included in NIS+7 were chosen because their abnormality sensitively detects diabetic sensorimotor polyneuropathy (Dyck et al. Muscle Nerve 2003; 27 (2): 202-10). The attributes included are the peroneal nerve compound muscle action potential (CMAP) amplitude, motor nerve conduction velocity (MNCV), and motor nerve distal latency (MNDL), tibial MNDL and sural sensory nerve action potential (SNAP) amplitudes. Their measured values can be transformed to normal deviates from percentile values correcting for applicable variables of age, gender, height, or weight as based on earlier studies of a large healthy subject reference cohort. Additionally, these percentile values can be expressed as NIS points from obtained percentile values (i.e., N5th=0 points; ≤5th-N 1st=1 point and ≤1st=2 points (and similarly when abnormality is in the upper tail of the normal distribution).

Assessment of weakness and reflex abnormality, assessment of sensation loss, autonomic dysfunction, and neurophysiologic test abnormalities are not adequately assessed by NIS+7 for use in trials of TTR FAP. In NIS+7 sensation loss is not optimally assessed: 1) body distribution of sensation loss is not adequately taken into account, 2) large as compared to small fiber sensory loss is over emphasized and 3) improved methods of testing and comparison to reference values are preferred over clinical assessments. Also, autonomic dysfunction is not adequately assessed by the use of only heart rate deep breathing (HRdb). The attributes of nerve conduction used to assess NIS+7 are not ideal for the study of TTR FAP.

Modified neuropathy impairment score+7 (mNIS+7), and updated version of NIS+7, is a composite score measuring motor strength, reflexes, sensation, nerve conduction, and autonomic function. Two versions of this composite measure were adapted from the NIS+7 to better reflect hATTR polyneuropathy and have been used as primary outcomes in inotersen and patisiran clinical trials. Key differences between these two versions, and the other neuropathy scoring systems, are summarized in the table below (from Adams et al., BMC Neurology, volume 17, Article number: 181 (2017)). In both scales, a lower score represents better neurologic function (e.g. an increase in score reflects worsening of neurologic impairment).

TABLE 1

Neuropathy Impairment Score Criteria

| | NIS-LL | NIS | NIS + 7 | mNIS + 7 | mNIS + $7_{Ionis}$ |
|---|---|---|---|---|---|
| Total score | 88 | 244 | 270 | 304 | 346.3 |
| Assessment (score) | | | | | |
| Motor strength/ weakness | Neurologic exam [lower limbs only] (64) | Neurologic exam (192) | Neurologic exam (192) | Neurologic exam (192) | Neurologic exam (192) |
| Reflexes | exam Neurologic [lower limbs only] (8) | Neurologic exam (20) | Neurologic exam (20) | Neurologic exam (20) | Neurologic exam (192) |
| | — | — | — | QST-heat pain and touch pressure at multiple sites (80) | QST-heat pain and touch pressure at multiple sites (80) |
| Sensation | Neurologic exam [lower limbs only] (16) | Neurologic exam (32) | Neurologic exam (32) | — | Neurologic exam (32) |
| | — | — | Vibration detection threshold (3.7) | — | — |
| Composite nerve conduction score | — | — | Σ5-sural SNAP/fibular nerve CMAP, tibial motor nerve distal latency, motor nerve conduction velocity, motor nerve distal latency (18.6)[a] | Σ5-Ulnar CMAP and SNAP, peroneal [c] CMAP, tibial CMAP, sural SNAP (10) [b] | Σ5-ulnar CMAP and SNAP, peroneal[c] CMAP, tibial CMAP, sural SNAP (18.6)[a] |

TABLE 1-continued

| Neuropathy Impairment Score Criteria | | | | | |
|---|---|---|---|---|---|
| | NIS-LL | NIS | NIS + 7 | mNIS + 7 | mNIS + $7_{Ionis}$ |
| Autonomic function | — | — | Heart rate response to deep breathing (3.7)[a] | Postural blood pressure (2) [b] | Heart rate response to deep breathing (3.7)[a] |

1. CMAP compound muscle action potential; exam examination; mNIS + 7 modified NIS + 7; NIS Neuropathy Impairment Score; NIS-LL NIS based on examination of lower limbs only; QST quantitative sensory testing; SNAP sensory nerve action potential
2. [a]Score expressed as normal deviates (0-3.72) based on healthy-subject parameters
3. [b]Score graded according to defined categories: normal (95th percentile) = 0 points; mildly reduced (≥95th to <99th percentile) = 1 point; and very reduced (≥99th percentile) = 2 points
4. [c]May also be referred to as fibular Diagnosis of TTR Amyloidosis Cardiomyopathy (ATTR-CM) and Assessment of Disease Burden Patients with hATTR amyloidosis and cardiomyopathy typically experience progressive symptoms of heart failure (HF) and cardiac arrhythmias, with death typically occurring 2.5 to 5 years after diagnosis. Cardiac infiltration of the extracellular matrix by TTR amyloid fibrils leads to a progressive increase of ventricular wall thickness and a marked increase in chamber stiffness, resulting in impaired diastolic function. Systolic function is also impaired, typically reflected by abnormal longitudinal strain despite a normal ejection fraction, which is preserved until late stages of the disease. In patients with ATTR amyloidosis and light-chain (AL) cardiac amyloidosis, both longitudinal strain and N-terminal prohormone of brain natriuretic peptide (NT-proBNP) have been shown to be independent predictors of survival.

Echocardiography is routinely used to assess cardiac structure and function; parameters pre-specified in the statistical analysis plan include mean left ventricular (LV) wall thickness, LV mass, longitudinal strain, and ejection fraction. Cardiac output, left atrial size, LV end-diastolic volume (LVEDV), and LV end-systolic volume (LVESV). Echocardiograms are routinely used for cardiac imaging. Myocardial strain can be assessed with speckle tracking using vendor-independent software (TOMTEC, Munich, Germany). Analysis of NT-proBNP and troponin I levels is routinely performed in clinical laboratories using commercially available diagnostic tests, e.g., using chemiluminescence assays (Roche Diagnostic Cobas, Indianapolis, IN, USA for NT-proBNP; Siemens Centaur XP, Camberley, Surrey, UK for troponin I). Similarly, clinical practice routinely includes measurement of creatinine levels and estimated glomerular filtration rate (eGFR) based on creatinine levels, e.g., using the Modification of Diet in Renal Disease study formula.

A review providing screening and diagnostic methods for ATTR-CM was recently published by Witteles et al., 2019 (JACC: Heart Failure, 2019. 7:709-716) which provides information on methods of diagnosis including a list of "red flags" suggesting the presence of ATTR-CM and screening methods including echocardiography, electrocardiogramagnetic resonance, the presence of systemic symptoms involving the peripheral or autonomic nervous system along with cardiac dysfunction including bilateral sensory motor polyneuropathy that begins in the lower limbs and follows an ascending pattern, dysautonomia in the form of orthostatic hypotension, diarrhea/constipation, and erectile dysfunction, and eye involvement such as glaucoma, intravitreal deposition, and scalloped pupils; carpal tunnel syndrome, especially bilateral carpal tunnel syndrome, lumbar spinal stenosis, and bicep tendon rupture. Other diagnostic methods include bone scintography with technetium (Tc)-labelled bisphosphonates localizes to TTR cardiac amyloid deposits for reasons that are not known. Biopsy is also used to confirm the presence of TTR amyloidosis in heart.

Methods for assessment and classification of cardiac function of the parameters provided above are known in the art. As used herein, the specific method of assessment or classification of cardiac function may be any clinically acceptable standard to demonstrate sufficiently decreased cardiac function such that the standard of care includes a medical intervention, e.g., administration of a pharmacological agent, surgery.

Protein Biomarkers for the Diagnosis of TTR Amyloidosis Polyneuropathy

Plasma proteomics and the identification of minimally invasive biomarkers is emerging as an integral part of modern drug discovery and clinical development. In an effort to leverage this approach, the plasma proteomes of hATTR patients were investigated over time in a clinical proteomic study of hATTR. The proteomics approach demonstrated that patisiran treatment results in a general shift in the proteome of patients toward that of healthy individuals relative to placebo, suggesting that the plasma protein milieu is reflective of hATTR disease progression and response to treatment. Sixty six proteins were found to exhibit a significantly different plasma level time profile in placebo compared to patisiran treated patients. During the course of 18 months, of the 1164 unique proteins across samples from the APOLLO study, neurofilament light chain (NfL) was identified as the protein most significantly impacted by treatment. NfL is a well-described biomarker for neuro-axonal damage but has not been associated with hATTR in other published reports to date. NfL is emerging as a crucial biomarker indicative of disease severity and progression both in many central and peripheral nervous system diseases. At baseline, the APOLLO patients have significantly higher levels of NfL compared to healthy controls and treatment with patisiran significantly decreases NfL levels at both 9 and 18 months. Interestingly, it was observed that, prior to patisiran treatment, patients showed global perturbation of their plasma proteomes compared to healthy control subjects. In patients subsequently treated with patisiran, a remarkable overall shift in the plasma proteome was observed bringing them more in-line with healthy subjects. Together these findings demonstrate that treatment with patisiran shifts the proteome of patients towards that of healthy controls and identifies additional proteins that have both the potential to serve as biomarkers and offer insights into hATTR disease biology. This remarkable finding indicates that although patisiran directly targets only TTR production, multiple processes are changing in response to treatment leading towards a healthier state.

The demonstration that plasma levels of NfL are significantly elevated in hATTR patients with polyneuropathy, and subsequently decreased after patisiran treatment, is relevant to diagnosis, treatment, and monitoring of ATTR progression. This finding is particularly compelling due to the emerging role of NfL as a general biomarker of central and peripheral nervous system dysfunction. NfL is an integral component of the axonal structure of neurons and has been described as a biomarker of neuroaxonal injury across central nervous system diseases. See, e.g., Gunnarsson et al, 2011; Lewczuk et al, 2018; Lin et al, 2018; Byrne et al, 2017; Bischof et al, 2018; Van Lieverloo et al, 2019; Mariotto et al, 2018; Sandelius et al, 2018Lycke et al, 1998; Preische et al, 2019. While not wishing to be bound by theory, based at least on results described herein, since treatment with patisiran lowers the mRNA levels of TTR, and therefore protein levels of circulating TTR, the reduction in amyloidogenic aggregates may result in a reduction of neuronal damage, thereby lowering circulating NfL. Interestingly, reductions in NfL levels are observed as early as 9 months post initiation of patisiran treatment indicating that treatment is reducing hATTR-associated neuronal damage by 9 months. Within the 18 months of this study, the levels of NfL that observed upon patisiran treatment do not return to the levels observed in healthy individuals.

Figure 2A:
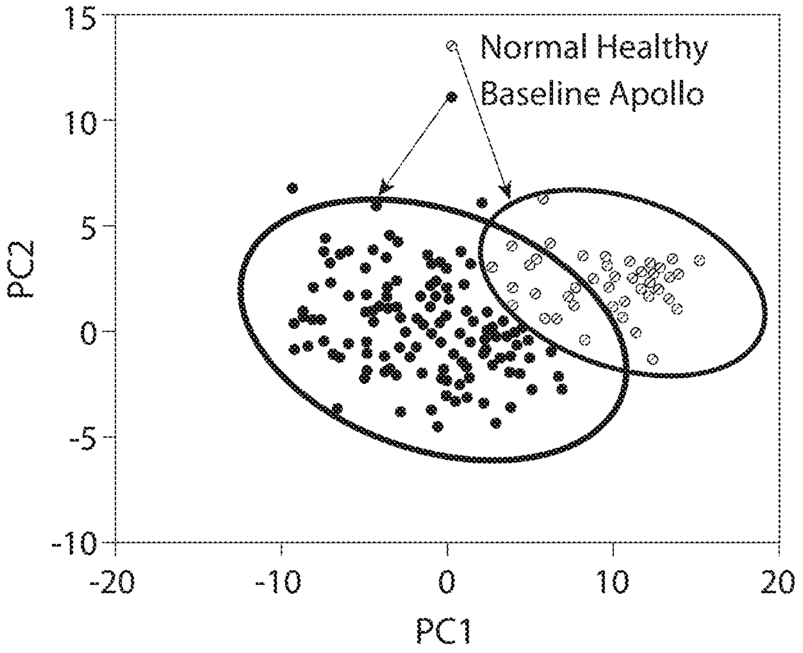
FIGS. 2A-2E depict that the proteome of patisiran treated patients moves towards that of healthy controls.

A correlation was observed between change in NfL levels at 18 months and change in mNIS+7 at 18 months (FIG. 2*d*), but no correlation was observed at baseline between NfL levels and mNIS+7. One possibility for this difference is that there is significant heterogeneity in the levels of NfL in different individuals based on age and gender, in addition to disease status, and that NfL changes over time within an individual is more informative regarding disease status. Another possibility for the lack in correlation with mNIS+7 at baseline is that patients entering the APOLLO trial are already carrying significant disease burden and have a saturated NfL signal, which has already been described in other diseases (Byrne et al., 2019).

As demonstrated herein, NfL levels are elevated in hATTR patients with polyneuropathy as per APOLLO inclusion criteria and decrease in response to patisiran treatment. In addition to monitoring disease regression upon treatment, NfL may serve as a potential biomarker in other aspects of hATTR disease. If levels of NfL increase during hATTR polyneuropathy early disease development, NfL may serve as a prognostic indicator for the transition from asymptomatic to symptomatic. In fact, literature reports have suggested NfL as a biomarker in asymptomatic patients about to develop disease in amyotrophic lateral sclerosis (Benatar et al, 2018) and Alzheimer's disease (Weston et al., 2019). Additionally, NfL may potentially play an important role for distinguishing between effectiveness of various treatments. Lastly, while the present study was based on patients with hATTR polyneuropathy due to disease inclusion criteria of the APOLLO study, many also exhibited cardiomyopathie manifestation. Therefore, the presence of elevated NfL is not limited to patients exhibiting exclusively a polyneuropathy phenotype.

Protein Biomarkers for Monitoring the Progression of TTR Amyloidosis Polyneuropathy The mNIS+7 method for assessing polyneuropathy is often not practical in a primary care setting. Although the FAP staging system is useful for characterizing disease progression, it does not provide detailed information on disease progression. The limitations of these methods can make it difficult to assess when a subject should be started on treatment with an agent that reduces the expression of TTR.

Genetic testing is available for identification of subjects who have a TTR mutation associated with TTR amyloidosis. Further, subjects with cardiovascular (CV) TTR amyloidosis may develop amyloid deposit in peripheral nerves without developing overt neuropathy. However, the age of onset of neuropathy varies widely depending on both the mutation and the individual. This disclosure provides NfL as a biomarker to determine when a subject with a predisposition to TTR amyloidosis polyneuropathy, e.g., a subject with a genetic predisposition or a subject with CV-TTR amyloidosis, may be treated with an agent that reduces the expression of TTR. In certain embodiments, after the subject is identified as having a TTR mutation associated with TTR amyloidosis, the subject is routinely monitored for an increase in NfL level as compared to a reference level, either a population control or a prior NfL level for the same subject. An increase in a NfL in the subject is an indicator treatment of the subject, e.g., with an agent that reduces the expression of TTR should be initiated. In certain embodiments, the subject is also routinely monitored for the development of a sign or symptom of polyneuropathy. In certain embodiments, the subject is also monitored for the level of one or more of the proteins in Table 2, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the protein biomarkers from Table 2 are selected from RSPO3, CCDC80, EDA2R, NT-proBNP, and N-CDase, wherein the elevation of one or more of RSPO3, CCDC80, EDA2R, and NT-proBNP; or a decrease in N-CDase is an indication of worsening TTR amyloidosis. In certain embodiments wherein the subject is being treated with an agent that stabilizes TTR, treatment with that agent can be discontinued.

Monitoring of NfL levels can also be used to determine if polyneuropathy is progressing in a subject with TTR amyloidosis polyneuropathy where an increase in the level of NfL in a subject is indicative of progressive polyneuropathy. Progression can be monitored by further determining the level of one or more of the proteins in Table 2, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the protein biomarkers from Table 2 are selected from RSPO3, CCDC80, EDA2R, NT-proBNP, and N-CDase, wherein the elevation of one or more of RSPO3, CCDC80, EDA2R, and NT-proBNP; or a decrease in N-CDase is an indication of worsening TTR amyloidosis.

Establishing Reference Standards of Protein Biomarker Levels

The disclosure provides the steps of measuring one or more protein biomarker levels in a subject and comparison of a biomarker level to its corresponding reference level to determine if there is a difference between the biomarker level and its corresponding reference level. It is understood that the method for determining the level of the biomarker in the sample and the method by which the reference level was determined for the reference level should be the same. Further, it is understood that the change from the reference level may be a change in a defined concentration of a biomarker in a sample, e.g., pg/ml of sample. Alternatively, the change can be a relative amount, a change in percent of the reference sample, e.g., at least 150% or at least 200% of the reference sample. The change in the level should be statistically significant. Methods to determine biomarker levels are typically performed in vitro, often in a clinical lab setting when used for diagnostic methods and methods used to select a treatment for a subject.

Commercially available kits are available to determine the level of some biomarkers, e.g., NT-proBNP and troponin I. Levels of these markers can be performed in clinical laboratories using commercially available diagnostic tests, e.g., using chemiluminescence assays (Roche Diagnostic Cobas, Indianapolis, IN, USA for NT-proBNP; Siemens Centaur XP, Camberley, Surrey, UK for troponin I). In such cases, the reference level of the biomarker, and in embodiments an appropriate control, can be provided by the kit manufacturer.

Neurofilament light chain level has been assessed as a biomarker for neuronal damage, for example, in multiple sclerosis by Disanto et al. (Ann Neurol. 2017; 81:857-870) and in Alzheimer's disease and Parkinson's disease by Lin et al. (Sci Rep. 2018; 8:17368). The studies used 254 and 59 healthy controls, respectively, and both studies used the single-molecule array (SIMOA) system from Quanterix Corporation to determine NfL levels. Lin demonstrated that male patients had higher plasma NfL levels than female patients ($p=0.03$, t-test), and that plasma NfL level increased with age (Pearson $r=0.427$, $p<0.001$). This age-related effect on plasma NFL level was seen across all sub-groups. Similarly, Disanto found that NfL levels are age dependent and provides a table of estimated plasma NfL percentiles across different ages. These studies demonstrate that no single reference level is appropriate for all subjects. Instead, an appropriate age and gender matched control reference standard can be selected for comparison to population based controls. Such considerations are understood in the art.

When an earlier time point for a subject is used as a reference level, a sufficient interval to allow for a change in biomarker level needs to be provided. As demonstrated herein, changes in NfL levels were observed between day 0 and the 9 month time points, and the 9 month and 18 month time points, both in control subjects with increasing levels of NfL, and in patisiran treated subjects with decreasing NfL levels. Therefore, 9 months is a sufficient interval for a change in NfL level. It is expected (based at least on the data provided herein) that shorter intervals, e.g., 6 months or even 3 months, can also be sufficient to observe a change in NfL level in a subject depending on the disease state and rate of progression in the subject.

Signs and Symptoms of Polyneuropathy

The methods of the invention can further include monitoring subjects for one or more signs or symptoms indicative of polyneuropathy or progression of polyneuropathy including, but not limited to, dysautonomia in the form of orthostatic hypotension, diarrhea, constipation, erectile dysfunction, glaucoma, intravitreal deposition, scalloped pupils; carpal tunnel syndrome, lumbar spinal stenosis, and bicep tendon rupture, or any combination thereof. The development or progression of one or more of the signs or symptoms, in the context of an elevated NfL level as compared to a reference level, is further diagnostic of amyloid TTR polyneuropathy.

Nucleic Acid Therapeutics that Reduce the Expression of TTR

In some embodiments, the methods described herein involve use of a nucleic acid therapeutic agent (e.g., an RNAi agent) that reduces expression of TTR.

In some embodiments, the RNAi agent comprises a dsRNA that comprises (i) an antisense strand comprising a sequence AUGGAAUACUCUUGGUUAC (SEQ ID NO: 7) and (ii) a sense strand comprising a sequence GUAACCAAGAGUAUUCCAU (SEQ ID NO: 8). In some embodiments, the sense strand further comprises an overhang (e.g., a 3' overhang) of 1 or 2 nucleotides, e.g., dTdT. In some embodiments, the antisense strand further comprises an overhang (e.g., a 3' overhang) of 1 or 2 nucleotides, e.g., dTdT. In some embodiments, the sense strand is about 19-23 (e.g., 21) nucleotides in length or the antisense strand is about 19-23 (e.g., 21) nucleotides in length. In some embodiments, one or more U in the sense or antisense strand is 2'-O-methyluridine-3'-phosphate. In some embodiments, one or more C in the sense strand 2'-O-methylcytidine-3'-phosphate. In some embodiments, the sense strand comprises 1, 2, 3, 4, 5, 6, 7, 8, or 9 2'O-Methyl nucleotides. In some embodiments, the antisense strand comprises 1 or 2 2'O-Methyl nucleotides.

In other embodiments, the iRNA comprises a dsRNA having an RNA strand (the antisense strand) having a region that is substantially complementary to a portion of a TTR mRNA. In some embodiments, the iRNA comprises a dsRNA having an RNA strand (the antisense strand) having a region that is substantially complementary to a portion of an TTR mRNA, e.g., a human TTR mRNA, e.g., a sequence provided herein.

In one embodiment, an iRNA for inhibiting expression of TTR includes at least two sequences that are complementary to each other. The iRNA includes a sense strand having a first sequence and an antisense strand having a second sequence. In embodiments, the antisense strand includes a nucleotide sequence that is substantially complementary to at least part of an mRNA encoding a TTR transcript, and the region of complementarity is 30 nucleotides or less, and at least 15 nucleotides in length. In embodiments, the iRNA is 19 to 24 nucleotides in length.

In some embodiments, the iRNA is 19-21 nucleotides in length. In some embodiments, the iRNA is 19-21 nucleotides in length and is in a lipid formulation, e.g. a lipid nanoparticle (LNP) formulation (e.g., an LNP11 formulation).

In some embodiments, the iRNA is 21-23 nucleotides in length. In some embodiments, the iRNA is 21-23 nucleotides in length and is in the form of a conjugate, e.g., conjugated to one or more GalNAc.

In some embodiments the iRNA is from about 15 to about 25 nucleotides in length, and in some embodiments the iRNA is from about 25 to about 30 nucleotides in length. In some embodiments, an iRNA targeting TTR, upon contact with a cell expressing TTR, inhibits the expression of a TTR gene by or at least 80% or more. In one embodiment, the iRNA targeting TTR is formulated in a stable nucleic acid lipid particle (SNALP).

In embodiments, the iRNA comprises a duplex region that is 15-50, 17-23, 19-21, or 21-23 nucleotide pairs in length.

In some embodiments, at least one strand comprises a 3' overhang of at least 1 nucleotide. In some embodiments, at least one strand comprises a 3' overhang of at least 2 nucleotides.

The iRNA molecules described herein can include naturally occurring nucleotides or can include at least one modified nucleotide, including, but not limited to a 2'-O-methyl modified nucleotide, a nucleotide having a 5' phosphorothioate group, and a terminal nucleotide linked to a cholesteryl derivative. Alternatively or in combination, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

In some embodiments, an iRNA as described herein is in the form of a conjugate, e.g., a carbohydrate conjugate, which may serve as a targeting moiety or ligand, as described herein. In one embodiment, the conjugate is attached to the 3' end of the sense strand of the dsRNA. In some embodiments, the conjugate is attached via a linker, e.g., via a bivalent or trivalent branched linker.

In embodiments of the pharmaceutical compositions described herein, the composition is formulated for intravenous administration. In embodiments of the pharmaceutical compositions described herein, the composition is formulated for subcutaneous administration.

Further Embodiments

The disclosure provides methods for identifying a pre-symptomatic subject, e.g., a human subject, as being at risk for developing polyneuropathy manifestations of TTR amyloidosis polyneuropathy by measuring an NfL level in the subject, wherein elevated NfL level as compared to a reference level is indicative of future development of TTR amyloidosis polyneuropathy signs or symptoms.

In certain embodiments, the subject has cardiac manifestations of TTR amyloidosis. In certain embodiments, the NfL level in the subject increases over time.

In certain embodiments, the subject does not meet the diagnostic criteria for TTR amyloidosis polyneuropathy. In some embodiments, the subject does not meet FAP stage 1 diagnostic criteria.

In certain embodiments, the subject has a TTR mutation associated with TTR amyloidosis. In other embodiments, the subject does not have a mutation associated with TTR amyloidosis.

In certain embodiments, the subject also has an altered level as compared to a reference level of one or more (e.g., at least 2, 3, 4, 5, 6, 7, 8, 9, or 10) biomarkers in Table 2, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the subject has an elevated level as compared to a reference level of one or more of (e.g., 2, 3, or all of) RSPO3, CCDC80, EDA2R, and NT-proBNP, indicative of TTR amyloidosis progression. In certain embodiments, the subject has a decreased level as compared to a reference level of N-CDase, indicative of TTR amyloidosis progression.

In certain embodiments, the levels are protein levels determined in a subject sample, e.g., blood, or plasma or serum derived therefrom.

In certain embodiments, the reference level is based on a control population level. In certain embodiments, the control population level is matched to a subject for one or more relevant factors for the marker, e.g., gender, age. In certain embodiments, the reference level is based on an earlier level from a sample from the subject. In certain embodiments, the reference level is from a sample obtained at least three months earlier or at least six months earlier. In certain embodiments, the reference level is from a sample obtained at least nine months earlier.

In certain embodiments, the subject is being treated with tafamidis or diflunisal. In certain embodiments, the method further comprises treating the subject with an agent that reduces the expression of TTR. In certain embodiments, the method further comprises treating the subject with an agent that reduces the expression of TTR instead of tafamidis or diflunisal.

In certain embodiments, the subject further is suffering from one or more further indicators of TTR amyloidosis selected from dysautonomia in the form of orthostatic hypotension, diarrhea, constipation, erectile dysfunction, glaucoma, intravitreal deposition, scalloped pupils; carpal tunnel syndrome, lumbar spinal stenosis, and bicep tendon rupture.

The disclosure provides methods for monitoring progression of neurological damage in TTR amyloidosis polyneuropathy in a subject, e.g., a human subject, by monitoring NfL level by determining an NfL level in the subject at a first time to provide a reference level, determining an NfL level in the subject to provide a second NfL level, comparing the second NfL level to the first NfL level, wherein an increase in the second NfL level is indicative of progression of polyneuropathy.

In certain embodiments, the subject does not meet the diagnostic criteria for polyneuropathy manifestations of TTR amyloidosis. In some embodiments, the subject does not meet FAP stage 1 diagnostic criteria.

In certain embodiments, the subject has a TTR mutation associated with TTR amyloidosis. In other embodiments, the subject does not have a mutation associated with TTR amyloidosis.

In certain embodiments, the method further includes determining the level of one or more (e.g., at least 2, 3, 4, 5, 6, 7, 8, 9, or 10) of the biomarkers in Table 2 and comparing the level to a reference level, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the subject has an elevated level as compared to a reference level of one or more of (e.g., 2, 3, or all of) RSPO3, CCDC80, EDA2R, and NT-proBNP, indicative of worsening TTR amyloidosis. In certain embodiments, the subject has a decreased level as compared to a reference level of N-CDase, indicative of worsening TTR amyloidosis.

In certain embodiments, the levels are protein levels determined in a subject sample, e.g., blood, or plasma or serum derived therefrom.

In certain embodiments, the reference level of the biomarker in Table 2 is based on a control population level. In certain embodiments, the control population level is matched to a subject for one or more relevant factors for the marker, e.g., gender, age. In certain embodiments, the reference level is based on an earlier level from a sample from the subject. In certain embodiments, the reference level is from a sample obtained from the subject at least three months earlier or at least six months earlier. In certain embodiments, the reference level is from a sample obtained from the subject at least nine months earlier.

In certain embodiments, the subject is being treated with tafamidis or diflunisal. In certain embodiments, the method further comprises treating the subject with an agent that reduces the expression of TTR, e.g., patisiran or vutrisiran. In certain embodiments, the method further comprises treating the subject with an agent that reduces the expression of TTR instead of tafamidis or diflunisal.

The disclosure provides methods for selecting a therapeutic agent for treatment of a subject, e.g., a human subject, with a TTR mutation associated with TTR amyloidosis comprising determining a NfL level; and selecting an agent that reduces the expression of TTR for treatment of the subject when the subject has an increase NfL level as compared to a reference level.

In certain embodiments, the subject does not meet the diagnostic criteria for polyneuropathy manifestations of TTR amyloidosis. In some embodiments, the subject does not meet FAP stage 1 diagnostic criteria.

In certain embodiments, the subject also has an altered level as compared to a reference level of one or more (e.g., at least 2, 3, 4, 5, 6, 7, 8, 9, or 10) biomarkers in Table 2, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the subject has an elevated level as compared to a reference level of one or more of (e.g., 2, 3, or all of) RSPO3, CCDC80, EDA2R, and NT-proBNP, indicative of worsening TTR amyloidosis. In certain embodiments, the subject has a decreased level as compared to a reference level of N-CDase, indicative of worsening TTR amyloidosis.

In certain embodiments, the levels are protein levels determined in a subject sample, e.g., blood, or serum derived therefrom.

In certain embodiments, the reference level is based on a control population level. In certain embodiments, the control population level is matched to a subject for one or more relevant factors for the marker, e.g., gender, age. In certain embodiments, the reference level is based on an earlier level from a sample from the subject. In certain embodiments, the reference level is from a sample obtained at least three months earlier or at least six months earlier than the test sample. In certain embodiments, the reference level is from a sample obtained at least nine months earlier than the test sample.

In certain embodiments, the subject is being treated with tafamidis or diflunisal. In certain embodiments, the method further comprises treating the subject with an agent that reduces the expression of TTR, e.g., patisiran or vutrisiran. In certain embodiments, the method further comprises treating the subject with an agent that reduces the expression of TTR instead of tafamidis or diflunisal.

In certain embodiments, the levels are protein levels determined in a subject sample, e.g., blood, or plasma or serum derived therefrom.

In certain embodiments, the subject further is suffering from one or more further indicators of polyneuropathy selected from dysautonomia in the form of orthostatic hypotension, diarrhea, constipation, erectile dysfunction, glaucoma, intravitreal deposition, scalloped pupils; carpal tunnel syndrome, lumbar spinal stenosis, and bicep tendon rupture.

The disclosure provides methods for deciding to initiate treatment with a therapeutic agent for treatment of a subject, e.g., a human subject, predisposed TTR amyloidosis polyneuropathy comprising determining a NfL level; and initiating treatment with an agent that reduces the expression of TTR for treatment of the subject when the subject has an increase NfL level as compared to a reference level.

In certain embodiments, the subject does not meet the diagnostic criteria for polyneuropathy manifestations of TTR amyloidosis. In some embodiments, the subject does not meet FAP stage 1 diagnostic criteria.

In certain embodiments, the subject has a TTR mutation associated with TTR amyloidosis. In other embodiments, the subject does not have a mutation associated with TTR amyloidosis.

In certain embodiments, the subject also has an altered level as compared to a reference level of one or more biomarkers in Table 2, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the subject has an elevated level as compared to a reference level of one or more of (e.g., 2, 3, or all of) RSPO3, CCDC80, EDA2R, and NT-proBNP, indicative of worsening TTR amyloidosis. In certain embodiments, the subject has a decreased level as compared to a reference level of N-CDase, indicative of worsening TTR amyloidosis.

In certain embodiments, the levels are protein levels determined in a subject sample, e.g., blood, or plasma or serum derived therefrom.

In certain embodiments, the reference level is based on a control population level. In certain embodiments, the control population level is matched to a subject for one or more relevant factors for the marker, e.g., gender, age. In certain embodiments, the reference level is based on an earlier level from a sample from the subject. In certain embodiments, the reference level is from a sample obtained at least three months earlier or at least six months earlier. In certain embodiments, the reference level is from a sample obtained at least nine months earlier.

In certain embodiments, the subject is being treated with tafamidis or diflunisal. In certain embodiments, the method further comprises treating the subject with an agent that reduces the expression of TTR. In certain embodiments, the method further comprises treating the subject with an agent that reduces the expression of TTR instead of tafamidis or diflunisal.

In certain embodiments, the levels are protein levels determined in a subject sample, e.g., blood, or plasma or serum derived therefrom.

In certain embodiments, the subject further is suffering from one or more further indicators of polyneuropathy selected from dysautonomia in the form of orthostatic hypotension diarrhea, constipation, erectile dysfunction, glaucoma, intravitreal deposition, scalloped pupils; carpal tunnel syndrome, lumbar spinal stenosis, and bicep tendon rupture.

The disclosure provides methods of diagnosing TTR amyloidosis polyneuropathy in a subject by determining a neurofilament level in a subject, wherein an increased level of NfL as compared to a reference level is indicative of TTR amyloidosis.

In certain embodiments, the subject does not meet the diagnostic criteria for polyneuropathy manifestations of TTR amyloidosis. In some embodiments, the subject does not meet FAP stage 1 diagnostic criteria.

In certain embodiments, the subject has a TTR mutation associated with TTR amyloidosis. In other embodiments, the subject does not have a mutation associated with TTR amyloidosis.

In certain embodiments, the subject also has an altered level as compared to a reference level of one or more biomarkers in Table 2, wherein an increase in the level of a protein biomarker as compared to a reference level when the beta coefficient is positive is indicative of worsening TTR amyloidosis, and a decrease in the level of a protein biomarker as compared to a reference level when the beta coefficient is negative is indicative of worsening TTR amyloidosis. In certain embodiments, the subject has an elevated level as compared to a reference level of one or more of (e.g., 2, 3, or all of) RSPO3, CCDC80, EDA2R, and NT-proBNP, indicative of worsening TTR amyloidosis. In certain embodiments, the subject has a decreased level as compared to a reference level of N-CDase, indicative of worsening TTR amyloidosis.

In certain embodiments, the levels are protein levels determined in a subject sample, e.g., blood, or plasma or serum derived therefrom.

In certain embodiments, the reference level is based on a control population level. In certain embodiments, the control population level is matched to a subject for one or more relevant factors for the marker, e.g., gender, age. In certain embodiments, the reference level is based on an earlier level from a sample from the subject. In certain embodiments, the reference level is from a sample obtained at least three months earlier or at least six months earlier. In certain embodiments, the reference level is from a sample obtained at least nine months earlier.

In certain embodiments, the subject is being treated with tafamidis or diflunisal. In certain embodiments, the method further comprises treating the subject with an agent that reduces the expression of TTR. In certain embodiments, the method further comprises treating the subject with an agent that reduces the expression of TTR instead of tafamidis or diflunisal.

In certain embodiments, the levels are protein levels determined in a subject sample, e.g., blood, or plasma or serum derived therefrom.

In certain embodiments, the subject further is suffering from one or more of diarrhea, constipation, erectile dysfunction, glaucoma, intravitreal deposition, scalloped pupils; carpal tunnel syndrome, lumbar spinal stenosis, and bicep tendon rupture.

The disclosure provides kits for practicing the methods of the invention. In certain embodiments the kit includes one or more reagents for the detection of a NfL level in a sample, e.g., a blood, plasma, or serum sample. Alternatively or in combination, the kit may comprise one or more, reagents for detection of the level of one or more (e.g., at least 2, 3, 4, 5, 6, 7, 8, 9, or 10) of the biomarkers listed in Table 2, for instance one or more of (e.g., 2, 3, or all of) RSPO3, CCDC80, EDA2R, NT-proBNP, and N-CDase. In certain embodiments, the kit further includes one or more control samples (e.g., positive or negative control samples) for detection of the level of NfL and the one or more additional biomarkers. In certain embodiments, the kit further includes instructions for use in the assay or for use of the results to perform any of the methods provided herein. In certain embodiments, the kit provides information on reference levels of NfL and the one or more additional biomarkers. In certain embodiments, the level of NfL and the level of the one or more additional biomarkers is determined using the same method. In certain embodiments, the level of NfL and the level of the one or more additional biomarkers are not determined using the same method. In certain embodiments, the kit components are packaged or sold together for use in the methods provided herein.

The disclosure further provides uses of the biomarkers and therapeutic agents provided herein based on the disclosed methods.

The disclosure also provides therapeutic agents for use with the methods provided herein to select subjects for treatment with particular therapeutic agents, e.g., agents that reduce expression of TTR.

Example 1. Plasma Proteome Analysis of Patients with Hereditary Transthyretin-Mediated (hATTR) for Biomarkers of Disease and Treatment Response Plasma levels of 1164 unique proteins were analyzed using proximity extension assay in 136 patisiran treated and 53 placebo treated patients from the APOLLO study, a phase 3 placebo controlled clinical trial for hATTR with polyneuropathy. The abundance of these proteins was measured from each patient at three separate timepoints: baseline, 9 months, and 18 months. Because the APOLLO trial enrolled only patients diagnosed with hATTR, the levels of the same proteins were also evaluated in 57 healthy controls that were age, sex, and race matched to the APOLLO patients' demographics to allow comparison of proteome differences between disease patients at baseline and healthy controls as well as proteome differences occurring upon treatment of hATTR patients.

A linear mixed model was used to determine the impact of treatment on the time profile of each protein plasma level across the time-course of baseline, 9 months, and 18 months. A total of 66 proteins were found to show a significant interaction term between time and treatment ($p<4.18\times10_{-5}$; applying Bonferroni correction), of which NfL was the most significant (FIG. 1; p-value$=3.95\times10^{-21}$). A significant decrease in the levels of NT-proBNP upon patisiran treatment was observed, consistent with prior reports of this described biomarker of cardiac health and measurements in the APOLLO study (p-value$=7.02\times10^{-14}$). Both proteins that increase upon patisiran treatment (e.g. N-CDase) and proteins that decrease upon treatment (e.g. RSPO3, CCDC80) were identified, many of which have not been described as biomarkers previously (full list in Table 2). Table 2 provides Full list of all proteins that significantly changed (Bonferroni threshold p-value $<4.18\times10^{-5}$) found using a linear mixed model to compare placebo and patisiran treated patients over time. Beta coefficient of timextreatment term and $-\log_{10}$ (p-value) are listed.

TABLE 2

Biomarkers with changed levels in response to patisiran treatment

| Protein | beta coefficient | −log10 (p-value) | Protein | beta coefficient | −log10 (p-value) |
|---|---|---|---|---|---|
| NfL | 0.55 | 20.40 | LDLR | −0.20 | 5.85 |
| RSPO3 | 0.53 | 18.43 | NOV | 0.19 | 5.83 |
| CCDC80 | 0.40 | 17.28 | CD160 | 0.16 | 5.69 |
| EDA2R | 0.25 | 17.10 | PI3 | 0.19 | 5.61 |
| N-CDase | −0.25 | 15.17 | SMOC1 | 0.12 | 5.61 |
| NT-proBNP | 0.62 | 13.15 | TFPI-2 | 0.22 | 5.54 |
| | 0.46 | 11.43 | LEP | −0.38 | 5.49 |
| WNT9A | 0.20 | 10.78 | TNFRSF19 | 0.16 | 5.47 |
| SMOC2 | 0.14 | 10.33 | ERBB3 | −0.07 | 5.44 |
| PIN | 0.39 | 9.20 | DUA | −0.14 | 5.43 |
| HGF | 0.17 | 9.02 | IL-4RA | 0.13 | 5.33 |
| | 0.14 | 6.13 | REN | −0.24 | 5.31 |
| NELL1 | −0.16 | 8.98 | CES2 | −0.15 | 5.23 |
| DCN | 0.10 | 8.90 | CR2 | 0.15 | 5.23 |
| ARSA | −0.23 | 8.86 | PSG1 | 0.21 | 5.20 |
| KLK4 | 0.27 | 8.66 | FGF-BP1 | 0.11 | 5.19 |
| GPC1 | 0.18 | 8.57 | OPN | 0.18 | 5.18 |
| SERF | 0.21 | 8.41 | TFF3 | 0.17 | 5.08 |
| DRAXIN | 0.20 | 8.11 | ANGPT2 | 0.15 | 5.05 |
| IL-18R1 | −0.15 | 7.82 | CCL24 | −0.17 | 5.05 |

TABLE 2-continued

Biomarkers with changed levels in response to patisiran treatment

| Protein | beta coefficient | −log10 (p-value) | Protein | beta coefficient | −log10 (p-value) |
|---|---|---|---|---|---|
| BNP | 0.48 | 7.81 | LAYN | 0.13 | 5.02 |
| GFR-alpha1 | 0.17 | 7.69 | FUCA1 | −0.11 | 4.97 |
| CXCL9 | 0.31 | 7.42 | AXL | 0.11 | 4.95 |
| TIMD4 | −0.21 | 7.02 | TLR3 | −0.10 | 4.94 |
| RSPO1 | 0.16 | 6.94 | SCARB2 | 0.12 | 4.90 |
| MYOC | 0.21 | 6.94 | B4GAT1 | −0.09 | 4.83 |
| WFDC2 | 0.11 | 6.76 | SORCS2 | 0.15 | 4.65 |
| GUSB | −0.27 | 6.71 | CD300E | 0.18 | 4.63 |
| HSPB6 | 0.19 | 6.70 | CD27 | 0.10 | 4.62 |
| MFGE8 | −0.21 | 6.68 | SPON1 | 0.10 | 4.58 |
| SMPD1 | −0.15 | 6.59 | IGFBP-2 | 0.15 | 4.58 |
| FLT1 | 0.09 | 6.29 | DNER | −0.07 | 4.57 |
| CTSD | −0.13 | 6.06 | RARRES1 | 0.09 | 4.57 |
| CD209 | −0.11 | 5.85 | Dkk-4 | 0.15 | 4.49 |

Figure 2B:
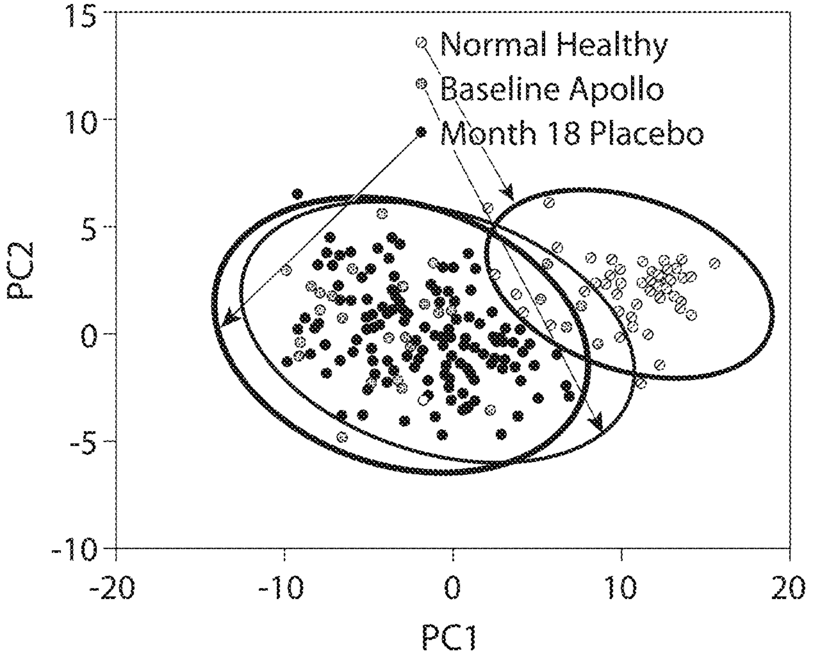
Figure 2C:
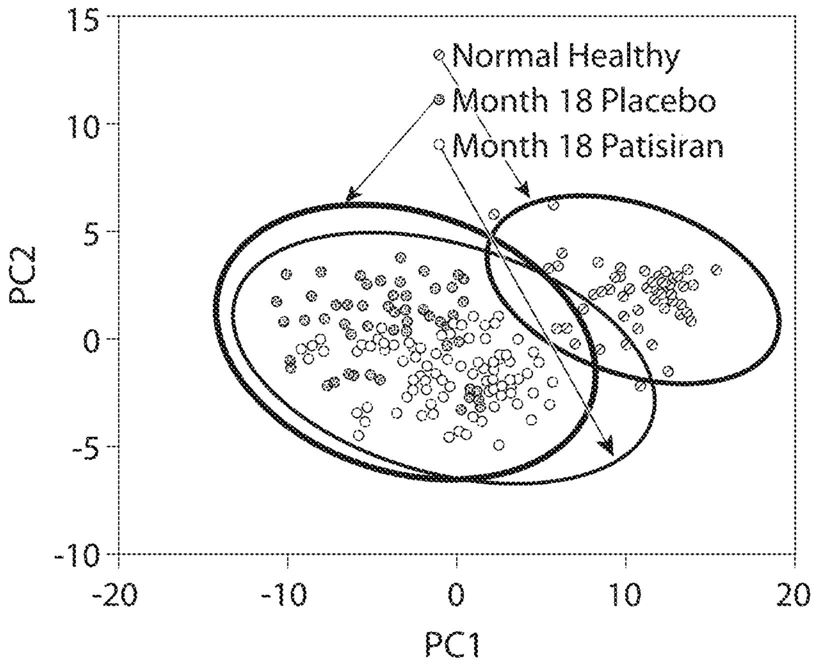
Figure 2D:
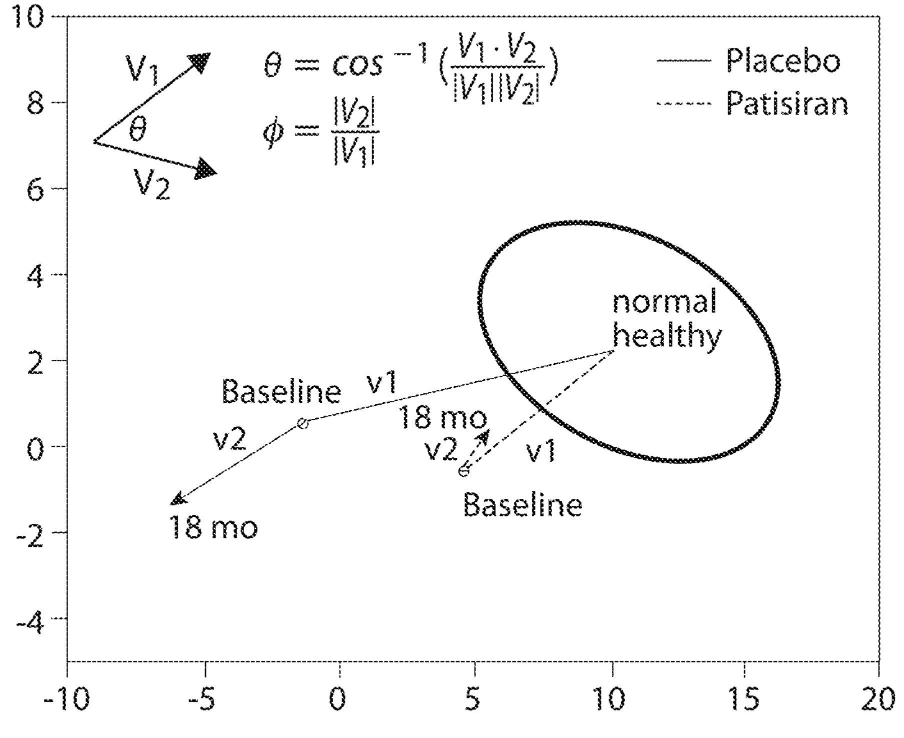
Figure 2E:
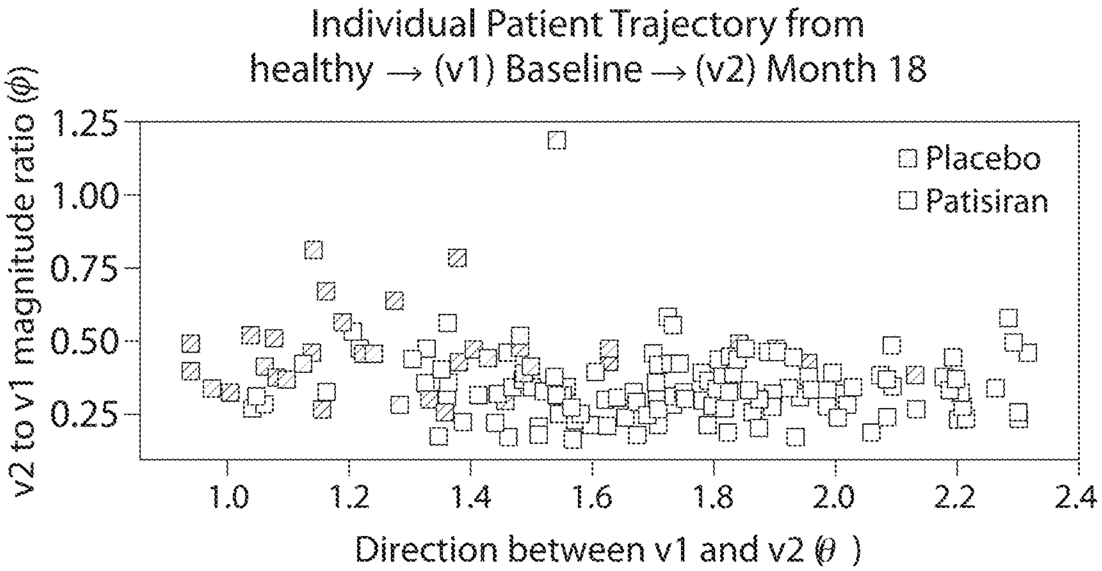

To elucidate whether a systemic plasma proteomic shift with disease and reversal with patisiran could be observed, principal component analysis was used to compare healthy samples to baseline hATTR disease samples using the 66 most significant proteins found in the mixed model analysis (Table 2). Projecting each subject's data onto the two principal components that account for the most variance reveals a distinct separation between healthy controls and patients with hATTR with polyneuropathy entering the APOLLO trial (FIG. 2*a*), with most of the separation being driven by the first principal component (PC1). The proteomes of placebo treated patients at month 18 were projected onto the same principal components and the 99.9% confidence ellipse shows a leftward movement along PC1, suggesting that the proteome is further differentiating from healthy controls (FIG. 2*b*). The placebo and patisiran treated groups were compared at month 18 and showed that plasma proteomes of patisiran treated patients are more similar to those of healthy subjects compared to placebo treated patients (FIG. 2*c*). Since there is significant heterogeneity in the proteome of patients at baseline disease, individual patient trajectories were also captured in 66-dimensional space. For each patient, the course of their disease progression or regression were defined using two metrics, one for the rate (ϕ) and a second for whether the proteome moved away or towards the healthy controls (⊖; see FIG. 2*d* legend). Plotting these two parameters clearly separates patisiran and placebo treated patients (FIG. 2*e*), emphasizing the distinct differences in the proteomes of the two groups at 18 months, reflective of changes in disease status.

Figure 3A:
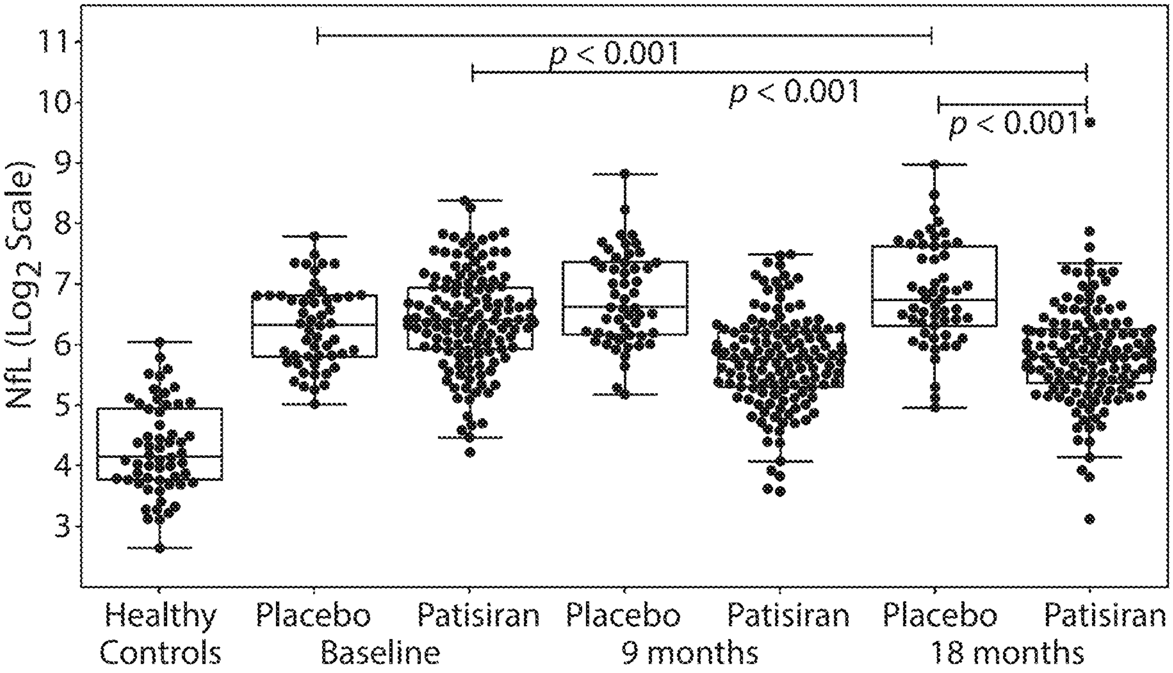
FIGS. 3A-3D depict that NfL levels change over time patients on placebo and patisiran treatment.

Neurofilament (NfL), the most significantly changed protein in the analysis when comparing placebo and patisiran treated hATTR patients over time, was further investigated. Patients diagnosed with hATTR with polyneuropathy had over 4-fold higher levels of NfL in their plasma relative to healthy controls (FIG. 3*a*; $\log_2$ scale). As expected, levels of NfL at baseline did not differ between the patisiran and placebo groups. Interestingly, the patisiran-treated group had a significant decline in NfL levels at 9 months that was sustained at 18 months whereas the levels of NfL in the placebo group increased at both 9 and 18 months relative to baseline. At month 18, patients treated with patisiran had 2-fold lower NfL levels than placebo treated patients. Treatment with patisiran significantly lowered NfL levels in patients with hATTR toward levels observed in healthy controls.

Figure 3C:
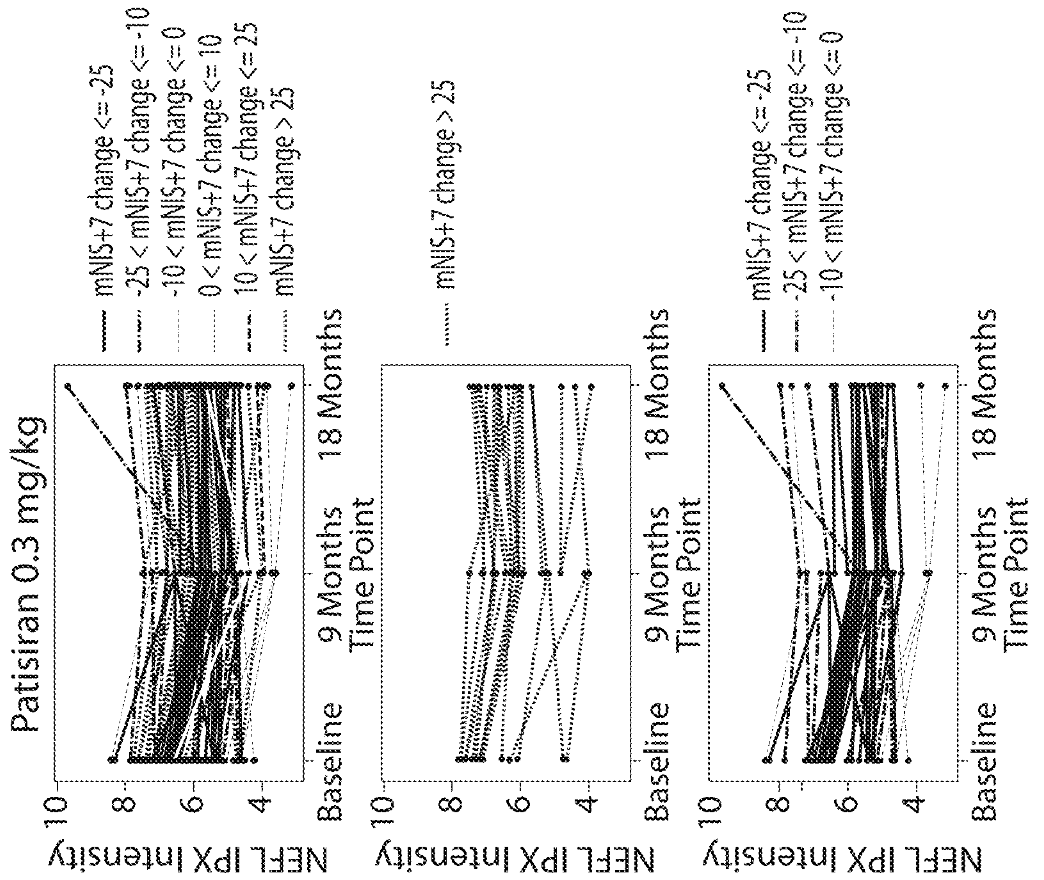
Figure 3B:
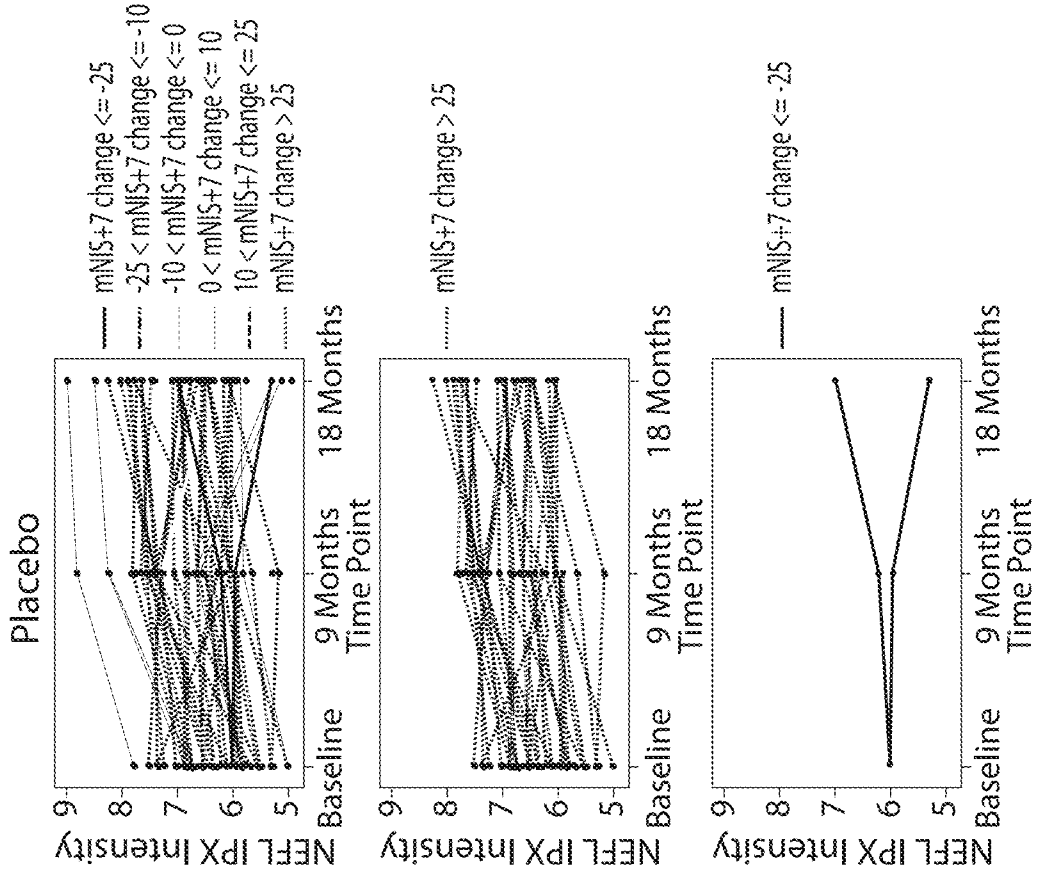
Figure 3D:
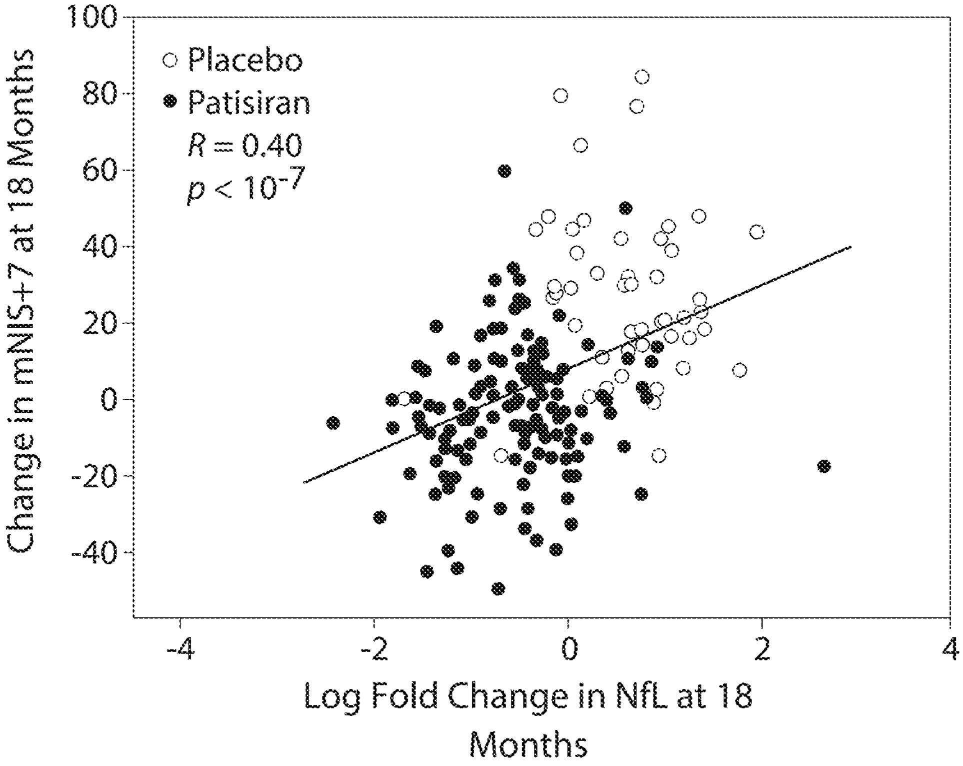

To assess intraindividual variability, levels of NfL were plotted for each patient over time, separated by whether they received placebo (FIG. 3*b*) or patisiran treatment (FIG. 3*c*) and coded by whether patients had a worsening of disease symptoms (change in mNIS+7>0) or improvement of disease symptoms (change in mNIS+7<0) at 18 months. Consistent with the previous analysis, patients receiving placebo showed increasing levels of NfL over time, whereas patients receiving patisiran treatment showed decreasing levels of NfL and these changes largely correlated with whether patients had a corresponding decrease or increase in their neuropathy impairment score. Plotting each patient's change in mNIS+7 against change in NfL levels at 18 months shows a correlation of 0.34 (FIG. 3*d*) indicating that decreasing levels of NfL are associated with an improvement in the neuropathy impairment score.

Figure 4A:
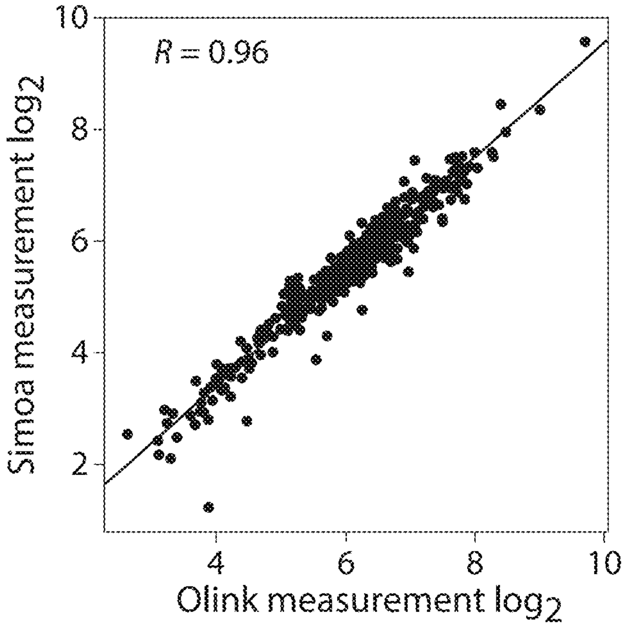
FIGS. 4A-4E depict that the quantitative measurement of NfL shows the potential of plasma NfL levels to distinguish between healthy patients and patients with hATTR amyloidosis with polyneuropathy.
Figure 4B:
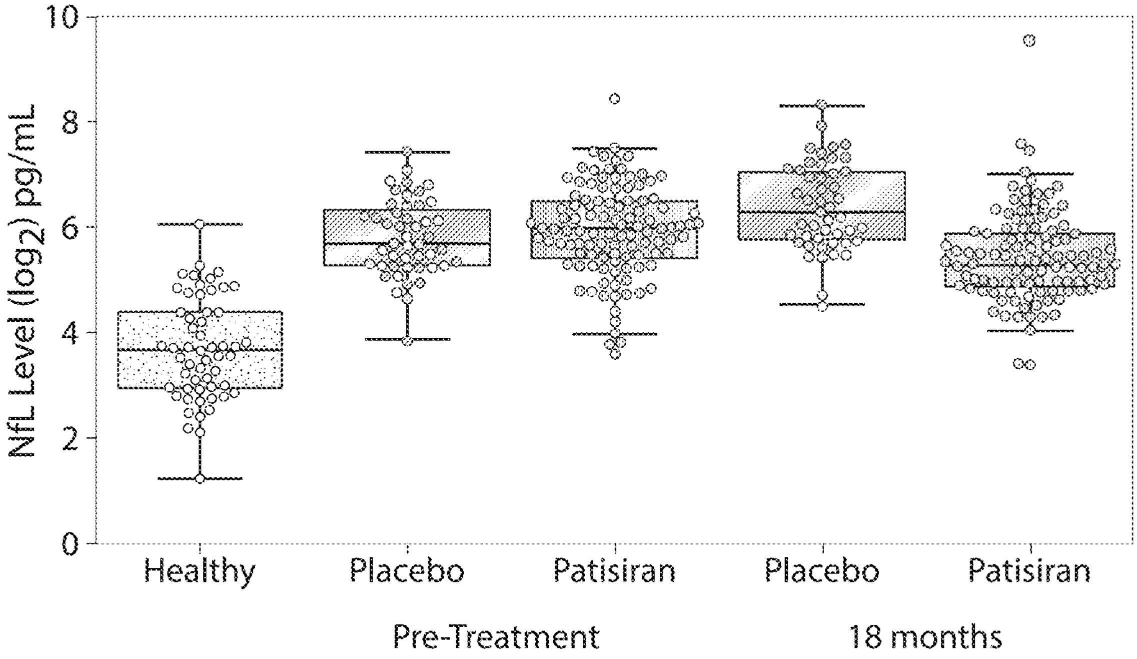
Figure 4C:
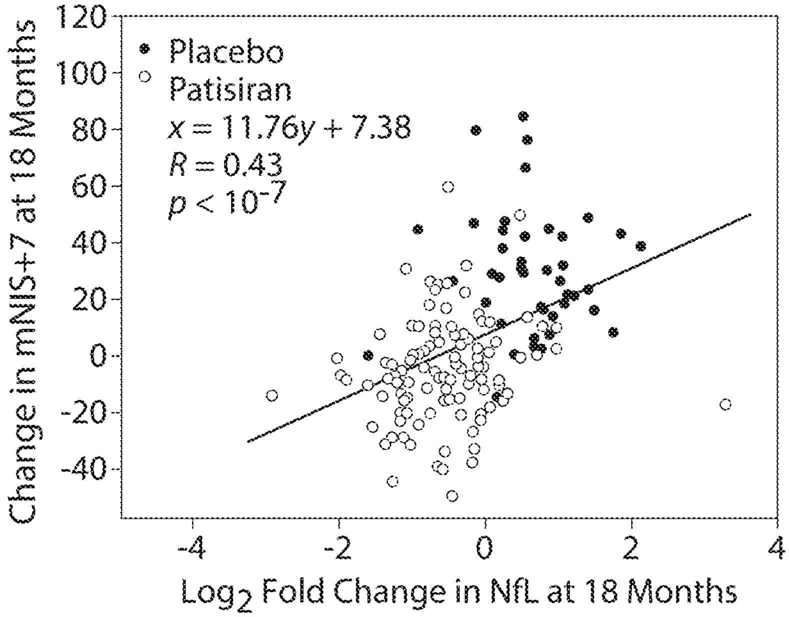
Figure 4D:
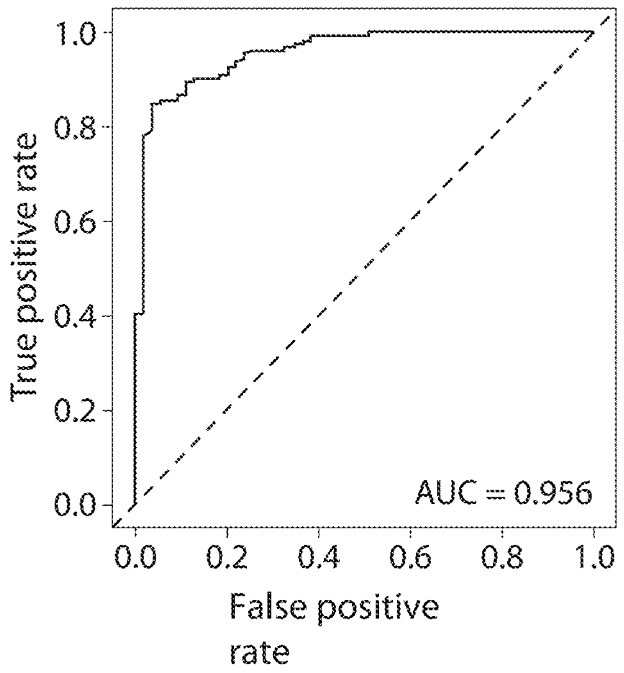
Figure 4E:
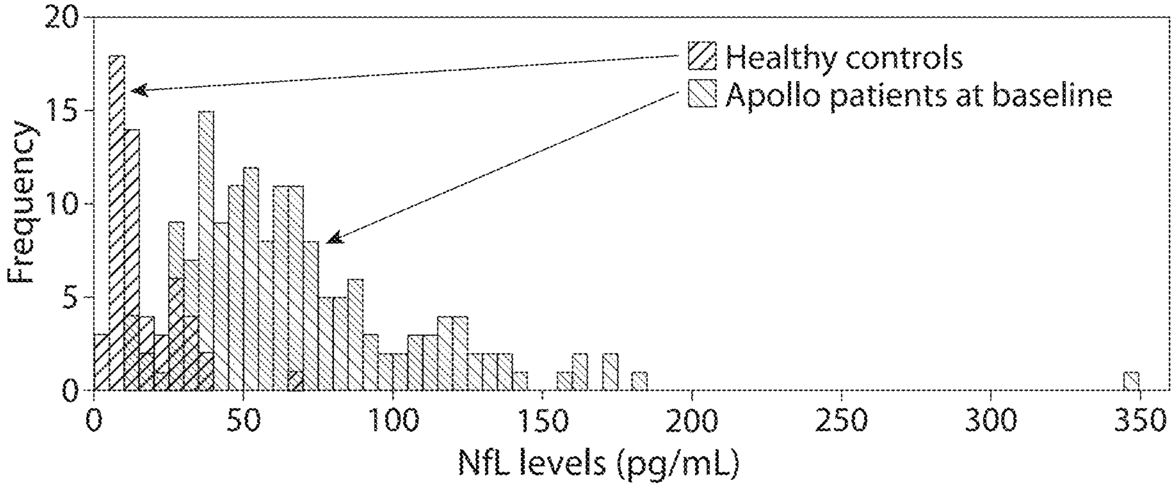

The initial NfL measurements were further validated with a quantitative assay to provide absolute plasma concentrations of NfL in healthy controls and hATTR amyloidosis patient samples from APOLLO at baseline and 18 months (FIG. 4*a*-4*e*). There was a very strong correlation between the two assays used to measure plasma NfL levels (FIG. 4*a*; R=0.96). NfL levels in healthy individuals were on average 16.3 μg/mL, consistent with published reports (Disanto et al, 2017; std. dev. =12.0 μg/mL; FIG. 4*b*). Patients with hATTR amyloidosis with polyneuropathy had plasma NfL levels that were approximately 4-fold higher at baseline, 69.4 μg/mL (std. dev. =42.1 μg/mL) which decreased following patisiran treatment (48.8 μg/mL±29.9 μg/mL) and increased in the placebo group at 18 months (99.5 pg/mL±60.1 μg/mL). One outlier in the patisiran-treated group, with 747 μg/mL of NfL that was excluded from the calculations (FIG. 4*b*, 4*e*). Consistent with the initial plasma NfL measurements, there is a strong correlation was observed for each patient between change in mNIS+7 and change in plasma NfL levels at 18 months (correlation of 0.43; FIG. 4*c*), suggesting that improvements in polyneuropathy are associated with a decrease in plasma NfL levels. To determine whether plasma NfL levels could discriminate between healthy individuals and patients with hATTR amyloidosis with polyneuropathy, a receiver operator curve was used yielding an area under the curve of 0.956 (FIG. 4*d*) and the distribution of each was plotted (FIG. 4*e*). Average NfL levels described here in patients with hATTR amyloidosis with polyneuropathy (69.4 μg/mL) are higher than those observed for other peripheral nerve disorders (CIDP 42 μg/mL, CMT 26 μg/mL). Based on the current data, a cutoff of 37 μg/mL can be considered a conservative threshold to distinguish between healthy and hATTR amyloidosis patients, at which the false positive rate is 3.6% and the true positive rate is 84.9%.

Figure 5A:
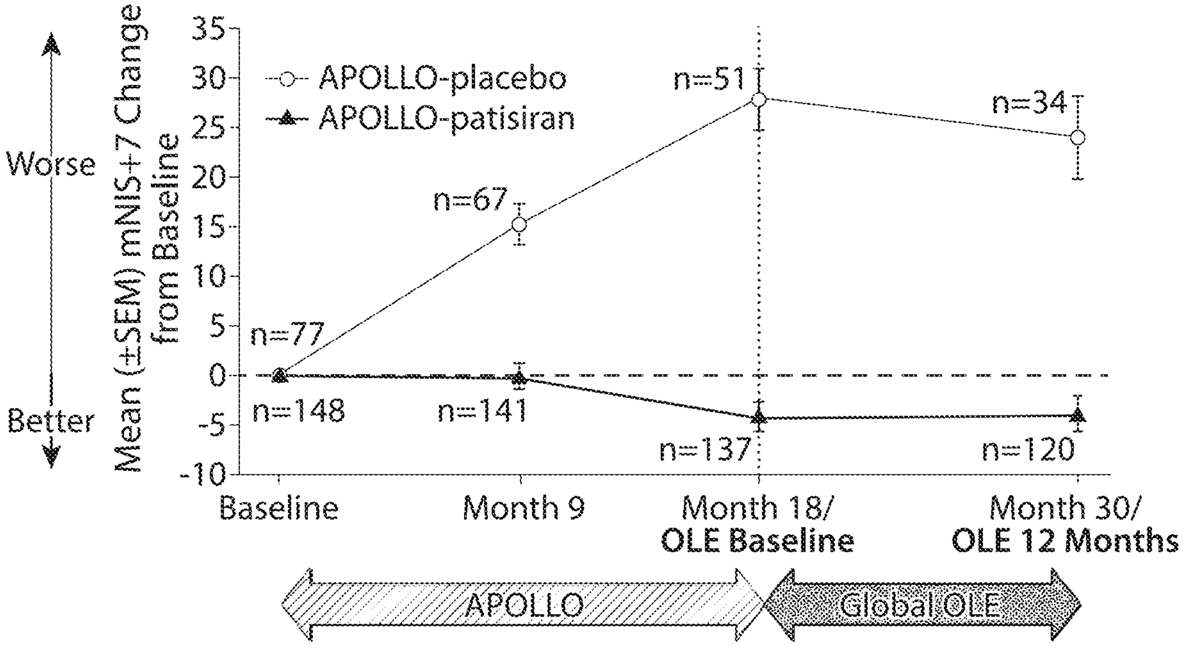
FIGS. 5A-5C depict that NfL levels change over time in patients on placebo and patisiran treatment in a global open label extension (OLE) study.
Figure 5B:
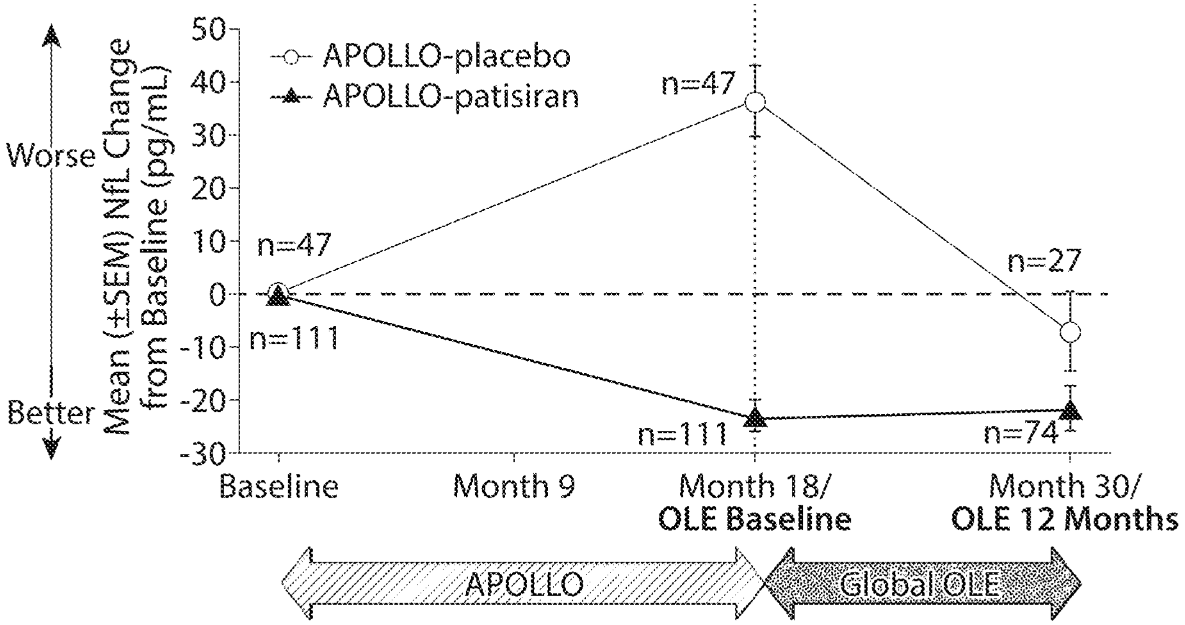
Figure 5C:
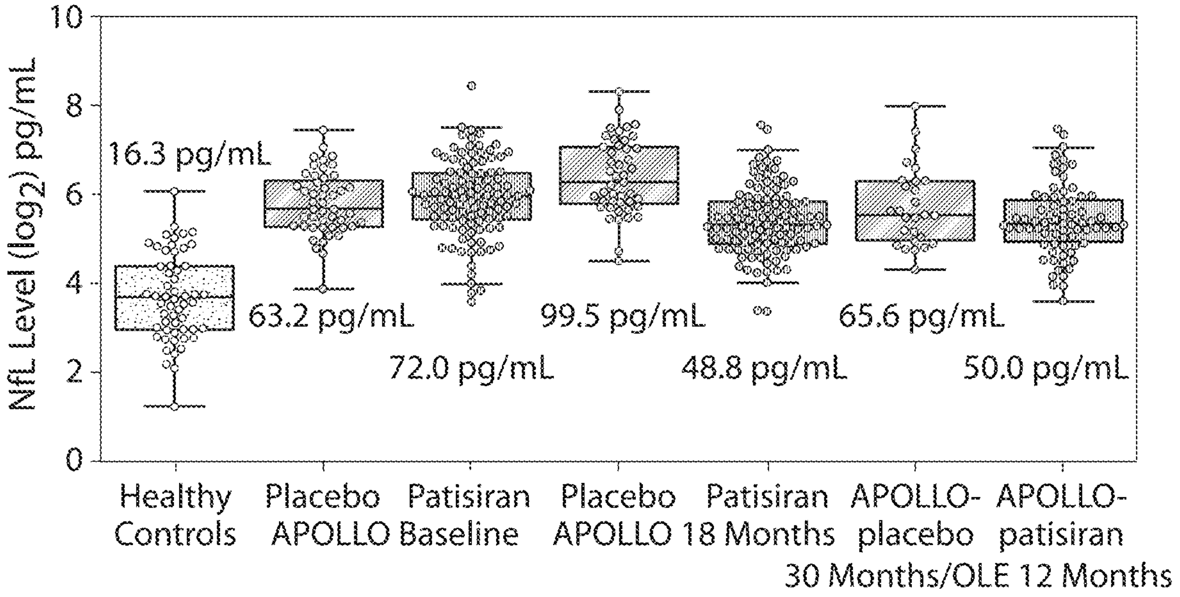

Patients who met eligibility criteria from the APOLLO studies were able to roll over into the multicenter, international, open-label extension (OLE) study to evaluate the long-term safety and efficacy of patisiran. Assessments included mNIS+7 and NfL levels after 12 months in the OLE (after initial treatment with patisiran (n=120) or placebo (n=34)). After 12 months of additional patisiran treatment in the Global OLE, APOLLO patisiran patients demonstrated durable improvement in neuropathy versus their parent-study baselines, as seen by mean negative change from baseline in modified neuropathy impairment score+7 (mNIS+7). The rapid trajectory of polyneuropathy progression among the APOLLO placebo patients halted once patisiran treatment was initiated in the Global OLE, with an improvement in mNIS+7 score over the 12 months they received patisiran in the Global OLE (FIG. 5*a*). NfL levels remained steady after 12 months in the Global OLE for the APOLLO-patisiran patients (mean 48.8 pg/mL vs 50.0

μg/mL), whereas NfL levels decreased significantly after 12 months of patisiran treatment in the APOLLO-placebo patients (mean 99.5 μg/mL vs 65.6 μg/mL; p-value<0.001) (FIGS. 5*b* and 5*c*). These data further demonstrate the correlation of a neuropathy score with plasma NfL level.

Example 2. Treatment of Cardiovascular TTR Amyloidosis with Monitoring of NfL Levels A subject diagnosed with cardiovascular TTR amyloidosis, with or without a TTR mutation associated with TTR amyloidosis, but without meeting the criteria for Stage 1 FAP is treated with tafamidis per the label indication. A sample from the subject, e.g., blood or plasma derived therefrom, is tested at regular intervals, e.g., every six months, for biomarkers related to disease progression including, but not limited to, NfL. During the course of treatment, a significant increase in NfL is observed as compared to an earlier sample from the same subject. The level may also be determined to be elevated as compared to a population control. Provided with this elevated NfL level, treatment with tafamidis is discontinued as treatment with patisiran is initiated. The NfL level of the subject continues to be monitored. Over time, the NfL level of the subject is found to decrease, indicating that patisiran is effective in treating TTR amyloid polyneuropathy.

Example 3. Monitoring of a Subject with a TTR Mutation Associated with TTR Amyloidosis Through genetic testing, a subject is identified as having a TTR mutation associated with TTR amyloidosis. Due to the variability in the age of onset of TTR amyloidosis, it is determined that the subject will not start treatment with an agent for the treatment of TTR amyloidosis until the presentation of at least one sign or symptom of the disease. The subject is routinely monitored for the presence of one or more biomarkers related to various manifestations of TTR amyloidosis, including NfL and NT-proBNP. Cardiac function and imaging tests are also performed. Concurrently, increases in both NfL and NT-proBNP are observed with a corresponding decrease in cardiac function. Treatment with an agent that reduces expression of TTR, e.g., vutrisiran, is initiated in the subject.

Example 4. Assessment of NfL Levels in Subjects with hATTR Amyloidosis with Cardiomyopathy The ENDEAVOR study was a phase 3 study designed to evaluate the safety and efficacy of revusiran in patients with transthyretin (TTR) mediated Familial Amyloidotic Cardiomyopathy, a form of hATTR amyloidosis. Inclusion criteria included a documented TTR mutation, the presence of amyloid deposits in cardiac or non-cardiac tissue, a medical history of heart failure, and evidence of cardiac involvement by echocardiogram. The study enrolled 206 subjects, 140 subjects received revusiran and 66 received placebo (see, e.g., Judge et al., Cardiovascular Drugs and Therapy (2020) 34:357-370). Polyneuropathy disability scores were as follows (from Table 1 of Judge et al.):

| PND score, n (%) | Placebo (n = 66) | Revusiran (n = 140) | Total (n = 206) |
|---|---|---|---|
| 0 | 35 (53.0) | 62 (44.3) | 97 (47.1) |
| 1 | 20 (30.3) | 55 (39.3) | 75 (36.4) |
| 2 | 11 (16.7) | 23 (16.4) | 34 (16.5) |

Figure 6A:
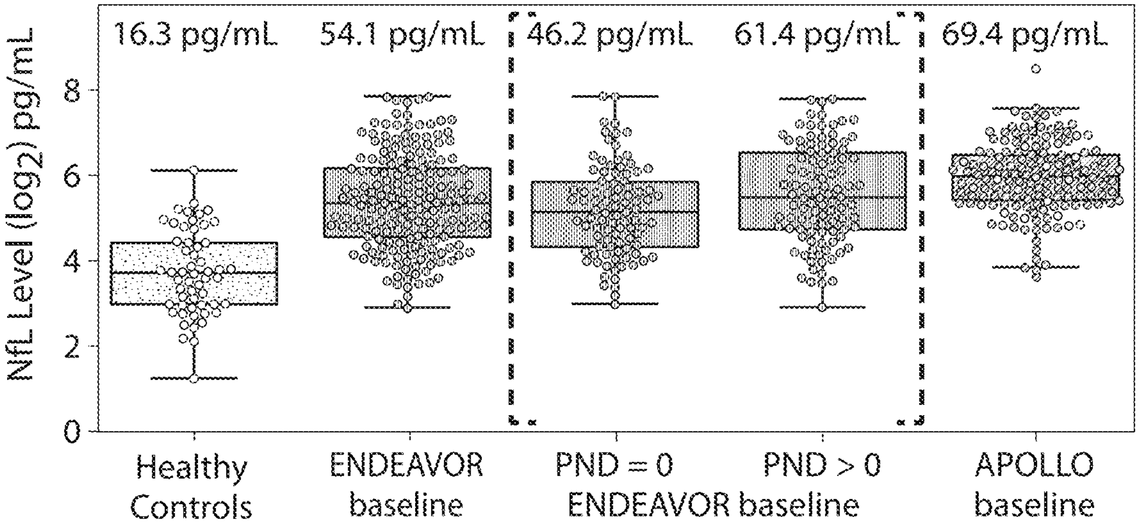
FIGS. 6A-6B depict that NfL levels are increased in the absence of clinically significant neurological symptoms in hTTR amyloidosis.

NfL levels were measured at baseline in patients enrolled in a Phase 3 study of hATTR amyloidosis with cardiomyopathy. Revusiran treatment was stopped after a median of 6.71 months due to an observed mortality imbalance between treatment arms, so no NfL level was assessed at the close of the study. Levels of NfL were significantly elevated in ENDEAVOR patients relative to healthy controls (mean 54.1 μg/mL vs 16.3 μg/mL; p<0.001) (FIG. 6*a*). Patients with a PND score greater than 0 had higher serum NfL levels than those having a PND score of 0. As the presence of polyneuropathy was required for inclusion in the APOLLO study, the NfL levels were found to be higher than the baseline value in ENDEAVOUR, despite the average ENDEAVOR patient being older than the average APOLLO patient (68 years vs. 61 years).

Figure 6B:
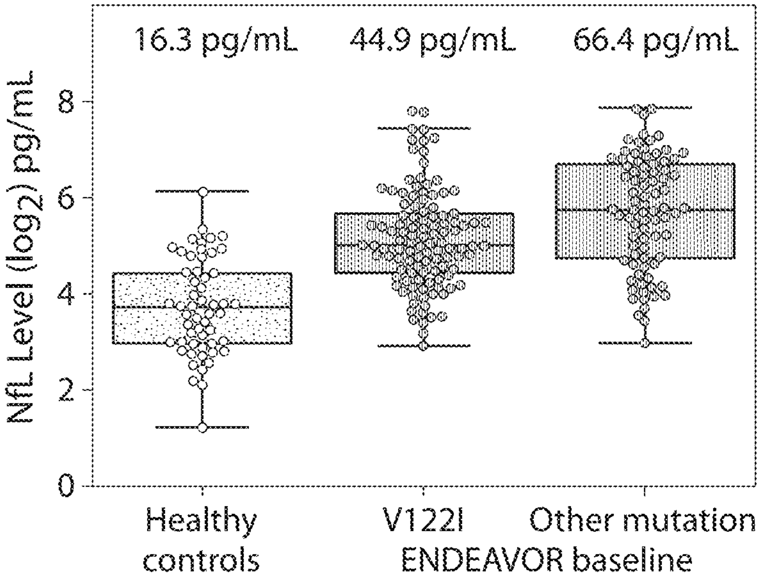

The V122I mutation in TTR is typically associated with cardiac manifestations, rather than neuropathy manifestations of hATTR amyloidosis. Patients with V122I mutations were found to have elevated plasma NfL as compared to healthy controls, albeit lower that in patients having non-V122I mutations (FIG. 6*b*).

These data demonstrate the utility of an NfL level to monitor progression of TTR amyloidosis even prior to the development of significant neurological symptoms of the disease or in patients with mutations typically associated with cardiac manifestations of TTR amyloidosis.

```
SELECTED AMINO ACID SEQUENCES
NFL
LOCUS NP_006149 543 aa linear PRI 21 AUG. 2019
DEFINITION neurofilament light polypeptide [Homo sapiens]
ACCESSION NP_006149.2
   1 mssfsyepyy stsykrryve tprvhissvr sgystarsay ssysapvsss lsvrrsysss

  61 sgslmpslen ldlsqvaais ndlksirtqe kaqlqdlndr fasfiervhe leqqnkvlea

 121 ellvlrqkhs epsrfralye qeirdlrlaa edatnekqal qgeregleet lrnlqaryee

 181 evlsredaeg rlmearkgad eaalaraele kridslmdei sflkkvheee iaelqaqiqy

 241 aqisvemdvt kpdlsaalkd iraqyeklaa knmqnaeewf ksrftvltes aakntdavra

 301 akdevsesrr llkaktleie acrgmneale kqlqeledkq nadisamqdt inklenelrt

 361 tksemarylk eyqdllnvkm aldieiaayr kllegeetrl sftsvgsits gysqssqvfg
```

-continued 421 rsaygglqts sylmstrsfp syytshvqee qieveetiea akaeeakdep psegeaeeee 481 kdkeeaeeee aaeeeeaake eseeakeeee ggegeegeet keaeeeekkv egageeqaak 541 kkd (SEQ ID NO: 1)

LOCUS AAH66952 284 aa linear PRI 19 MAR. 2009
DEFINITION NEFL protein [*Homo sapiens*].
ACCESSION AAH66952.1
DBSOURCE accession BC066952.1
1 mssfsyepyy stsykrryve tprvhissvr sgystarsay ssysapvsss lsvrrsysss 61 sgslmpslen ldlsqvaais ndlksirtqe kaqlqdlndr fasfiervhe leqqnkvlea 121 ellvlrqkhs epsrfralye qeirdlrlaa edatnekqal qgeregleet lrnlqaryee 181 evlsredaeg rlmearkgak ntdavraakd evsesrrllk aktleieacr gmnealekql 241 qeledkqnad isvmqdtink lenelrttks emarylkeyq dllt (SEQ ID NO: 10)

LOCUS AAH39237 543 aa linear PRI 18 MAR. 2009
DEFINITION Neurofilament, light polypeptide [*Homo sapiens*].
ACCESSION AAH39237.1
DBSOURCE accession BC039237.1
1 mssfsyepyy stsykrryve tprvhissvr sgystarsay ssysapvsss lsvrrsysss 61 sgslmpslen ldlsqvaais ndlksirtqe kaqlqdlndr fasfiervhe leqqnkvlea 121 ellvlrqkhs epsrfralye qeirdlrlaa edatnekqal qgeregleet lrnlqaryee 181 evlsredaeg rlmearkgad eaalaraele kridslmdei sflkkvheee iaelqaqiqy 241 aqisvemdvt kpdlsaalkd iraqyeklaa knmqnaeewf ksrftvltes aakntdavra 301 akdevsesrr llkaktleie acrgmneale kqlqeledkq nadisamqdt inklenelrt 361 tksemarylk eyqdllnvkm aldieiaayr kllegeetrl sftsvgsits gysqssqvfg 421 rsaygglqts sylmstrsfp syytshvqee qieveetiea akaeeakdep psegeaeeee 481 kdkeeaeeee aaeeeeaake eseeakeeee ggegeegeet keaeeeekkv egageeqaak 541 kkd (SEQ ID NO: 1)

RSPO3
LOCUS NP_116173 272 aa linear PRI 10 JUL. 2019
DEFINITION R-spondin-3 precursor [*Homo sapiens*].
ACCESSION NP_116173.2
DBSOURCE REFSEQ: accession NP_032784.5
1 mhlrliswlf iilnfmeyig sqnasrgrrq rrmhpnvsqg cqggcatcsd yngclsckpr 61 lffalerigm kqigvclssc psgyygtryp dinkctkcka dcdtcfnknf ctkcksgfyl 121 hlgkcldncp egleannhtm ecvsivhcev sewnpwspct kkgktcgfkr gtetrvreii 181 qhpsakgnlc pptnetrkct vqrkkcqkge rgkkgrerkr kkpnkgeske aipdsksles 241 skeipeqren kqqqkkrkvq dkqksvsvst vh (SEQ ID NO: 11)

LOCUS XP_016866868 203 aa linear PRI 13 JUN. 2019
DEFINITION R-spondin-3 isoform X2 [*Homo sapiens*].
ACCESSION XP_016866868.1
DBLINK BioProject: PRJNA168
DBSOURCE REFSEQ: accession XP_1017011379.1
1 mkqigvclss cpsgyygtry pdinkctkck adcdtcfnkn fctkcksgfy lhlgkcldnc 61 pegleannht mecvsivhce vsewnpwspc tkkgktcgfk rgtetrvrei iqhpsakgnl 121 cpptnetrkc tvqrkkcqkg ergkkgrerk rkkpnkgesk eaipdsksle sskeipeqre 181 nkqqqkkrkv qdkqksvsvs tvh (SEQ ID NO: 12)

LOCUS XP_016866867 224 aa linear PRI 13 JUN. 2019
DEFINITION R-spondin-3 isoform X1 [*Homo sapiens*].
ACCESSION XP_016866867.1
DBLINK BioProject: PRJNA168
DBSOURCE REFSEQ: accession XM_1017011378.1
1 mhlrliswlf iilnfmeyig sqnasrgrrq rrmhpnvsqg cqggcatcsd yngclsckpr 61 lffalerigm kqigvclssc psgyygtryp dinkctkcka dcdtcfnknf ctkcksgfyl -continued

```
 121 hlgkcldncp egleannhtm ecvsivhcev sewnpwspet kkgktegfkr gtetrvreii

 181 qhpsakgnlc pptnetrkct vqrkkcqkge rgrtsrgder cfnh (SEQ ID NO: 13)

CCDC80
LOCUS AAH86876 553 aa linear PRI 18 AUG. 2006
DEFINITION CCDC80 protein, partial [Homo sapiens].
ACCESSION AAH86876.1
   1 mtwrmgprft mllamwlvcg sephphatir gshggrkvpl vspdssrpar flrhtgrsrg

  61 ierstleepn lqplqrrrsv pvlrlarpte pparsdinga avrpeqrpaa rgspremird

 121 egssarsrml rfpsgssspn ilasfagknr vwvisaphas egyyrlmmsl lkddvycela

 181 erhiqqivlf hqageeggkv rritsegqil eqpldpslip klmsflklek gkfgmvllkk

 241 tlqveerypy pvrleamyev idqgpirrie kirqkgfvqk ckasgvegqv vaegndgggg

 301 agrpslgsek kkedprraqv pptresrvkv lrklaatapa lpqppstpra ttlppapatt

 361 vtrstsravt vaarpmttta fpttqrpwtp spshrppttt evitarrpsv senlyppsrk

 421 dqhrerpqtt rrpskatsle sftnapptti sepstraagp grfrdnrmdr rehghrdpnv

 481 vpgppkpake kppkkkaqdk ilsneyeeky dlsrptasql edelqvgnvp lkkakeskkh

 541 eklekpekkk ekk (SEQ ID NO: 14)

LOCUS AAH73164 331 aa linear PRI 18 AUG. 2006
DEFINITION CCDC80 protein, partial [Homo sapiens].
ACCESSION AAH73164.1
DBSOURCE accession BC073164.1
   1 egkrrlllit apkaennmyv qqrdeylesf ckmatrkisv itifgpvnns tmkidhfqld

  61 nekpmrvvdd edlvdqrlis elrkeygmty ndffmvltdv dlrvkqyyev pitmksvfdl

 121 idtfqsrikd mekqkkegiv ckedkkqsle nflsrfrwrr rllvisapnd edwaysqqls

 181 alsgqacnfg lrhitilkll gvgeevggvl elfpinggsv veredvpahl vkdirnyfqv

 241 speyfsmllv gkdgnvkswy pspmwsmviv ydlidsmqlr rqemaiqqsl gmrcpedeya

 301 gygyhsyhqg yqdgyqddyr hhesyhhgyp y (SEQ ID NO: 15)

LOCUS AAH42105 85 aa linear PRI 6 JUN. 2006
DEFINITION CCDC80 protein [Homo sapiens].
ACCESSION AAH42105.1
DBSOURCE accession BC042105.1
   1 mllvgkdgnv kswypspmws mvivydlids mqlrrqemai qqslgmrcpe deyagygyhs

  61 yhqpyqdgyq ddyrhhesyh hgypy (SEQ ID NO: 16)

EDA2R
LOCUS NP_001186616 297 aa linear PRI 6 AUG. 2019
DEFINITION tumor necrosis factor receptor superfamily member 27 isoform 1
[Homo sapiens].
ACCESSION NP_001186616.1
DBSOURCE REFSEQ: accession NM_001199687.2
   1 mdcqeneywd qwgrcvtcqr cgpgqelskd cgygeggday ctacpprryk sswghhrcqs

  61 citcavinrv qkvnctatsn avcgdclprf yrktrigglq dqecipctkq tptsevqcaf

 121 qlslveadap tvppqeatlv alvssllvvf tlaflglffl yckqffnrhc qrggllqfea

 181 dktakeeslf pvppsketsa esqvsenifq tqplnpiled dcsstsgfpt qesftmasct

 241 seshshwvhs piecteldlq kfsssasytg aetlggntve stgdrlelnv pfevpsp (SEQ

     ID NO: 17)

LOCUS NP_001229239 318 aa linear PRI 6 AUG. 2019
DEFINITION tumor necrosis factor receptor superfamily member 27 isoform 2
[Homo sapiens].
ACCESSION NP_001229239.1
DBSOURCE REFSEQ: accession NM_001242310.1
   1 mdcqeneywd qwgrcvtcqr cgpgqelskd cgygeggday ctacpprryk sswghhrcqs

  61 citcavinrv qkvnctatsn avcgdclprf yrktrigglq dqecipctkq tptsevqcaf

 121 qlslveadap tvppqeatlv alvssllvvf tlaflglffl yckqffnrhc qrekliifsd
```

-continued 181 pvpaslnlip efaggllqfe adktakeesl fpvppskets aesqvsenif qtqplnpile 241 ddcsstsgfp tqesftmasc tseshshwvh spiecteldl qkfsssasyt gaetlggntv 301 estqdrleln vpfevpsp (SEQ ID NO: 18)

LOCUS NP_001311128 173 aa linear PRI 8 AUG. 2019
DEFINITION tumor necrosis factor receptor superfamily member 27 isoform 3 [*Homo sapiens*].
ACCESSION NP_001311128.2
DBSOURCE REFSEQ: accession NM_001324199.2
1 mstgtngdgv spangvvldr syprclpvel sggrythsap sgghtcctgg llqfeadkta 61 keeslfpvpp sketsaesqv senifqtqpl npileddcss tsgfptqesf tmasctsesh 121 shwvhspiec teldlqkfss sasytgaetl ggntvestgd rlelnvpfev psp (SEQ ID NO: 19)

LOCUS NP_001311130 265 aa linear PRI 8 AUG. 2019
DEFINITION tumor necrosis factor receptor superfamily member 27 isoform 4 [*Homo sapiens*].
ACCESSION NP_001311130.2
DBSOURCE REFSEQ: accession NM_001324201.2
1 mstgtngdgv spangvvldr sypriwmer vemptaqpal lagtkaagat tdvrvaspvl 61 ssivfrrsta qlplmlsvgt vcpgafqlsl veadtptvpp qeatlvalvs sllvvftlaf 121 lglfflyckq ffnrhcqrva ggllqfeadk takeeslfpv ppsketsaes qvsenifqtq 181 plnpileddc sstsgfptqe sftmasctse shshwvhspi ecteldlqkf sssasytgae 241 tlggntvest gdrlelnvpf evpsp (SEQ ID NO: 20)

LOCUS NP_001311131 107 aa linear PRI 9 AUG. 2019
DEFINITION tumor necrosis factor receptor superfamily member 27 isoform 5 [*Homo sapiens*].
ACCESSION NP_001311131.2
1 mstgtngdgv spangvvldr syprclpvel sggrythsap sgghtcctgg llqfeadkta 61 keeslfpvpp sketsaesqv swapgslaql fsldsvpipq qqqgpem (SEQ ID NO: 21)

LOCUS NP_001311133 134 aa linear PRI 7 AUG. 2019
DEFINITION tumor necrosis factor receptor superfamily member 27 isoform 6 [*Homo sapiens*].
ACCESSION NP_001311133.2
DBSOURCE REFSEQ: accession NM_001324204.2
1 mgtvchlptv wswtgaiqga fqlslveadt ptvppqeatl valvssllvv ftlaflglff 61 lyckqffnrh cqrvaggllq feadktakee slfpvppske tsaesqvswa pgslaqlfsl 121 dsvpipqqqq gpem (SEQ ID NO: 22)

LOCUS NP_001311134 132 aa linear PRI 8. AUG. 2019
DEFINITION tumor necrosis factor receptor superfamily member 27 isoform 7 [*Homo sapiens*].
ACCESSION NP_001311134.2
DBSOURCE REFSEQ: accession NM_001324205.2
1 mgtvchlptv wswtgaiqga fqlslveadt ptvppqeatl valvssllvv ftlaflglff 61 lyckqffnrh cqrggllqfe adktakeesl fpvppskets aesqvswapg slaqlfslds 121 vpipqqqqgp em (SEQ ID NO: 23)

LOCUS NP_001311135 299 aa linear PRI 7 AUG. 2019
DEFINITION tumor necrosis factor receptor superfamily member 27 isoform 8 [*Homo sapiens*].
ACCESSION NP_001311135.2
DBSOURCE REFSEQ: accession NM_001324206.2
1 mdcqeneywd qwgrcvtcqr cgpgqelskd cgygeggday ctacpprryk sswghhrcqs 61 citcavinrv qkvnctatsn avcgdclprf yrktrigglq dqecipctkq tptsevqcaf 121 qlslveadtp tvppqeatlv alvssllvvf tlaflglffl yckqffnrhc qrvaggllqf 181 eadktakees lfpvppsket saesqvseni fqtqplnpil eddcsstsgf ptqesftmas 241 ctseshshwv hspiecteld lqkfsssasy tgaetlggnt vestgdrlel nvpfevpsp -continued (SEQ ID NO: 24)

LOCUS NP_068555 297 aa linear PRI 6 AUG. 2019
DEFINITION tumor necrosis factor receptor superfamily member 27 isoform 1 [*Homo sapiens*].
ACCESSION NP_068555.2
DBSOURCE REFSEQ: accession NM_021783.5

```
    1 mdcqeneywd qwgrcvtcqr cgpgqelskd cgygeggday ctacpprryk sswghhrcqs

   61 citcavinrv qkvnctatsn avcgdclprf yrktrigglq dqecipctkq tptsevqcaf

  121 qlslveadtp tvppqeatlv alvssllvvf tlaflglffl yckqffnrhc qrggllqfea

  181 dktakeeslf pvppsketsa esqvsenifq tqplnpiled dcsstsgfpt qesftmasct

  241 seshshwvhs piecteldlq kfsssasytg aetlggntve stgdrlelnv pfevpsp (SEQ

      ID NO: 25)
```

NT-proBNP
LOCUS NP_002512 134 aa linear PRI 30 JUN. 2019
DEFINITION natriuretic peptides B preproprotein [*Homo sapiens*].
ACCESSION NP_002512.1
DBSOURCE REFSEQ: accession NM_002521.3

```
    1 mdpqtapsra lllllflhla flggrshplg spgsasdlet sglqeqrnhl qgklselqve

   61 qtsleplqes prptgvwksr evategirgh rkmvlytlra prspkmvqgs gcfgrkmdri

  121 ssssglgckv lrrh (SEQ ID NO: 26)
```

---

The invention claimed is:

1. A method of treating cardiovascular transthyretin (TTR) amyloidosis in a human subject in need thereof, the method comprising:

(a) determining the level of neurofilament light chain (NfL) in a biological sample from the subject;

(b) comparing the level of NfL determined in step (a) to a reference level of NfL;

(c) identifying the subject as having an elevated level of NfL as compared to the reference level of NfL; and (d) administering an RNAi agent or an antisense oligonucleotide that reduces expression of TTR to the subject that has been identified in step (c) as having an elevated level of NfL, thereby treating cardiovascular transthyretin (TTR) amyloidosis in the subject.

2. The method of claim 1, wherein the RNAi agent or the antisense oligonucleotide is selected from the group consisting of patisiran, vutrisiran, inotersen and ION-TTR-LRx.

3. The method of claim 1, (a) wherein the subject has not been previously diagnosed with hTTR amyloidosis polyneuropathy;

(b) wherein the subject has not been previously diagnosed as having a neuropathy;

(c) wherein the subject does not meet the diagnostic criteria for Stage 1 familial amyloid polyneuropathy (FAP);

(d) wherein the subject has a TTR mutation associated with TTR amyloidosis;

(e) wherein the subject does not have a mutation associated with TTR amyloidosis;

(f) wherein the subject also has an altered level of one or more proteins selected from the group consisting of RSPO3, CCDC80, EDA2R, N-CDase, NT-proBNP, WNT9A, SMOC2, PTN, HGF, HELL1, DCN, ARSA, KLK4, GPC1, SFRP, DRAXIN, IL-18R1, BNP, GFR-alpha1, CXCL9, TIMD4, RSPO1, MYOC, WFDC2, GUSB, HSPB6, MFGE8, SMPD1, FLT1, CTSD, CD209, LDLR, NOV, CD160, PI3, SMOC1, TFPI-2, LEP, TNFRSF19, ERBB3, DUA, IL-4RA, REN, CES2, CR2, PSG1, FGF-BP1, OPN, TFF3, ANGPT2, CCL24, LAYN, FUCA1, AXL, TLR3, SCARB2, B4GAT1, SORCS2, CD300E, CD27, SPON1, IGFBP-2, DNER, RARRES1 and Dkk-4 as compared to a reference level, wherein an increase in the level of a protein having a positive beta coefficient relative to a reference level is indicative of progression of TTR amyloidosis, or wherein a decrease in the level of a protein having a negative beta coefficient relative to a reference level is indicative of progression of TTR amyloidosis;

(g) wherein the subject is being treated with a therapeutic agent that stabilizes TTR; and/or (h) wherein the subject is further suffering from one or more of orthostatic hypotension, diarrhea, constipation, erectile dysfunction, glaucoma, intravitreal deposition, scalloped pupils, carpal tunnel syndrome, lumbar spinal stenosis, and bicep tendon rupture.

4. The method of claim 3, wherein the one or more proteins are selected from the group consisting of RSPO3, CCDC80, EDA2R, NT-proBNP, and N-CDase.

5. The method of claim 1, wherein the reference level of NfL is (i) a healthy control level or an earlier level in the same subject; (ii) 30-50 μg/ml in plasma, or 35-40 μg/ml in plasma; or (iii) 37 μg/ml in plasma.

6. The method of claim 3, wherein the agent that stabilizes TTR is tafamidis or diflunisal.

7. The method of claim 3, further comprising discontinuation of treatment with the therapeutic agent that stabilizes TTR when the subject has an elevated level of NfL.

8. The method of claim 1, wherein the biological sample is selected from the group consisting of blood, plasma, and serum.

9. A method of treating TTR amyloidosis polyneuropathy in a human subject in need thereof, the method comprising:

(a) determining the level of NfL in a biological sample from the subject;

(b) comparing the level of NfL determined in step (a) to a reference level of NfL;

(c) assessing whether the subject suffers from TTR amyloidosis polyneuropathy, wherein an increase in the level of NfL determined in step (a) as compared to the reference level of NfL is indicative of the subject suffering from TTR amyloidosis polyneuropathy; and (d) administering an RNAi agent or an antisense oligonucleotide that reduces expression of TTR to the subject that has been identified in step (c) as suffering from TTR amyloidosis polyneuropathy, thereby treating TTR amyloidosis polyneuropathy in the subject.

10. The method of claim 9, wherein the RNAi agent or the antisense oligonucleotide is selected from the group consisting of patisiran, vutrisiran, inotersen and ION-TTR-LRx.

11. The method of claim 9, (a) wherein the subject has not been previously diagnosed with hTTR amyloidosis polyneuropathy;

(b) wherein the subject has not been previously diagnosed as having a neuropathy;

(c) wherein the subject does not meet the diagnostic criteria for Stage 1 familial amyloid polyneuropathy (FAP);

(d) wherein the subject has a TTR mutation associated with TTR amyloidosis;

(e) wherein the subject does not have a mutation associated with TTR amyloidosis;

(f) wherein the subject also has an altered level of one or more proteins selected from the group consisting of RSPO3, CCDC80, EDA2R, N-CDase, NT-proBNP, WNT9A, SMOC2, PTN, HGF, HELL1, DCN, ARSA, KLK4, GPC1, SFRP, DRAXIN, IL-18R1, BNP, GFR-alpha1, CXCL9, TIMD4, RSPO1, MYOC, WFDC2, GUSB, HSPB6, MFGE8, SMPD1, FLT1, CTSD, CD209, LDLR, NOV, CD160, PI3, SMOC1, TFPI-2, LEP, TNFRSF19, ERBB3, DUA, IL-4RA, REN, CES2, CR2, PSG1, FGF-BP1, OPN, TFF3, ANGPT2, CCL24, LAYN, FUCA1, AXL, TLR3, SCARB2, B4GAT1, SORCS2, CD300E, CD27, SPON1, IGFBP- 2, DNER, RARRES1 and Dkk-4 as compared to a reference level, wherein an increase in the level of a protein having a positive beta coefficient relative to a reference level is indicative of progression of TTR amyloidosis, or wherein a decrease in the level of a protein having a negative beta coefficient relative to a reference level is indicative of progression of TTR amyloidosis;

(g) wherein the subject is being treated with a therapeutic agent that stabilizes TTR; and/or (h) wherein the subject is further suffering from one or more of orthostatic hypotension, diarrhea, constipation, erectile dysfunction, glaucoma, intravitreal deposition, scalloped pupils, carpal tunnel syndrome, lumbar spinal stenosis, and bicep tendon rupture.

12. The method of claim 11, wherein the one or more proteins are selected from the group consisting of RSPO3, CCDC80, EDA2R, NT-proBNP, and N-CDase.

13. The method of claim 9, wherein the reference level of NfL is (i) a healthy control level or an earlier level in the same subject; (ii) 30-50 μg/ml in plasma, or 35-40 μg/ml in plasma; or (iii) 37 μg/ml in plasma.

14. The method of claim 11, wherein the agent that stabilizes TTR is tafamidis or diflunisal.

15. The method of claim 11, further comprising discontinuation of treatment with the therapeutic agent that stabilizes TTR when the subject has an elevated level of NfL.

16. The method of claim 9, wherein the biological sample is selected from the group consisting of blood, plasma, and serum.

* * * * *